US012584675B2

(12) United States Patent     (10) Patent No.:   US 12,584,675 B2

Nevo et al.     (45) Date of Patent:    Mar. 24, 2026

---

(54) COLD PACKS SYSTEM

(71) Applicant: Arctic Express Packs LLC, Fort Worth, TX (US)

(72) Inventors: Shlomo Nevo, Tel-Aviv (IL); Brian H. Bunnett, Highland Village, TX (US)

(73) Assignee: Arctic Express Packs LLC, Fort Worth, TX (US)

( * ) Notice: Subject to any disclaimer, the term of this patent is extended or adjusted under 35 U.S.C. 154(b) by 1283 days.

(21) Appl. No.: 16/641,277

(22) PCT Filed: Aug. 23, 2018

(86) PCT No.: PCT/IL2018/050931

§ 371 (c)(1),
(2) Date: Feb. 24, 2020

(87) PCT Pub. No.: WO2019/038767

PCT Pub. Date: Feb. 28, 2019

(65) Prior Publication Data

US 2020/0182526 A1    Jun. 11, 2020

Related U.S. Application Data

(60) Provisional application No. 62/549,470, filed on Aug. 24, 2017.

(51) Int. Cl.
| | |
|---|---|
| *F25D 3/08* | (2006.01) |
| *A61F 7/02* | (2006.01) |
| *A61F 7/10* | (2006.01) |

(52) U.S. Cl.
CPC ................. *F25D 3/08* (2013.01); *A61F 7/10* (2013.01); *A61F 7/02* (2013.01);
(Continued)

(58) Field of Classification Search
CPC ................. F25D 3/08; F25D 2303/082; F25D 2331/804; F25D 2303/085; A61F 7/10;
(Continued)

(56) References Cited

U.S. PATENT DOCUMENTS

| | | |
|---|---|---|
| 3,574,271 A | 4/1971 | Andersson |
| 3,951,127 A | 4/1976 | Watson et al. |

(Continued)

FOREIGN PATENT DOCUMENTS

| | | |
|---|---|---|
| EP | 0558889 | 12/1999 |
| EP | 1592376 | 11/2005 |

(Continued)

OTHER PUBLICATIONS

KR 20070020853 A Translation (Year: 2007).*

(Continued)

*Primary Examiner* — Jerry-Daryl Fletcher
*Assistant Examiner* — Dario Antonio Deleon

(57) ABSTRACT

A pack with Super Absorbent Material (SAM) inside and without refrigerant fluid inside. A system for dispensing a cold pack including a filling unit for taking in a waterproof SAM pack with SAM inside and without refrigerant fluid inside and adding refrigerant fluid to an inside of the SAM pack, producing a refrigerant pack. Apparatus for producing a cold pack including a SAM source, a source of refrigerant fluid, a bag filler for filling a bag with a mixture of SAM and refrigerant fluid, producing a refrigerant pack, and a cooler for cooling the refrigerant pack, thereby producing a cold pack. Related apparatus and methods are also described.

30 Claims, 32 Drawing Sheets

(52) U.S. Cl.
CPC ................. *A61F 2007/0219* (2013.01); *A61F 2007/0228* (2013.01); *A61F 2007/026* (2013.01); *A61F 2007/108* (2013.01); *F25D 2303/082* (2013.01); *F25D 2331/804* (2013.01)

(58) Field of Classification Search
CPC ................ A61F 7/02; A61F 2007/0219; A61F 2007/0228; A61F 2007/026; A61F 2007/108; A61F 2007/0214
See application file for complete search history.

(56) References Cited

U.S. PATENT DOCUMENTS

| | | | | |
|---|---|---|---|---|
| 4,856,651 A * | 8/1989 | Francis, Jr. ............... | A61F 7/03 206/219 |
| 5,150,707 A | 9/1992 | Anderson | |
| 5,709,089 A * | 1/1998 | Dawson et al. .......... | F25D 3/02 62/4 |
| 6,376,034 B1 * | 4/2002 | Brander ............... | B65D 81/264 428/35.2 |
| 6,478,147 B1 | 11/2002 | Brander et al. | |
| 6,491,993 B1 * | 12/2002 | Forbes et al. ........ | B01J 20/2805 428/34.3 |
| 7,795,345 B2 | 9/2010 | Smith et al. | |
| 2003/0139291 A1 | 7/2003 | Qin | |
| 2006/0173430 A1 | 8/2006 | Lee et al. | |
| 2007/0167560 A1 | 7/2007 | Smith et al. | |
| 2009/0120824 A1 | 5/2009 | Piazza | |
| 2009/0157154 A1 | 6/2009 | Hojbjerg | |
| 2010/0057027 A1 | 3/2010 | Furno et al. | |
| 2011/0126582 A1 | 6/2011 | Duong et al. | |
| 2011/0210120 A1 | 9/2011 | Nevo | |
| 2011/0270300 A1 * | 11/2011 | De Luis et al. .. | A61F 13/00017 606/213 |
| 2014/0371552 A1 * | 12/2014 | Gerlitz et al. ........... | A61F 7/10 600/310 |
| 2015/0210032 A1 | 7/2015 | Blackford et al. | |
| 2017/0029994 A1 | 2/2017 | Ashraf et al. | |
| 2023/0199521 A1 | 6/2023 | Nevo et al. | |

FOREIGN PATENT DOCUMENTS

| | | | | |
|---|---|---|---|---|
| GB | 2251206 | 7/1992 | | |
| KR | 20070020853 A * | 2/2007 | ............... | A61F 7/02 |

| | | |
|---|---|---|
| WO | WO 2018/132812 | 7/2018 |
| WO | WO 2019/038767 | 2/2019 |
| WO | WO 2019/195272 | 10/2019 |
| WO | WO 2019/246215 | 12/2019 |
| WO | WO 2021/220180 | 11/2021 |

OTHER PUBLICATIONS

Communication Pursuant to Article 94(3) EPC Dated Jan. 3, 2023 From the European Patent Office Re. Application No. 18847522.2 (6 Pages).

International Search Report and the Written Opinion Dated Jul. 21, 2021 From the International Searching Authority Re. Application No. PCT/IL202/053508. (10 Pages).

Bucevschi et al.

Supplementary European Search Report and the European Search Opinion Dated Apr. 16, 2021 From the European Patent Office Re. Application No. 18847522.2. (8 Pages).

International Preliminary Report on Patentability Dated Mar. 5, 2020 From the International Bureau of WIPO Re. Application No. PCT/IL2018/050931. (10 Pages).

International Search Report and the Written Opinion Dated Feb. 5, 2019 From the International Searching Authority Re. Application No. PCT/IL2018/050931. (17 Pages).

Invitation to Pay Additional Fees Dated Dec. 6, 2018 From the International Searching Authority Re. Application No. PCT/IL2018/050931. (3 Pages).

Unknown "Ice Bag", Product Instruction Page, 1 P., 2017.

International Preliminary Report on Patentability Dated Nov. 10, 2022 From the International Bureau of WIPO Re. Application No. PCT/IL202/053508. (9 Pages).

"Certificate for Awarding and Use of the 'OK Compost' Conformity Mark", Vincotte, 1P., Sep. 20, 2017.

Requisition by the Examiner Dated Aug. 28, 2023 From the Innovation, Science and Economic Development Canada, Canadian Intellectual Property Office Re. Application No. 3,072,611. (4 Pages).

Supplementary European Search Report and the European Search Opinion Dated May 3, 2024 From the European Patent Office Re. Application No. 21797453.4. (7 Pages).

Official Action Dated Aug. 12, 2024 From the U.S. Appl. No. 17/921,659. (39 Pages).

\* cited by examiner

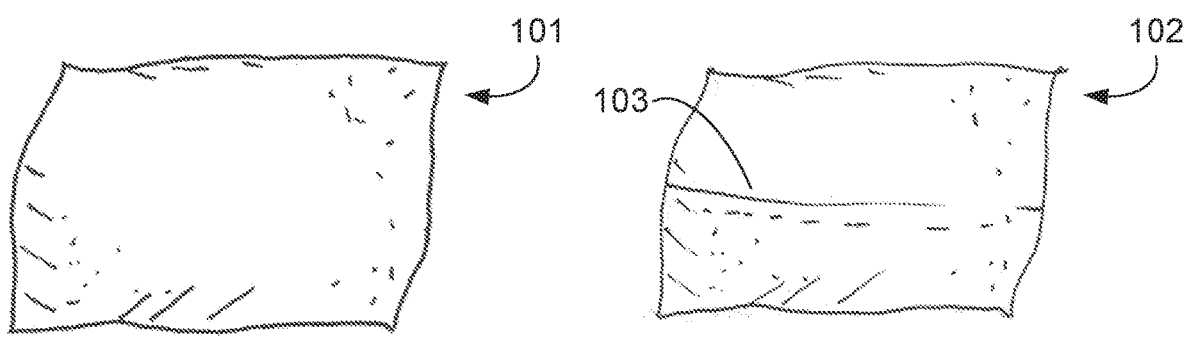
FIGURE 1A - PRIOR ART
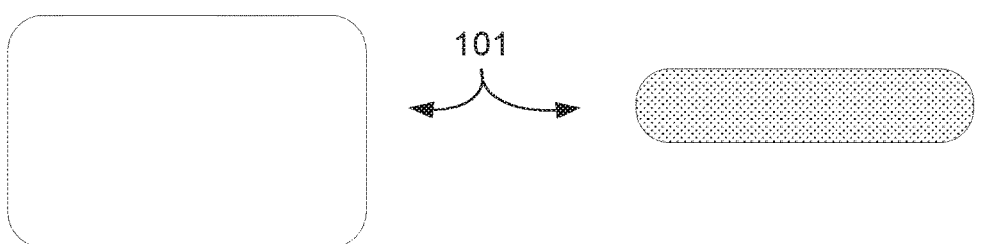
FIGURE 1B – PRIOR ART        FIGURE 1C – PRIOR ART
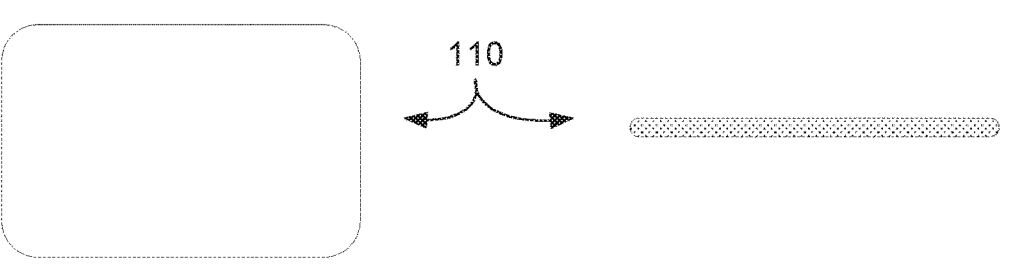
FIGURE 1D                FIGURE 1E
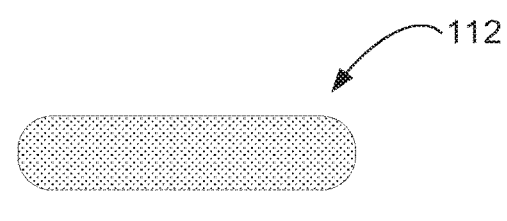
FIGURE 1F

| 131 | 131 |
|---|---|

FIGURE 1J

| 132 | 132 | ... | 132 |
|---|---|---|---|

FIGURE 1K

| 133 | 133 | ... | 133 |
|---|---|---|---|
| 133 | 133 | ... | 133 |

| 133 | 133 | ... | 133 |
|---|---|---|---|

PROVIDE A SAM PACK          270

ADD REFRIGERANT FLUID TO
THE SAM PACK          272

SEAL THE REFRIGERANT PACK          274

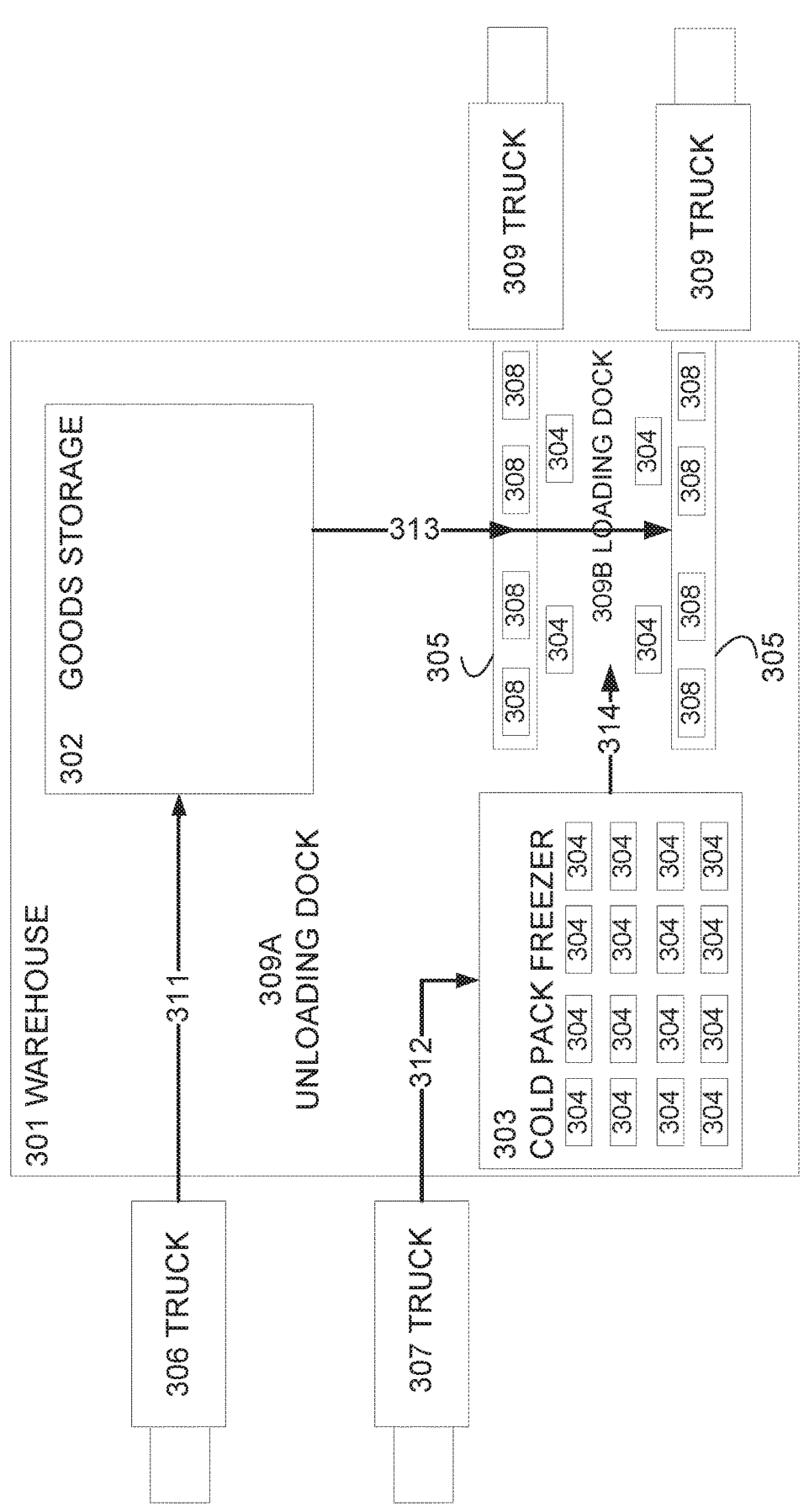
FIGURE 3A - PRIOR ART

ROBOT RECEIVES DATA
DESCRIBING GOODS ⟶ 422

ROBOT PICKS UP GOODS ⟶ 424

ROBOT PICKS UP COLD
PACK(S) ⟶ 426

ROBOT PACKS GOODS AND
COLD PACKS IN GOODS
SHIPPING BOX ⟶ 428

COLD PACKS SYSTEM

RELATED APPLICATIONS

This application is a National Phase of PCT Patent Application No. PCT/IL2018/050931 having International filing date of Aug. 23, 2018, which claims the benefit of priority under 35 USC § 119(e) of U.S. Provisional Patent Application No. 62/549,470 filed on Aug. 24, 2017. The contents of the above applications are all incorporated by reference as if fully set forth herein in their entirety.

FIELD AND BACKGROUND OF THE INVENTION

The present invention, in some embodiments thereof, relates to temperature control packs, systems and methods for providing temperature control packs and, more particularly, but not exclusively, to cold packs, systems and method for providing cold packs and, even more particularly, but not exclusively, to frozen packs, systems and method for providing frozen packs.

The disclosures of all references mentioned above and throughout the present specification, as well as the disclosures of all references mentioned in those references, are hereby incorporated herein by reference.

SUMMARY OF THE INVENTION

An aspect of some embodiments of the invention relates to a pack with an absorbent material inside, and without refrigerant fluid. In an example embodiment the absorbent material is a Super Absorbent Material (SAM) such as Super Absorbent Polymer (SAP).

The terms "Super Absorbent Material" and "SAM" are used throughout the present application and claims to mean an absorbent material for use inside a cold pack. In some embodiments the absorbent material is a Super Absorbent Material, optionally SAP (Super Absorbent Polymer).

The term "SAM pack" in all its grammatical forms is used in the present application and claims to mean a pack, according to an example embodiment of the invention, containing absorbent material, and without refrigerant fluid.

An aspect of some embodiments of the invention relates to providing a SAM pack with SAM inside, and without refrigerant fluid, according to some embodiments of the invention, filling the SAM pack with a refrigerant fluid, and dispensing refrigerant packs on demand. In an example embodiment the refrigerant fluid is water.

An aspect of some embodiments of the invention relates to a freezer with a conveyor belt, for taking in refrigerant packs or SAM packs and passing them through the freezer to emerge as cold packs frozen or cooled to a desired temperature.

According to an aspect of some embodiments of the present invention there is provided a SAM pack with SAM inside and without refrigerant fluid inside.

According to some embodiments of the invention, the SAM pack is waterproof.

According to some embodiments of the invention, the SAM pack is sealed closed. According to some embodiments of the invention, the SAM pack is heat-sealed closed. According to some embodiments of the invention, the SAM pack is glued closed.

According to some embodiments of the invention, the SAM pack having a thickness less than 20 millimeters.

According to some embodiments of the invention, the SAM pack having a thickness in a range between 2 millimeters and 200 millimeters.

According to some embodiments of the invention, the SAM pack is closed in a way which enables adding a refrigerant fluid without puncturing the SAM pack.

According to some embodiments of the invention, the SAM pack includes at least a portion of a seam glued weakly to enable opening and re-sealing. According to some embodiments of the invention, the SAM pack includes at least a portion of a seam sealed weakly to enable opening and re-sealing.

According to some embodiments of the invention, the portion of the seam sealed weakly is arranged to open in response to a force of 50-500 grams pulling sides of the SAM pack apart.

According to some embodiments of the invention, the portion of the seam sealed weakly is arranged to open in response to pressure of 0.25-2 bars.

According to some embodiments of the invention, the SAM pack includes a seam shaped to enable puncturing the SAM pack, adding a refrigerant fluid, and sealing, producing a refrigerant pack.

According to some embodiments of the invention, the SAM pack includes a seam shape which includes a crescent shaped line.

According to some embodiments of the invention, the SAM pack is provided as a connected strip of SAM packs. According to some embodiments of the invention, the SAM pack is provided as a fan-folded connected strip of SAM packs. According to some embodiments of the invention, the SAM pack is provided as a connected roll of SAM packs.

According to some embodiments of the invention, the SAM includes Super Absorbent Polymer (SAP). According to some embodiments of the invention, the SAM includes SAM in pill form.

According to an aspect of some embodiments of the present invention there is provided a method of producing a waterproof SAM pack including forming a pack of waterproof material, adding SAM to the pack without adding refrigerant fluid, producing a SAM pack, and sealing the SAM pack.

According to some embodiments of the invention, the sealing the SAM pack includes heat sealing the SAM pack. According to some embodiments of the invention, the sealing the SAM pack includes gluing the SAM pack.

According to some embodiments of the invention, the sealing the SAM pack includes sealing to enable adding a refrigerant fluid without puncturing the SAM pack.

According to some embodiments of the invention, the sealing the SAM pack includes sealing in a seam shape which enables puncturing the SAM pack, adding a refrigerant fluid, and sealing, producing a refrigerant pack.

According to some embodiments of the invention, the sealing the SAM pack includes sealing in a seal shape which includes a crescent shaped line.

According to some embodiments of the invention, the forming a pack includes forming a connected strip of packs.

According to some embodiments of the invention, the forming a pack includes forming separate packs, optionally separating a connected strip into separate packs.

According to some embodiments of the invention, the adding SAM to the pack includes adding SAM in pill form.

According to an aspect of some embodiments of the present invention there is provided a method of providing a refrigerant pack including providing a waterproof SAM pack with SAM inside and without refrigerant fluid inside, adding refrigerant fluid to an inside of the SAM pack, thereby producing a refrigerant pack, and sealing the refrigerant pack.

According to some embodiments of the invention, the sealing the refrigerant pack includes heat sealing the refrigerant pack. According to some embodiments of the invention, the sealing the refrigerant pack includes gluing refrigerant SAM pack.

According to some embodiments of the invention, the adding refrigerant fluid to the inside of the SAM pack includes puncturing the SAM pack, injecting refrigerant fluid to the inside of the SAM pack, producing a refrigerant pack, and sealing the refrigerant pack.

According to some embodiments of the invention, further including cooling the refrigerant pack, producing a cold pack. According to some embodiments of the invention, further including shipping the cold pack to a cold pack customer.

According to some embodiments of the invention, further including heating the refrigerant pack, producing a hot pack.

According to some embodiments of the invention, further including altering a temperature of the refrigerant pack, producing a pack for use for temperature control.

According to some embodiments of the invention, further including altering a temperature of the refrigerant pack to room temperature, producing a pack for use for temperature control of a Controlled Room Temperature container.

According to some embodiments of the invention, further including placing the SAM pack between walls of a SAM pack tray cell.

According to some embodiments of the invention, the adding refrigerant fluid to the inside of the SAM pack further includes pressurizing the refrigerant fluid for conveying the refrigerant fluid to the inside of the SAM pack.

According to some embodiments of the invention, the adding refrigerant fluid to the inside of the SAM pack includes adding refrigerant fluid to the inside of the SAM pack through a side of the SAM pack.

According to some embodiments of the invention, further including collecting the cold packs in a holding container.

According to some embodiments of the invention, the cooling the refrigerant pack includes freezing the refrigerant pack.

According to some embodiments of the invention, the cooling includes conveying the refrigerant packs on a conveyor belt through a cooling unit, to emerge as cold packs cooled to a desired temperature.

According to some embodiments of the invention, further including dispensing one or more cold packs based on at least one of the following considerations: intended duration of storage of the cold packs before packaging with merchandise, intended duration of storage of the merchandise, intended duration of shipping of the merchandise, to what temperature the merchandise may be cooled or frozen without damage, insulating parameters relating to an intended package, and maximum weight of cold packs plus merchandise in a package (for example when packaging cold pack(s) and merchandise for delivery by a drone with limited lifting capacity.

According to some embodiments of the invention, further including controlling at least one of the following parameters, based on at least one of the considerations: number of cold packs to be used, size of cold packs to be used, weight of cold packs to be used, total weight of cold packs to be used, weight of SAM in cold pack(s) to be used, weight of refrigerant fluid in cold packs to be used, and temperature of cold packs.

According to some embodiments of the invention, further including providing a specific number of cold packs at a specific temperature.

According to some embodiments of the invention, further including receiving electronic requests for dispensing cold packs. According to some embodiments of the invention, the receiving electronic requests includes receiving the electronic requests via a user interface terminal.

According to some embodiments of the invention, further including cooling the cold packs in the holding container by a second cooling unit.

According to some embodiments of the invention, further including detaching the holding container from the cooling unit.

According to some embodiments of the invention, the cooling the refrigerant pack includes cooling the refrigerant pack to a temperature in a range of 0 degrees Celsius to 8 degrees Celsius. According to some embodiments of the invention, the cooling the refrigerant pack includes cooling the refrigerant pack to freezing temperature yet not freezing the refrigerant pack. According to some embodiments of the invention, the cooling the refrigerant pack includes cooling the refrigerant pack to freezing temperature and also freezing the refrigerant pack. According to some embodiments of the invention, the cooling the refrigerant pack includes freezing the refrigerant pack to a temperature in a range of minus 40 degrees Celsius to 0 degrees Celsius. According to some embodiments of the invention, the cooling the refrigerant pack includes freezing the refrigerant pack to a temperature in a range of minus 75 degrees Celsius to minus 40 degrees Celsius.

According to some embodiments of the invention, further including providing a specific number of cold packs at a specific temperature in response to an electronic request specifying the specific number of cold packs and the specific temperature.

According to some embodiments of the invention, further including providing a specific number of cold packs at a specific temperature starting with a cooling machine with no cold packs inside.

According to some embodiments of the invention, including taking in a strip of connected SAM packs and producing a strip of connected cold packs.

According to some embodiments of the invention, including taking in a strip of connected SAM packs and separating the SAM packs, producing a plurality of disconnected cold packs.

According to an aspect of some embodiments of the present invention there is provided a system for dispensing a cold pack including a filling unit for taking in a waterproof SAM pack with SAM inside and without refrigerant fluid inside and adding refrigerant fluid to an inside of the SAM pack, producing a refrigerant pack.

According to some embodiments of the invention, further including a sealing unit for sealing the refrigerant pack.

According to some embodiments of the invention, further including a first cooling unit for cooling the refrigerant pack, producing a cold pack.

According to some embodiments of the invention, further including a conveyor belt, for taking in refrigerant packs and passing the refrigerant packs through the cooling unit to emerge as cold packs cooled to a desired temperature.

According to some embodiments of the invention, the filling unit includes an injection needle for injecting the refrigerant fluid to the inside of the SAM pack.

According to some embodiments of the invention, the filling unit includes a pressurizing component for conveying the refrigerant fluid to the inside of the SAM pack.

According to some embodiments of the invention, the filling unit includes a pressurizing component for conveying refrigerant fluid through the injection needle.

According to some embodiments of the invention, the filling unit is arranged to perform the adding refrigerant fluid to the inside of the SAM pack through a side of the SAM pack.

According to some embodiments of the invention, further including a holding container for a plurality of cold packs. According to some embodiments of the invention, the first cooling unit also cools the holding container.

According to some embodiments of the invention, the first cooling unit is capable of freezing the refrigerant pack.

According to some embodiments of the invention, further including a chute for dispensing cold packs.

According to some embodiments of the invention, further including a communication unit for receiving electronic requests for dispensing cold packs. According to some embodiments of the invention, further including a user interface terminal for receiving user requests for dispensing cold packs.

According to some embodiments of the invention, the holding container is a detachable holding container.

According to some embodiments of the invention, the holding container includes a second cooling unit for cooling cold packs in the holding container.

According to some embodiments of the invention, the first cooling unit is capable of cooling the refrigerant pack to a temperature in a range of 0 degrees Celsius to 8 degrees Celsius. According to some embodiments of the invention, the first cooling unit is capable of freezing the refrigerant pack to a temperature in a range of minus 40 degrees Celsius to 0 degrees Celsius.

According to some embodiments of the invention, the system is designed to provide a specific number of cold packs at a specific designated temperature.

According to some embodiments of the invention, the system is designed to receive a strip of connected SAM packs and produce a strip of connected cold packs. According to some embodiments of the invention, the system is designed to receive a strip of connected SAM packs and separate the strip, producing a plurality of separate cold packs.

According to some embodiments of the invention the system is arranged to receive an electronic request for at least one cold pack and to produce the at least one cold pack in response to the electronic request.

According to some embodiments of the invention, the system further comprises a barcode reader and arranged to receive the electronic request by reading a barcode containing the electronic request, wherein reading the barcode containing the electronic request comprises reading the barcode from a shipping box.

According to some embodiments of the invention, producing the cold pack includes producing at least one cold pack in response to receiving an electronic request for at least one cold pack.

According to some embodiments of the invention, receiving the electronic request includes reading a barcode containing the electronic request. According to some embodiments of the invention, reading the barcode containing the electronic request includes reading the barcode from a shipping box.

According to an aspect of some embodiments of the present invention there is provided a method of providing a cold pack in a packing line including providing a SAM pack with SAM inside and without refrigerant fluid inside, adding refrigerant fluid to an inside of the SAM pack, thereby producing a refrigerant pack, sealing the refrigerant pack, cooling the refrigerant pack, thereby producing a cold pack, and providing the cold pack to the packing line.

According to some embodiments of the invention, the providing includes on-demand providing based on an electronic request. According to some embodiments of the invention, the cooling includes on-demand cooling to a specific temperature based on the electronic request.

According to an aspect of some embodiments of the present invention there is provided a computer interface for providing a cold pack, the computer interface including presenting a user interface for receiving a user input including at least one parameter selected from a group of parameters consisting of a requested number of cold packs, a specific size of the cold packs, a temperature of the cold pack(s), a duration for the cold packs to maintain cold, a type of the container into which the cold packs are to be added, a volume of a container to be cooled by the cold packs, a weight of goods to be cooled by the cold packs, and a heat mass of goods in a container for which the cold packs are intended. By way of a non-limiting example, a maximum weight or size of a package may be provided, for example for a container intended for shipping by a drone, and one or more of a weight, a temperature, and a size of a cold pack may be determined based on the maximum weight or size.

According to an aspect of some embodiments of the present invention there is provided a method of packing goods to be shipped at a controlled temperature including receiving an order for goods, determining whether the goods should be packaged with a cold pack, automatically providing the cold pack, based at least in part on the determining, and packing the cold pack in a shipping box with the goods.

According to some embodiments of the invention, the providing the cold pack includes manufacturing a refrigerant pack from a SAM pack, cooling the refrigerant pack, thereby producing a cold pack.

According to some embodiments of the invention, the determining whether the goods should be packaged with a cold pack includes receiving goods data describing goods to be packed, and translating the goods data to cold pack provision data.

According to some embodiments of the invention, receiving the goods data includes reading a barcode containing the goods data. According to some embodiments of the invention, reading the barcode containing the goods data includes reading the barcode from the shipping box. According to some embodiments of the invention, the goods data includes a parameter selected from a group consisting of goods total weight, goods total volume, goods type, desired temperature of goods when packaged, maximum desired temperature of goods when packaged, minimum desired temperature of goods when packaged, duration for temperature to stay between the minimum and the maximum, data about package insulation properties, and package volume.

According to some embodiments of the invention, the cold pack provision data includes a parameter selected from a group consisting of cold pack temperature, cold pack size, number of cold packs, whether the cold packs are to be provided as a cold pack strip, amount of refrigerant fluid to add into a SAM pack to produce a cold pack, and cold pack seam geometry.

According to some embodiments of the invention, the translating the goods data to cold pack provision data includes translating via a look-up table. According to some embodiments of the invention, the translating the goods data to cold pack provision data includes translating by calculating.

According to some embodiments of the invention, the translating the goods data to cold pack provision data includes producing a barcode containing the cold pack provision data. According to some embodiments of the invention, further including providing the barcode on the shipping box.

According to an aspect of some embodiments of the present invention there is provided a packing line for packing goods to be shipped at a controlled temperature including, storage for goods, a cold pack machine for producing cold packs from SAM packs, a packing line for packing goods received from storage and a cold pack received from the cold pack machine.

According to an aspect of some embodiments of the present invention there is provided a warehouse for packing goods to be shipped at a controlled temperature including storage for goods, a cold pack machine for producing cold packs from SAM packs, a packing line for packing goods received from storage and a cold pack received from the cold pack machine.

According to some embodiments of the invention, the warehouse does not contain a cold pack storage freezer apart from a cold pack machine.

According to an aspect of some embodiments of the present invention there is provided a method of packaging temperature sensitive items for delivery including packaging a temperature sensitive item in a package, producing a cold pack from a SAM pack, and packaging the cold pack in the package.

According to an aspect of some embodiments of the present invention there is provided apparatus for producing a cold pack including a SAM source, a source of refrigerant fluid, a bag filler for filling a bag with a mixture of SAM and refrigerant fluid, producing a refrigerant pack, and a cooler for cooling the refrigerant pack, thereby producing a cold pack.

According to some embodiments of the invention, further including a sealing unit for sealing the refrigerant pack.

According to some embodiments of the invention, further including a mixing unit for mixing the Sam and the refrigerant fluid.

According to some embodiments of the invention, further including a controller to control the production of cold packs.

According to an aspect of some embodiments of the present invention there is provided a method of producing a cold pack including taking in a bag, filling the bag with a mixture of SAM and refrigerant fluid, producing a refrigerant pack, sealing the refrigerant pack, and cooling the refrigerant pack, producing a cold pack.

According to some embodiments of the invention, the producing a cold pack includes producing in response to an electronic request for cold packs, the request including goods description parameters.

According to some embodiments of the invention, further including translating the goods description parameters to cold pack manufacturing parameters.

According to some embodiments of the invention, the producing a cold pack includes producing in response to an electronic request for cold packs, the request including cold pack manufacturing parameters.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a simplified illustration of prior art cold packs;

FIGS. 1B and 1C are simplified line drawing illustrations of a prior art cold pack;

FIGS. 1D and 1E are simplified line drawing illustrations of a SAM pack according to an example embodiment of the invention;

FIG. 1F is a simplified line drawing illustration of a cold pack according to an example embodiment of the invention;

FIGS. 1I-K are simplified line drawing illustrations of cold packs according to some example embodiment of the invention;

FIG. 3A is a simplified block diagram illustration of warehouse operation according to prior art;

FIG. 6A is a simplified illustration of a cold pack machine according to an example embodiment of the invention;

FIG. 10E, which is a simplified illustration of a pack including a seam design according to an example embodiment of the invention;

FIG. 10F is a simplified illustration of a pack including a seam design according to an example embodiment of the invention; and FIG. 10G, which is a simplified illustration of a pack including a seam design according to an example embodiment of the invention.

DESCRIPTION OF SPECIFIC EMBODIMENTS OF THE INVENTION

Figures 1G, 1H:
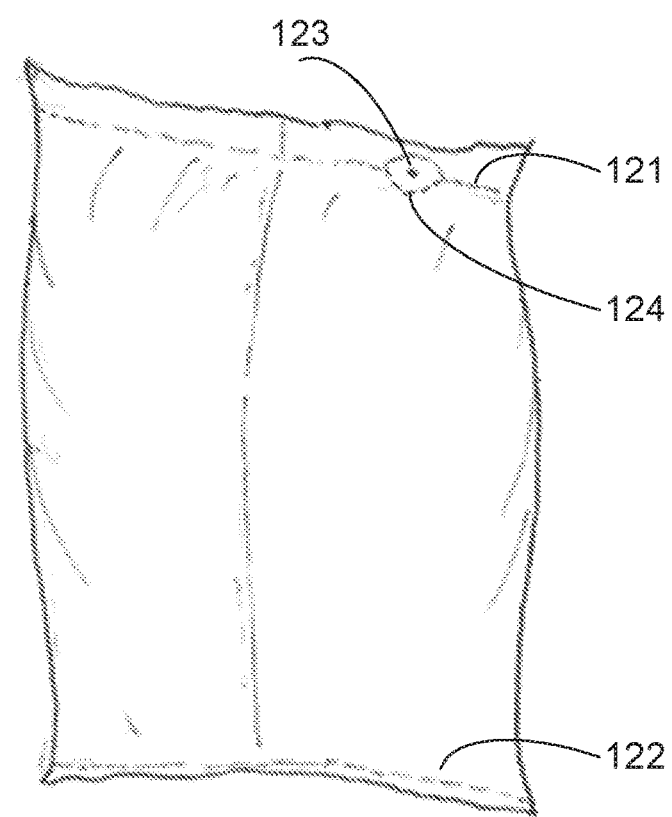
FIG. 1G is a simplified line drawing illustrations of a SAM pack according to an example embodiment of the invention.
FIG. 1H is a simplified line drawing illustration of a refrigerant pack according to an example embodiment of the invention.

The present invention, in some embodiments thereof, relates to temperature control packs, systems and methods for providing temperature control packs and, more particularly, but not exclusively, to cold packs, systems and method for providing cold packs and, even more particularly, but not exclusively, to frozen packs, systems and method for providing frozen packs.

Introduction

An ice pack or gel pack is a portable plastic sac filled with water, or refrigerant gel or fluid. For use the contents are frozen in a freezer. Both ice and other non-toxic refrigerants (mostly water) can absorb a considerable amount of heat before they warm above 0° C., due to a high latent heat of fusion of water. These packs are commonly used to keep goods such as food, pharmaceuticals and medical supplies cool in portable coolers; as a cold compress to alleviate the pain of minor injuries; and in insulated shipping containers to keep products cool during transport.

Ice packs may be provided frozen for immediate use; frozen in insulated packages for eventual use; or at room temperature for eventual freezing. However, such ice packs are heavy, due to presence of water or other fluid.

An aspect of some embodiments of the invention relates to a pack with SAM inside, and without refrigerant fluid such as water inside. Such a pack weighs less, and takes up less space.

Prior art packs include water or refrigerant gel. Such packs are heavier than if provided without water, and take up more volume. The smaller weight and volume of a pack according to some example embodiments save expense relative to transporting commercial quantities of prior art packs. Expense is saved by transporting less weight, and by transporting less volume. The smaller weight and volume of a pack according to some example embodiments save expense relative to storing commercial quantities of prior art packs. Expense is saved by storing less volume, and by taking up less floor space.

The term "SAM pack" in all its grammatical forms is used in the present application and claims to mean a pack, according to an example embodiment of the invention, containing absorbent material, and without refrigerant fluid.

The term "refrigerant pack" in all its grammatical forms is used in the present application and claims to mean a SAM pack, according to an example embodiment of the invention, which also contains a refrigerant fluid.

The adjectives "cold" or "frozen", in all their grammatical forms, will be added to the term "pack" to describe when the pack is cold or frozen, or even heated, regardless of a specific temperature. When a definite temperature is intended, the temperature is written.

The term "cold pack", in all its grammatical forms, is used in the present specification and claims to mean a refrigerant pack at a specific temperature, whether frozen, cold, room-temperature or hot, for use as a temperature-affecting pack. Such a pack may be cold—for cooling or maintaining cold, at room temperature for maintaining temperature in a Controlled Room Temperature (CRT) environment, and hot—for heating or maintaining heat. A refrigerant pack according to the present invention has a heat capacity which may optionally be used for cooling or maintaining cold, for maintaining temperature in a Controlled Room Temperature (CRT) environment, and for heating or maintaining heat.

Super Absorbent Materials (SAMs), sometimes also called slush powder, can absorb and retain extremely large amounts of a fluid relative to their own mass. In various embodiments, the SAM may include one or more of, by way of some non-limiting examples: a Super Absorbent Polymer (SAP) material; gelatin; SAP in pill form, a Carboxymethyl cellulose (CMC) based gel, or materials commonly known in the art.

In various embodiments, the refrigerant fluid may include one or more of, by way of some non-limiting examples: water; de-ionized water, de-salinated water, anti-freeze fluid, treated water, and fluids commonly known in the art.

In some embodiments the SAM pack includes a moisture absorbing laminate film.

In some embodiments the pack includes water only with no SAP. In the present application and claims where the terms SAM pack or cold pack are used, a person skilled in the art should also understand use of a pack which includes water only with no SAP.

In some embodiments of the invention, the SAM pack is waterproof, absorbing no water until water is introduced on purpose. Such embodiments potentially prevent a need to keep water and/or moisture away from the SAM packs, and potentially prevent the SAM packs getting heavy over time by absorbing moisture.

In some embodiments of the invention, the waterproof material includes plastic film, such as polyethylene.

In some embodiments of the invention, material forming the pack is spun-woven and backed to a polyethylene film for moisture absorbance. In some embodiments the SAP is optionally a non-toxic CMC based gel.

In some embodiments the SAM packs are sealed in a way which allows filling with water and re-sealing, producing refrigerant packs.

In some embodiments, the SAM pack is heat sealed, and the SAM pack is subsequently penetrated to allow filling with water, and re-sealed, producing a refrigerant pack.

In some embodiments, the SAM pack is mechanically sealed by pressure of filling.

In some embodiments, when the SAM pack is filled with refrigerant fluid the pack changes shape and seals against fluid leakage.

In some embodiments the SAM packs are not sealed.

An aspect of some embodiments of the invention relates to taking a SAM pack with SAM inside, and without water inside, according to some embodiments of the invention, and dispensing cold packs on demand.

In some embodiments, a first machine takes in a SAM pack and fills the pack with water or other fluid, dispensing a refrigerant pack with refrigerant fluid ready for cooling and/or freezing.

In some embodiments, a second machine takes in a refrigerant pack which already includes refrigerant fluid, and cools or freezes the refrigerant pack, dispensing a cold pack.

In some embodiments, a third machine takes in a SAM pack and fills the pack with water or other fluid, producing a refrigerant pack with refrigerant fluid ready for cooling and/or freezing, and cools or freezes the refrigerant pack, dispensing a cold pack.

In some embodiments, a fourth machine takes in an empty pack, with no SAM inside, fills the pack with SAM and water or other fluid, producing a refrigerant pack with refrigerant fluid ready for cooling and/or freezing, and cools or freezes the refrigerant pack, dispensing a cold pack.

In some embodiments, a fourth machine takes in an empty pack, with no SAM inside, fills the pack with a mixture of SAM and water or other fluid, producing a refrigerant pack with refrigerant fluid ready for cooling and/or freezing, and cools or freezes the refrigerant pack, dispensing a cold pack.

In some embodiments, a machine provides a consistently-shaped gel pack.

In some embodiments, the machine provides a gel pack shaped in a brick format.

An aspect of some embodiments of the invention relates to a freezer with a conveyor belt, for taking in refrigerant packs or SAM packs and passing them through the freezer to emerge as cold packs frozen or cooled to a desired temperature.

In some embodiments the freezer includes a chute for dispensing cold packs. In some embodiments the cooling and/or freezing is performed Just-In-Time, optionally in response to a computer request and/or to a user request via a user interface. In some embodiments the dispensing is performed Just-In-Time, optionally in response to a computer request and/or to a user request via a user interface.

In some embodiments the freezer includes a storage box, optionally a detachable storage box, where cold or frozen packs are accumulated until needed.

In some embodiments the freezer dispenses cold packs at different controlled temperatures.

In some embodiments the freezer dispenses a specific number of cold packs based on a computerized request.

An aspect of some embodiments of the invention relates to taking a non-frozen refrigerant pack or SAM pack and producing a cold pack. In some embodiments the refrigerant pack or SAM pack is in a form of a strip of refrigerant packs or SAM packs, and producing means producing a strip of cold packs.

An aspect of some embodiments of the invention relates to taking an empty bag and producing a cold pack.

In some embodiments the empty bag is in a form of a strip of empty bags.

In some embodiments the empty bag is filled with a mixture of SAM and refrigerant fluid, producing a refrigerant pack, and cooling the refrigerant pack.

In some embodiments the production of a cold pack from an empty bag occurs in one machine.

In some embodiments the production of a cold pack from an empty bag occurs in response to an electronic request defining cold pack parameters.

In some embodiments the production of a cold pack from an empty bag occurs in response to an electronic request defining goods and/or shipping package parameters, and the production includes translating the goods and/or shipping package parameters to cold pack manufacturing and/or dispensing parameters.

An aspect of some embodiments of the invention relates to a packing line including a machine for providing one or more cold pack(s) on-demand.

An aspect of some embodiments of the invention relates to using a robot to pack goods and cold packs in a goods shipping box.

An aspect of some embodiments of the invention relates to use of a machine for providing cold packs on-demand.

In some embodiments the methods include methods for rapid dispensing of one or more first cold packs after a period when the machine had not been used for cooling.

In some embodiments the methods include methods for storing cold packs for rapid dispensing of one or more first cold packs after a period when the machine had not been used for cooling.

In some embodiments the methods include methods for using such a machine when integrated into a packing line, for dispensing cold packs.

In some embodiments the methods include methods for using such a machine as a stand-alone machine, not integrated into a packing line, for dispensing cold packs.

An aspect of some embodiments of the invention relates to an interface to a machine for providing cold packs on-demand.

In some embodiments the interface includes an electronic interface for providing a computerized request for cold packs, including one or more features of a cold pack request, such as, by way of some non-limiting examples: a specific number of cold packs, a specific size of cold packs, a specific temperature of cold packs, a specific period of time for the cold packs to maintain a temperature less than a specific temperature, a specific volume of container for which the cold packs are intended, a specific weight of material in a container for which the cold packs are intended, a specific heat mass of material in a container for which the cold packs are intended, and so on.

In some embodiments the interface includes an interface for a user to provide input of a request for cold packs, including any one or more of the above-mentioned features of the request.

An aspect of some embodiments of the invention relates to handling a request for goods delivery and determining a command for cold pack dispensing associated with the request. The request may be received from a goods delivery center, or a data collection center. In some embodiments the request is analyzed to determine goods request parameters which pertain to determining a desired cooling capacity. In some embodiments the goods request parameters are translated to cold pack parameters such as a size of a cold pack, a number of cold packs, and temperature of the cold pack, which are capable of providing the desired cooling capacity. For purposes of better understanding some embodiments of the present invention, reference is first made to FIG. 1A, which is a simplified illustration of prior art cold packs.

FIG. 1A shows a first cold pack 101 and a second cold pack 102. Both the first cold pack 101 and the second cold pack 102 include SAM and a refrigerant fluid inside the cold packs 101 102. The cold packs 101 102 are intended to appear as rather thick, three dimensional, full of refrigerant fluid.

The second cold pack 102 also shows a sealed seam 103.

Reference is now made to FIGS. 1B and 1C, which are simplified line drawing illustrations of a prior art cold pack.

FIG. 1B shows a top view of a prior art cold pack 101, and FIG. 1C shows a side view of the prior art cold pack 101. FIG. 1C is intended to illustrate that the prior art cold pack 101 is full of refrigerant fluid and therefore somewhat thick, for example in comparison to the SAM pack illustrated in FIGS. 1D and 1E.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIGS. 1D and 1E, which are simplified line drawing illustrations of a SAM pack according to an example embodiment of the invention.

FIG. 1D shows a top view of a SAM pack 110, and FIG. 1E shows a side view of the SAM pack 110. FIG. 1E is intended to illustrate that the SAM pack 110 does not include refrigerant fluid and is therefore thinner and lighter than the prior art cold pack 101 of FIGS. 1B and 1C.

In some embodiments the SAM pack 110 is completely sealed and waterproof. In such embodiments the SAM pack 110 is potentially immune to soaking up moisture and becoming heavier and thicker/larger unless fluid is intentionally injected into the SAM pack 110.

In some embodiments the SAM pack 110 also includes an opening (not shown) for injecting refrigerant fluid such as water. In some embodiments the opening is a small opening, potentially reducing a possibility of soaking up moisture and becoming heavier and thicker/larger unless fluid is intentionally injected into the SAM pack 110 through the small opening. In some embodiments the opening is in a short end of the SAM pack 110. In some embodiments the opening is in a long end of the SAM pack 110. In some embodiments the opening is in a corner of the SAM pack 110.

In some embodiments a portion of a seam of the SAM pack 110, or a portion of an edge of the SAM pack 110 is sealed so that a force of 50-500 grams pulling sides of the SAM pack 110 apart opens the portion of the seam or edge of the SAM pack 110.

In some embodiments a portion of the seam or edge is sealed so that a fluid refrigerant pressure in a range of 0.25, 0.5, 0.75 and 1 bar and up to 5 bars opens the seam or edge of the SAM pack 110.

In some embodiments the SAM pack 110 is not sealed. In some embodiments the SAM pack 110 is optionally open until filled with water, then sealed. In some embodiments the SAM pack 110 is optionally open until filled with refrigerant fluid, and not even sealed after filling with refrigerant fluid.

The SAM pack 110 is intended to illustrate different sized packs, such as, by way of some non-limiting example, 7.5 oz., 9 oz., 13 oz., 16 oz., 18 oz., 26 oz., 32 oz., 34 oz., 58 oz., 60 oz. and 64 oz. A range of optional pack sizes includes 0.5 ounces to 128 ounces.

A typical SAM pack 110 according to example embodiments of the invention may range in length from 1 inch to 15 inches, and in width in length from 1 inch to 15 inches, however larger SAM packs are also contemplated, and are made when needed.

A typical SAM pack 110, containing SAM and no fluid according to example embodiments of the invention may range in thickness from 1 millimeter to 20, to 40, to 60, to 80, to 100 and to 150 millimeters, however thicker SAM packs are also contemplated, and are produced when needed.

It is noted that the above-mentioned weights represent a weight of a pack which contains SAM and refrigerant fluid. The weights are written as weights of a pack which contains SAP and water in a typical ratio of 7 percent SAP and 93 percent water. However, the list of weights is not intended to be limiting or exact. A same-sized pack with a different ratio of SAM and refrigerant fluid, or a same-sized pack containing different SAMs and/or refrigerant fluid may have a different weight, and the sizes and weights of the above-mentioned packs are not intended to be limiting.

Furthermore, ratio of SAM weight to water weight may range from 5 percent to 10 percent and lower and/or higher. In some embodiments ratio of SAM weight to water is optionally made according to SAM manufacturer recommendation or specification. Furthermore, ratio of SAM weight to fluid refrigerant weight may differ according to the absorbent material manufacturer recommendation or specification and/or refrigerant fluid recommendation or specification.

Reference is now made to FIG. 1F which is a simplified line drawing illustration of a cold pack according to an example embodiment of the invention.

FIG. 1F shows a side view of a cold pack 112, produced by adding refrigerant fluid into the SAM pack 110 of FIGS. 1D and 1E. FIG. 1F is intended to illustrate that the cold pack 112 includes refrigerant fluid and is therefore thicker than the SAM pack 110 of FIGS. 1D and 1E.

The cold pack 112 is intended to illustrate different sized packs, such as, by way of some non-limiting example, 16 oz. 32 oz. and 64 oz.

Reference is now made to FIG. 1G, which is a simplified line drawing illustrations of a SAM pack according to an example embodiment of the invention.

FIG. 1G shows a sealed SAM pack 120, with a top seam 121 and a bottom seam 122.

In some embodiments the top seam 121 has a specific shape, as explained in more detail with reference to FIGS. 10A-10G.

Reference is now made to FIG. 1H, which is a simplified line drawing illustration of a refrigerant pack according to an example embodiment of the invention.

FIG. 1H shows a refrigerant pack 125 which is optionally the SAM pack 120 of FIG. 1G, following injection with refrigerant fluid. The injection is optionally made through the puncture 123, and the refrigerant pack 125 is shown as having optionally been sealed by an additional seam 124.

Reference is now made to FIGS. 1I-K which are simplified line drawing illustrations of cold packs according to some example embodiment of the invention.

In some embodiments SAM packs are optionally formed as two SAM packs attached to each other along their edges, optionally forming a pair of SAM packs.

FIG. 1I shows a pair of SAM packs 131.

In some embodiments SAM packs are optionally formed as several SAM packs attached to each other along their edges, optionally forming a line of SAM packs one SAM pack wide and several SAM packs long.

FIG. 1J shows a line of SAM packs 132 one SAM pack wide and several SAM packs long.

In some embodiments SAM packs are optionally formed as two or more lines of SAM packs attached to each other along an edge, optionally forming a two or more lines of SAM packs, in what is sometimes called a saddle bag configuration.

FIG. 1K shows several lines of SAM packs 133 attached to each other.

Figure 2A:
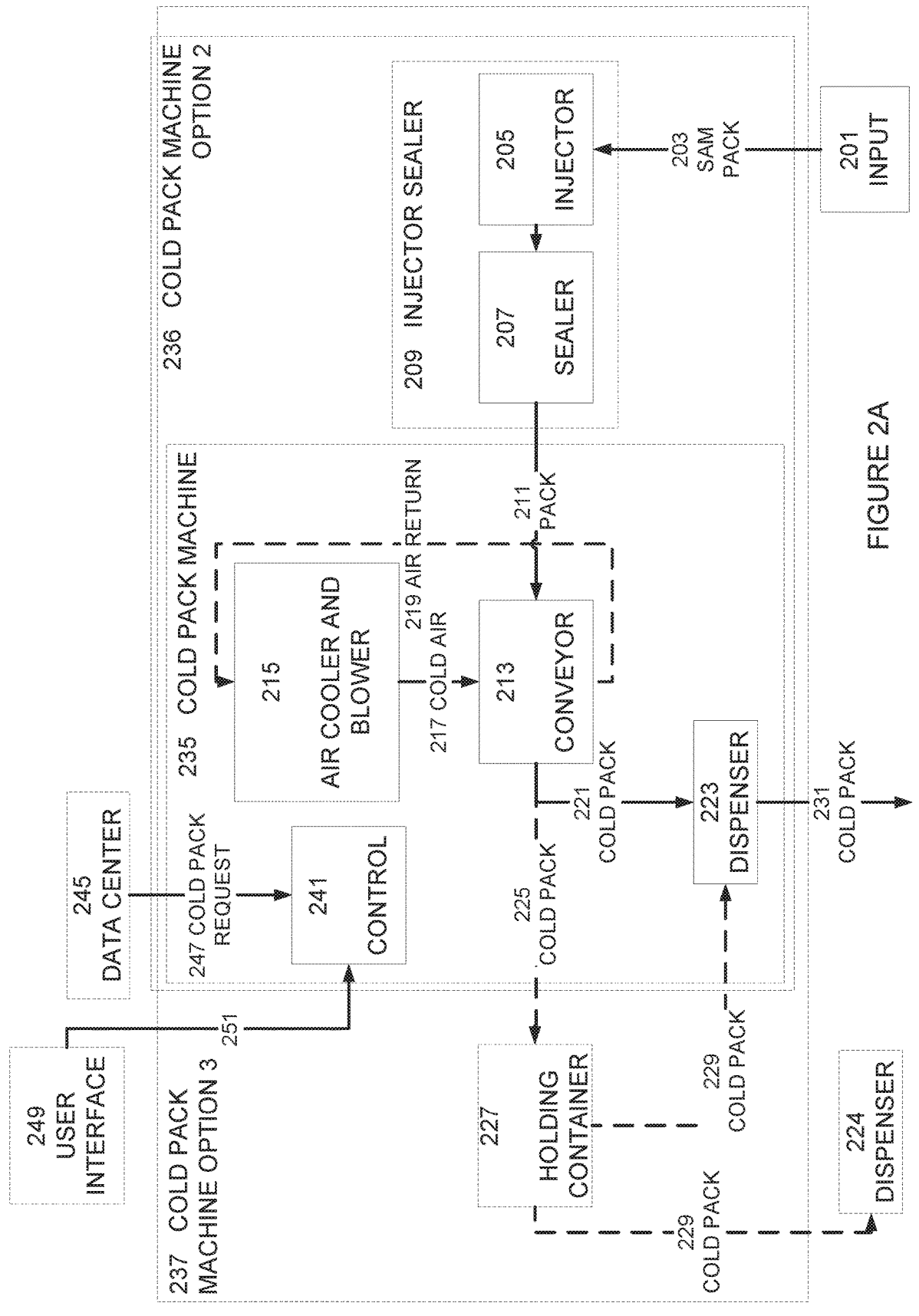
FIG. 2A is a simplified block diagram illustration of a system which takes in SAM packs and dispenses cold packs on demand, according to an example embodiment of the invention.

Reference is now made to FIG. 2A, which is a simplified block diagram illustration of a system which receives SAM packs and dispenses cold packs on demand, according to an example embodiment of the invention.

FIG. 2A shows some system components along a pack path, from a SAM pack input 201 to an optional cold pack dispenser 223.

In some embodiments, a SAM pack 203 is received at the SAM pack input 201, and enters an injector and sealer component 209, which includes an injector 205 for injecting refrigerant fluid into the SAM pack 203, and an optional sealer unit 207 for sealing the pack, producing a sealed pack 211 with refrigerant fluid. In some embodiments the SAM pack 203 may optionally be filled with refrigerant fluid and not sealed. The optionally sealed pack 211 with refrigerant fluid optionally enters onto, or optionally a user places onto, a conveyor 213 passing through a cold pack machine 235. The conveyor 213 carries the pack 211 through a cooler which cools the pack 211 to a desired temperature, producing a cold pack 221 225. Eventually the conveyor 213 dispenses the cold pack 221, optionally via an optional dispenser 223 as a cold pack 231.

In various embodiments, the conveyor may be a straight-line conveyor, a helical-path conveyor, a serpentine-path conveyor, and other types of conveyors as are known in the art. In some embodiments, the cold pack 225 is stored in an optional holding container 227, for optional dispensing later, for example by user taking the cold pack from the holding container 227, or by the holding container 227 dispensing a cold pack 229 in response to a computer command, optionally through the dispenser 223, or through another optional dispenser 224.

In some embodiments the holding container 227 optionally includes a separate cooler (not shown). In some embodiments the holding container 227 is optionally detachable from the cold pack machine.

In some embodiments the cold pack machine 235 includes the injector and sealer component 209. One such example embodiment is shown as the cold pack machine 236 option 2.

In some embodiments the cold pack machine 235 includes a computer control unit 241, for controlling operating parameters of the cold pack machine 235 for producing a desired number of cold packs, at a desired temperature, at a desired point in time.

In some embodiments the computer control unit 241 provides commands to any one or more of the components of the cold pack machine 235 236 237.

FIG. 2A also shows an air cooler and blower 215 optionally blowing cold air 217 for cooling the packs 211 on the conveyor 213. In some embodiments the cold air 217 is collected and returned as air return 219 to the air cooler and blower 215.

In some embodiments the cold pack machine 235 includes the holding container 227. One such example embodiment is shown as the cold pack machine 237 option 3. In some embodiments the air cooler and blower 215 optionally serves to also refrigerate the holding container 227.

In some embodiments the holding container 227 optionally contains a refrigeration component (not shown) of its own, which optionally serves to refrigerate the holding container 227 in addition to, or instead of, the air cooler and blower 215.

In some embodiments the holding container 227 is detachable from the cold pack machine 235 236 237. In some embodiments the refrigeration component (not shown) of the holding container 227 optionally serves to refrigerate the holding container 227 when detached from the cold pack machine 235 236 237.

FIG. 2A also shows an optional data center 245 providing cold pack requests 247 to the controller 241 of the cold pack machine 235 236. In some embodiments the data center 245 is part of a center for packing packages for delivery, and the cold pack requests are provided for dispensing cold packs for inclusion into the packages.

FIG. 2A also shows an optional user interface 249 providing cold pack requests 251 and/or machine control commands 251 to the controller 241 of the cold pack machine 235 236. In some embodiments the user interface 249 enables a user to request cold packs from the cold pack machine 235 236, optionally a specific number of cold packs, at specific temperatures, and so on.

In some embodiments the cold pack machine 235 236 includes one or more of the user interface 249, the holding container 227 and the optional dispenser 224.

Figure 2B:
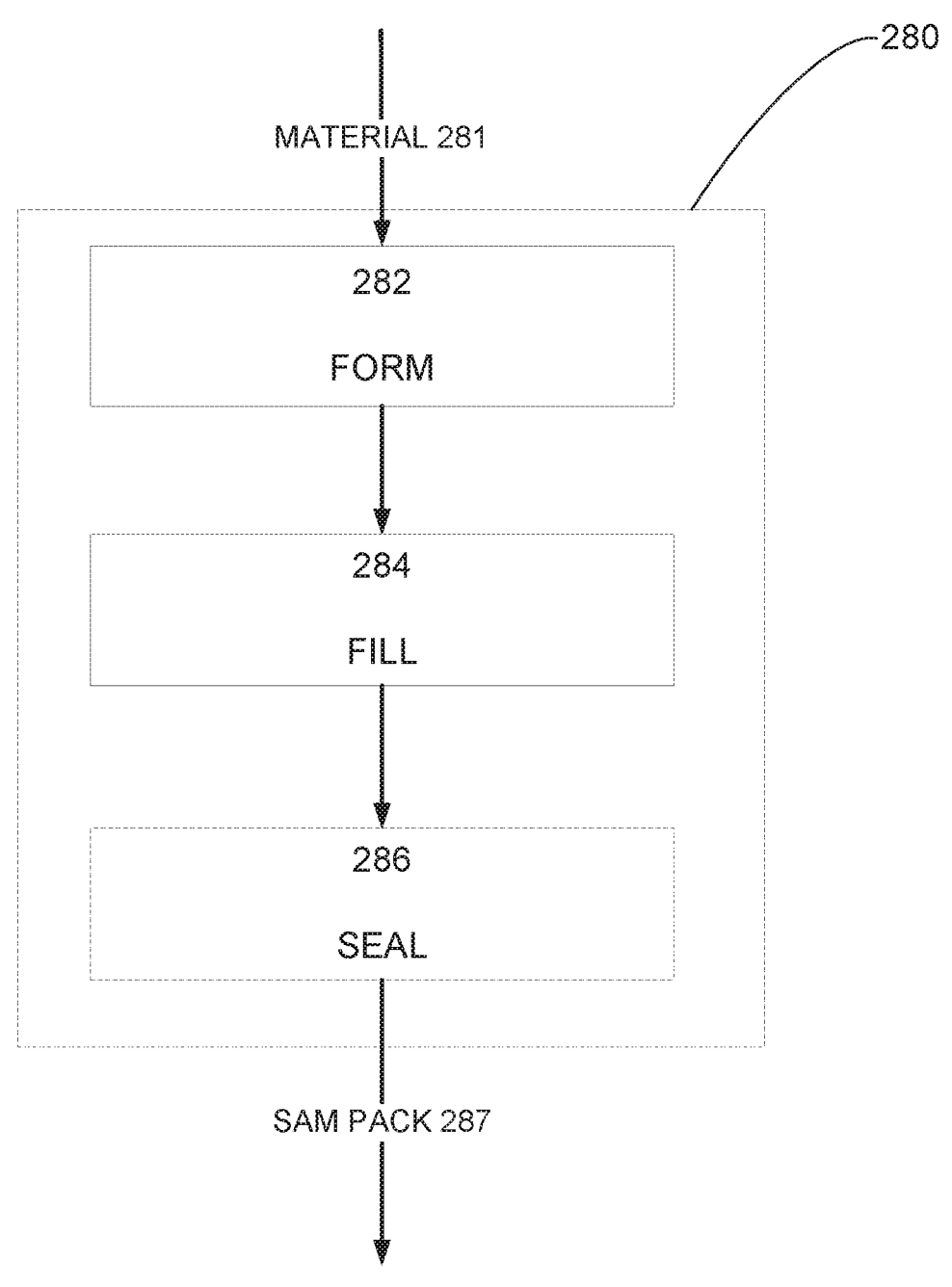
FIG. 2B is a simplified block diagram illustration of a system for producing a SAM pack according to an example embodiment of the invention.

Reference is now made to FIG. 2B, which is a simplified block diagram illustration of a system for producing a SAM pack according to an example embodiment of the invention.

FIG. 2B shows a system 280 which includes: An optional forming unit 282 for taking in material 281 for forming a bag or an envelope; a filling unit 284 for filling the bag with SAM, producing a SAM pack 287; and in some embodiments, an optional sealing unit 286.

The system 280 takes in input of material 281 such as, by way of a non-limiting example, plastic sheet, and produces output of a SAM pack 287.

In some embodiments the SAM pack 287 is constructed to be waterproof.

In some embodiments the material 281 is waterproof.

In some embodiments the SAM packs 287 are connected to each other, forming a strip of SAM packs 287. In some embodiments the strip of SAM packs 287 is provided as a roll of SAM packs 287. In some embodiments a length of the strip of SAM packs 287 is greater than 20 meters, optionally 40 meters, optionally 100 meters, optionally 1,000 meters, optionally 10,000 meters.

In some embodiments the strip of SAM packs 287 is provided as a fan-folded package of SAM packs 287. In some embodiments a box optionally includes 10,000 SAM packs sized 10×15 centimeters. In some embodiments 6 such boxes are packed on a pallet. In some embodiments 60,000 SAM packs are packed on a pallet.

In some embodiments the SAM pack 287 is heat sealed.

In some embodiments the SAM pack 287 is sealed using adhesive.

In some embodiments the SAM pack 287 is optionally not sealed.

In some embodiments the material 281 for forming the packs is a bag, such as a plastic bag, to be filled with SAM. In some embodiments the system 280 includes a forming unit 282 for optionally forming a bag from sheet material, and not forming a bag when the material 281 is already in a form of a bag.

In some embodiments the material is a tube, such as a plastic tube. Optionally, both open ends of the tube are sealed shut, by heating and/or by using adhesive to close the open ends.

In some embodiments an amount of SAM placed in the bag is optionally selected, to potentially provide SAM packs with different cooling power, based on an amount of SAM within a SAM pack, and using a same pack size.

In some embodiments the SAM placed in the bag is optionally SAM already packed in a cloth bag, and/or a mesh bag, and/or a woven bag, inserted into a waterproof bag.

Figure 2C:
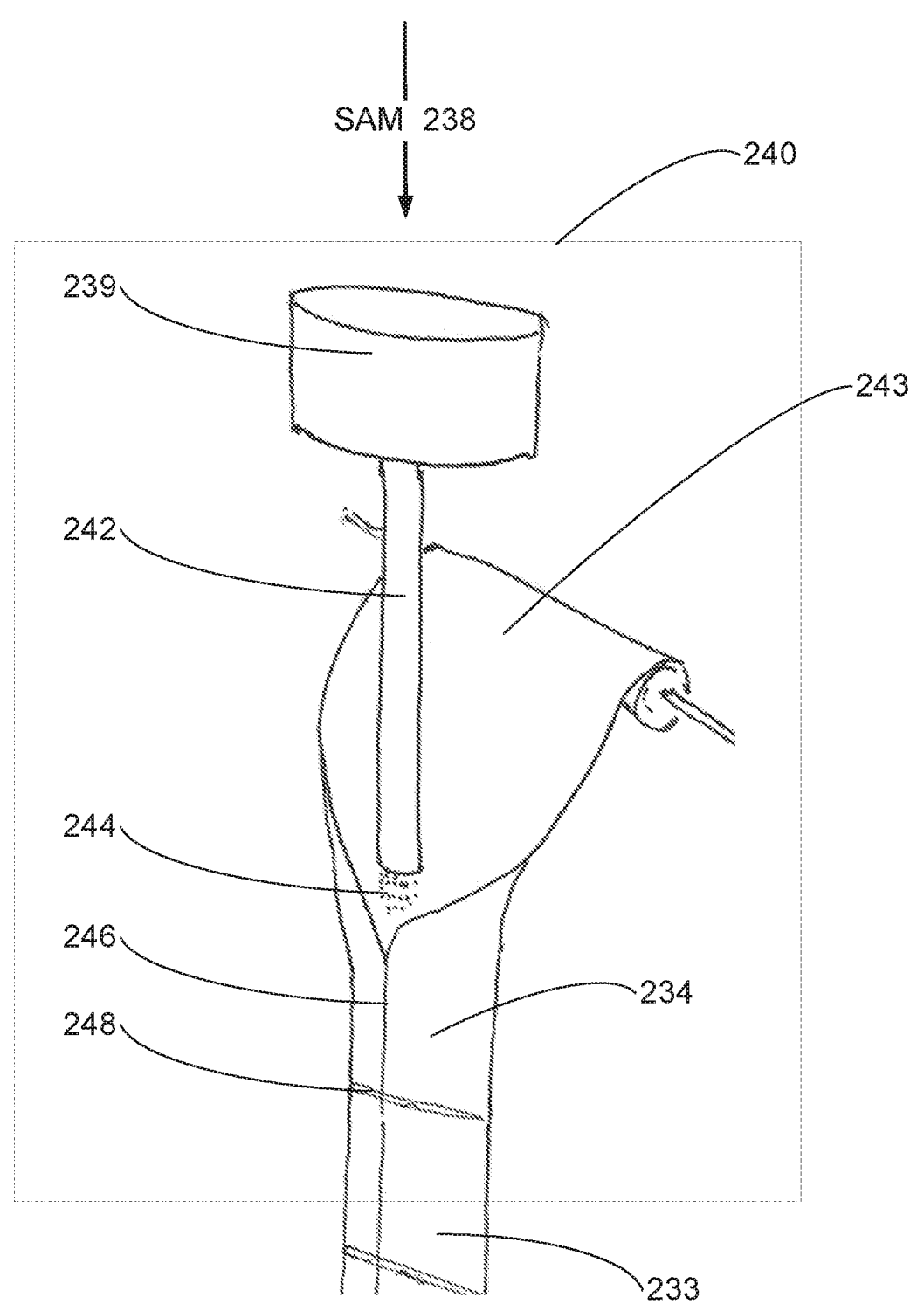
FIG. 2C is a simplified block diagram illustration of a system for producing a SAM pack according to an example embodiment of the invention.

Reference is now made to FIG. 2C, which is a simplified block diagram illustration of a system for producing a SAM pack according to an example embodiment of the invention.

FIG. 2C shows a system 240 which includes:

a hopper 239, which can take in SAM 238 and dispense SAM 244;

a source of material 243 for forming a pack, such as, by way of a non-limiting example, a roll of sheet material; and a spout 242 for guiding the SAM 244 into the material 243.

In some embodiments the system 240 is a Form Fill and Seal machine.

The system 240 optionally forms the material 243 into a tube 234, and seals a seam 246 along a length of the tube 234.

The system 240 optionally fills the tube 234 with SAM 244 in a desired amount, optionally using a dispenser (not shown), and seals 248 across the tube 234 to produce SAM packs 233.

Figure 2D:
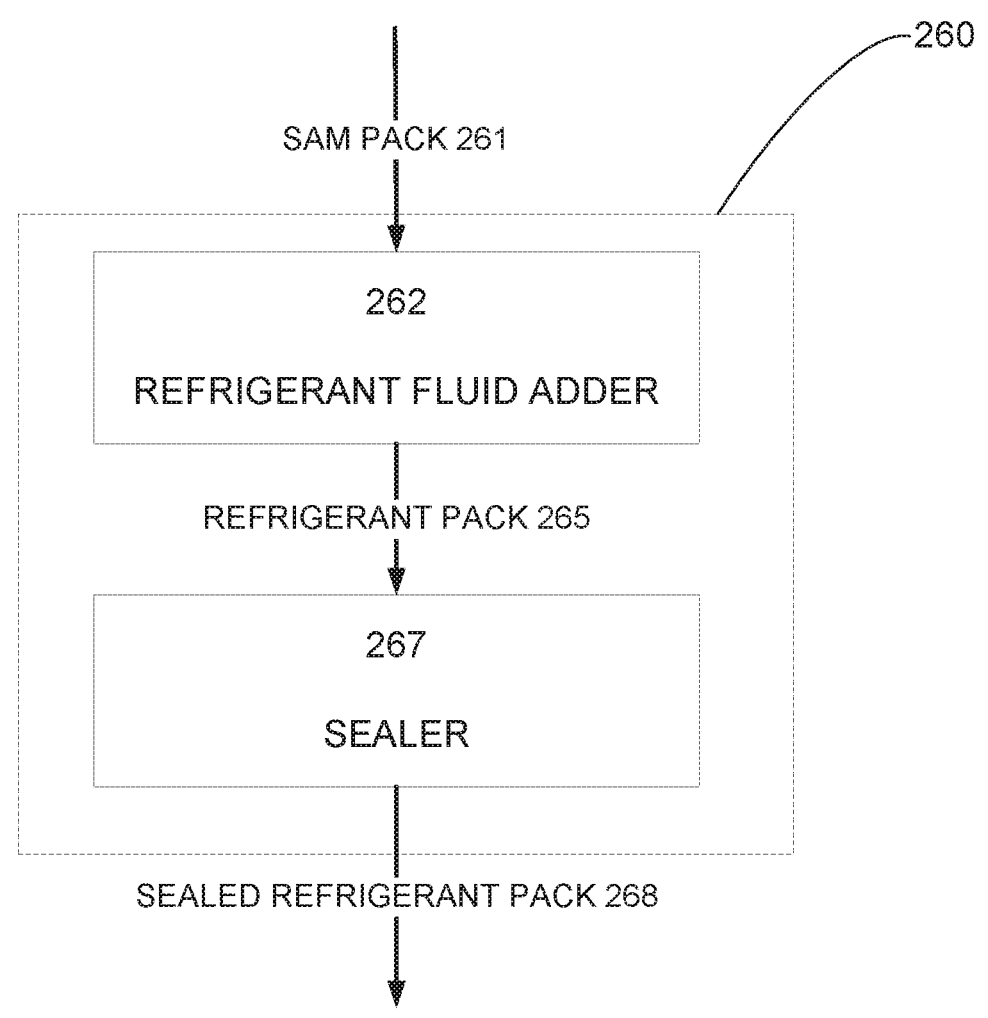
FIG. 2D is a simplified block diagram illustration of a system for dispensing a refrigerant pack according to an example embodiment of the invention.

Reference is now made to FIG. 2D, which is a simplified block diagram illustration of a system for dispensing a refrigerant pack according to an example embodiment of the invention.

FIG. 2D shows a system 260 which includes:

a filling unit 262 for taking in a SAM pack 261 with SAM inside and without refrigerant fluid inside and adding refrigerant fluid to an inside of the SAM pack 261, producing a refrigerant pack 265; and an optional sealing unit 267 for optionally sealing the refrigerant pack 265, producing a sealed refrigerant pack 268 for dispensing and/or storing.

In some embodiments the refrigerant pack 265 is optionally not sealed.

In some embodiments the system 260 does not includes a sealer 267.

Figure 2E:
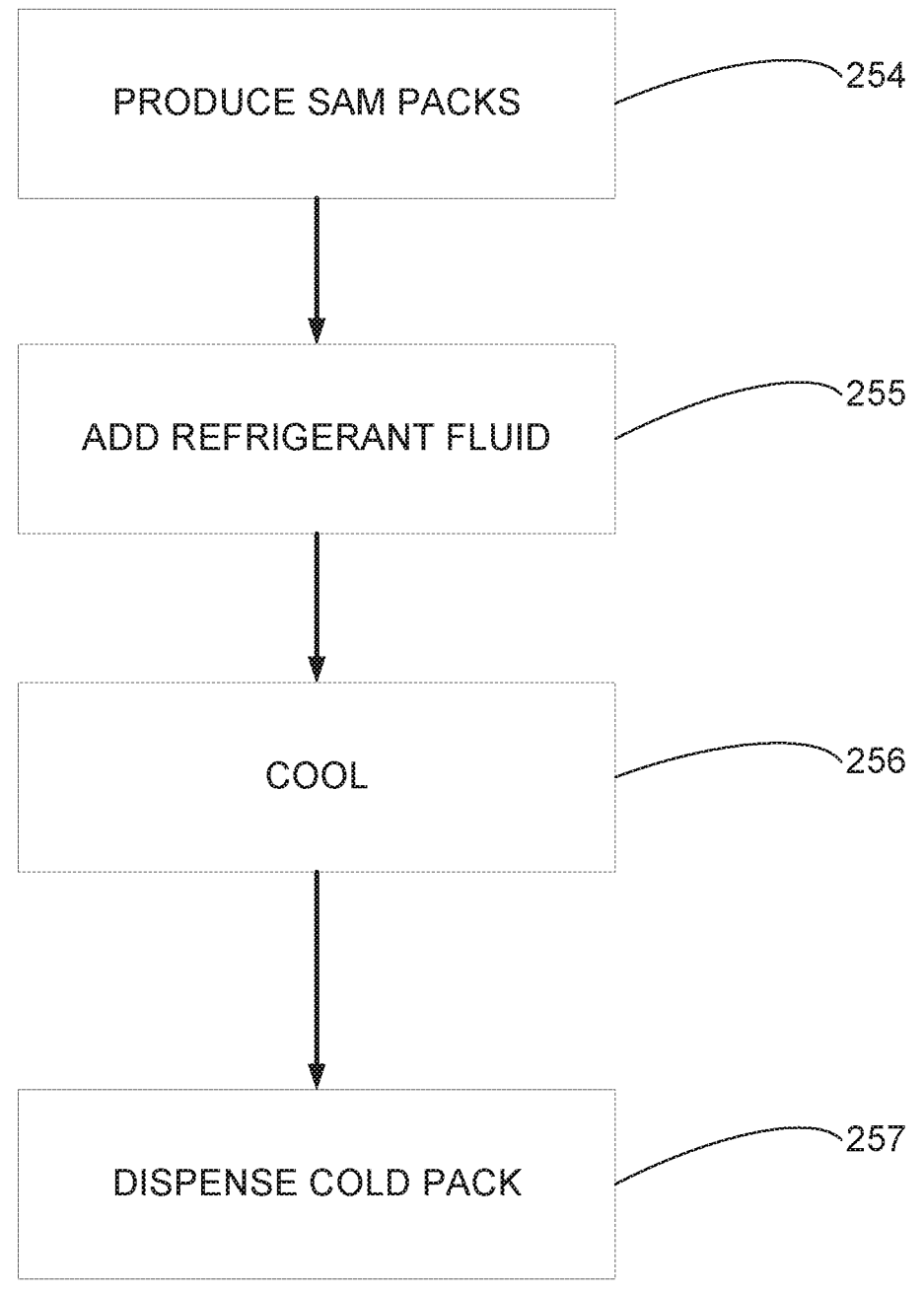
FIG. 2E is a simplified flow chart illustration of a process for producing SAM packs and dispensing cold packs, according to an example embodiment of the invention.

Reference is now made to FIG. 2E, which is a simplified flow chart illustration of a process for producing SAM packs and dispensing cold packs, according to an example embodiment of the invention.

FIG. 2E shows a method which includes:

producing SAM packs (254). In some embodiments bags, such as plastic bags, are filled with SAM, producing a SAM pack. In some embodiments a tube, such as a plastic tube, is filled with SAM, producing a SAM pack. Optionally, both open ends of the tube are sealed shut, by heating and/or by using adhesive to close the open ends;

adding refrigerant fluid 255. In some embodiments the refrigerant fluid is injected into a sealed SAM pack. In some embodiments the pack, now including both SAM and refrigerant fluid, are sealed, or re-sealed;

cooling the packs 256. In some embodiments the packs are cooled, or frozen, to s desired temperatures. Optionally the packs are frozen to a cold temperature such as 4, 0, −4, −5, −18, −35, −40 degrees Celsius and even −75 degrees Celsius; and dispensing cold packs 257. In some embodiments the dispensing may be by a dispensing chute. In some embodiments the dispensing may be in response to a computer control command.

In some embodiments the adding refrigerant fluid is performed at a goods packing site.

In some embodiments the SAM packs are optionally produced as strips or chains of connected SAM packs. In some embodiments the SAM packs are optionally produced from a tube, and the tube is sealed at ends of the SAM packs, producing a strip or chain of connected SAM packs.

In some embodiments a strip or chain of SAM packs is packaged in a box. In some embodiments a strip or chain of SAM packs is packaged in a box in a fan-folded fashion, layer upon layer. In some embodiments a strip or chain of SAM packs is packaged in a roll.

In some embodiments the SAM packs are a product which is shipped to users/clients. Shipping SAM packs takes up less weight and less volume than shipping cold packs which includes refrigerant fluid within each cold pack, and require only adding refrigerant fluid, even such as water, to become cold packs. The refrigerant fluid can weigh a large portion of a weight of the cold pack, and such weight is saved in SAM packs.

In some embodiments a SAM pack, or a strip of SAM packs, is optionally fed into a refrigerant injection machine. In some embodiments the refrigerant fluid is injected into an end, a side, or a face of a SAM pack. In some embodiments the refrigerant fluid is injected into the SAM pack by puncturing the SAM pack, optionally puncturing with a syringe for injection the refrigerant fluid into the SAM pack. In some embodiments the injection machine optionally also seals an opening through which the refrigerant fluid was injected. In some embodiments a component other than the injection machine optionally does the sealing of the opening through which the refrigerant fluid was injected.

In some embodiments the strip of SAM packs is kept as a connected strip during the adding of refrigerant fluid. In some embodiments the strip of SAM packs is separated into separate packs by a same machine performing the adding of refrigerant fluid. In some embodiments the strip of SAM packs is separated into separate packs by a same machine performing the sealing or re-sealing of the packs.

In some embodiments the cooling is performed in a refrigeration machine. In some embodiments the packs are loaded onto a conveyor belt going through a refrigeration machine.

In some embodiments a strip of packs is separated into separate packs upon entry into the refrigeration machine and/or upon placing onto the conveyor.

In some embodiments a strip of packs is separated into separate packs after a cooling, being separated when they are already cold packs.

In some embodiments the conveyor is a conveyor travelling in a helical path, potentially reducing a footprint of the refrigeration machine.

In some embodiments the conveyor is a conveyor travelling up in a helical path. In some embodiments an upward portion of the conveyor is optionally above a second conveyor, and is optionally used to dispense cold packs from above the second conveyor, optionally into a box on the second conveyor. In some embodiments an upward portion of the conveyor is optionally straight, optionally to convey above a second conveyor or above a storage container for the cold packs.

In some embodiments the conveyor is a conveyor travelling down in a helical path.

In some embodiments the cooling is performed by cold air enveloping the packs. In some embodiments a temperature of the air is optionally controllable, for example in a range between 0 and −40 degrees Celsius.

In some embodiments the refrigeration machine can accommodate different sized packs, such as, by way of some non-limiting example, 16 oz., 32 oz. and 64 oz.

In some embodiments a pack reaching an end of the conveyor is dispensed, optionally via a dispensing chute.

In some embodiments a pack reaching an end of the conveyor is optionally conveyed to a storage chamber for cold packs. In some embodiments the storage chamber is used to collect cold packs. In some embodiments cold packs are dispensed from the storage chamber when there is a demand for a cold pack, and if there is a cold pack in the storage chamber.

In some embodiments when a pack reaches an end of the conveyor, and there is no un-filled request for a cold pack, the conveyor is stopped.

In some embodiments the dispensing of cold packs is under computer control. In some embodiments the dispensing of cold packs is by a user entering a number of desired cold packs to a user interface. In some embodiments a data center controls requests for package shipments, and calculates and/or controls a number of cold packs to be dispensed.

Figure 2F:
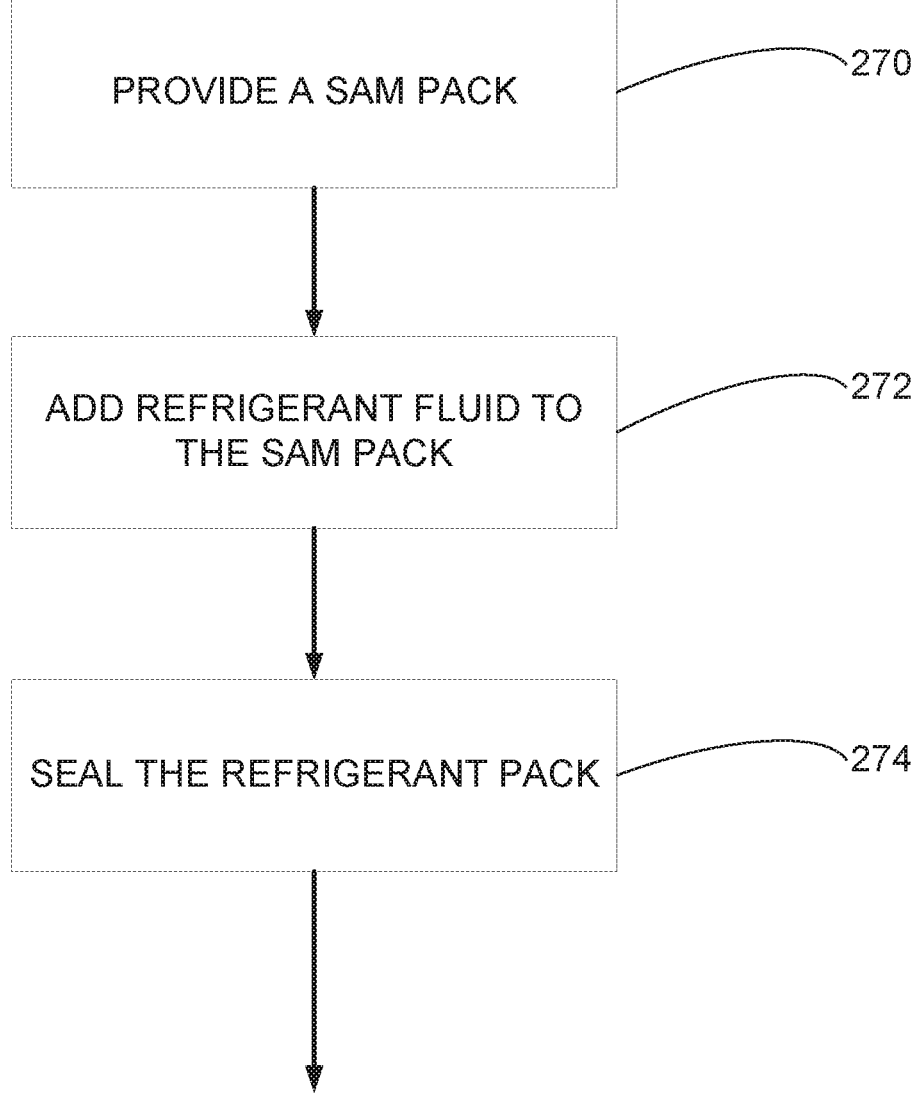
FIG. 2F is a simplified flow chart illustration of a process for providing a refrigerant pack according to an example embodiment of the invention.

Reference is now made to FIG. 2F, which is a simplified flow chart illustration of a process for providing a refrigerant pack according to an example embodiment of the invention.

FIG. 2F shows a method which includes:

providing a SAM pack with SAM inside and without refrigerant fluid inside (270);

adding refrigerant fluid to an inside of the SAM pack, thereby producing a refrigerant pack (272); and optionally sealing the refrigerant pack (274).

In some embodiments, the refrigerant pack is not sealed.

An Example Embodiment of Two-Stage Pack Production and Distribution

In some embodiments, cold packs are made in two stages. In a first stage, plastic bags are filled with SAM, producing SAM packs, and shipped to a user. A second stage is performed at the user's site, where a machine makes cold packs out of the SAM packs. This is done by adding water to the SAM packs and cooling and/or freezing the packs. Since volume and weight of SAM packs with SAM only is significantly lower than fluid-filled cold packs, shipping, handling and storing costs are also significantly lower.

An Example Embodiment of Producing SAM Packs

In some embodiments SAM packs are made in a process called FFS, Form Fill and Seal. A sheet of plastic such as polyethylene, optionally from a roll of polyethylene sheet, is fed into a machine which makes packs, sacs or bags, fills SAM in each pack, producing SAM packs, and optionally seals the SAM pack. In some embodiments a thickness of the plastic sheet may vary between 80-300 microns.

In some embodiments the SAM packs are connected to each other in a chain with or without perforation between consecutive SAM packs. A chain may include from 2 SAM packs up to 1,200-1,800 SAM packs. The FFS machine optionally packages each chain in a box, optionally fan-folded, layer upon layer, or as a roll. The SAM packs can be conveniently packaged in a roll because they are not as thick as cold packs which have refrigerant fluid inside.

A wide range of SAM pack dimensions is made, to cover common sizes on the market. A typical width of a SAM pack may be 80-160 mm and a typical length may be 100-300 mm. In some embodiments a quantity of SAM per SAM pack is optionally determined by the pack size and by the pack's intended application, and is typically 1.0-2.0% of the weight of the bag after it is filled with water.

In some embodiments a quantity of SAM per SAM pack is optionally determined by the pack size and by the pack's intended application, and is typically 5-10 grams of SAP per 500 cc water.

In some embodiments data about SAM pack size, SAM amount, perforation between chains and number of SAM packs in a chain is optionally fed into a FFS machine for the manufacturing process. Feeding in the data is done either manually or by a computerized system.

Storing SAM Packs

In some embodiments boxes with SAM packs or chains of SAM packs are optionally arranged on pallets and stored until delivered. A pallet may contain 5,000 to 100,000 and even to 250,000 SAM packs and more.

Shipping SAM Packs to Users

In some embodiments pallets of boxes containing SAM packs or chains of SAM packs are delivered to users upon request or according to a predetermined schedule.

Making Cold Packs

In some embodiments, SAM packs or chains of SAM packs are optionally fed into a refrigerant filling machine at the user's site, which injects refrigerant fluid such as water into the SAM packs. In some embodiments the same machine, in some embodiments an additional machine, cools and/or freezes the packs, making cold packs. In some embodiments the cooling is to a temperature between +5° Celsius and −40° Celsius. In some embodiments the amount of water per cold pack may be in a range of 300-1,200 cc per pack.

In some embodiments a quantity of refrigerant fluid per SAM pack is optionally determined by the pack size, manually set up or by a machine reading a barcode on the SAM pack.

In some embodiments each pack is separated from a chain prior to being cooled. The cold packs can potentially be used in shipment of goods that require refrigeration.

Figure 2G:
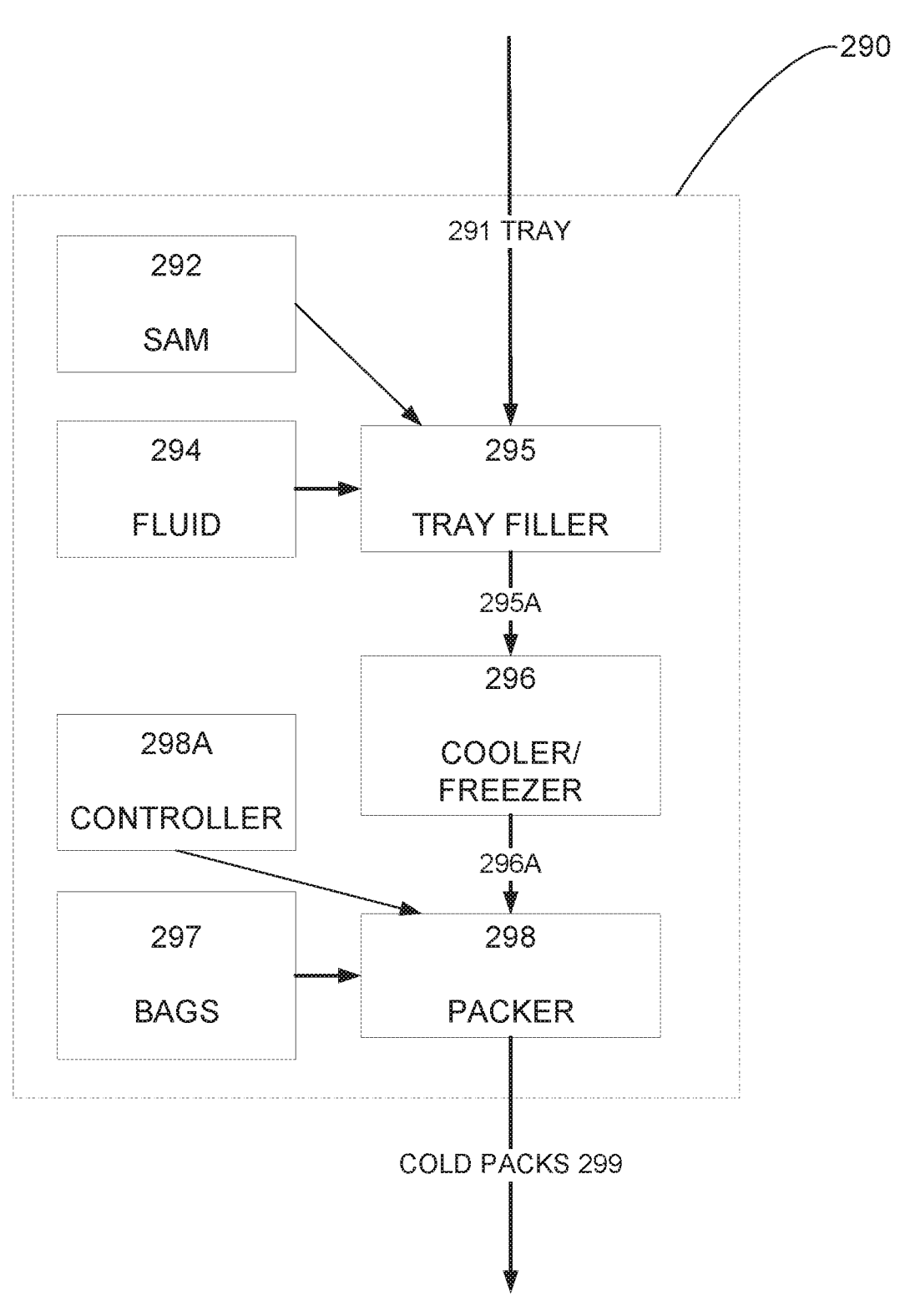
FIG. 2G is a simplified block diagram illustration of a system for producing a cold pack according to an example embodiment of the invention.

Reference is now made to FIG. 2G, which is a simplified block diagram illustration of a system for producing a cold pack according to an example embodiment of the invention.

FIG. 2G shows a system 290 which includes:

a tray filler component 295 for taking in a tray 291 and filling the tray 291 with a mixture of SAM from a SAM supplying component 292, and refrigerant fluid from a refrigerant fluid source 294. In some embodiments the tray 291 includes depressions and the depressions are filled with the mixture;

a cooling/freezing component 296, for taking in the tray 295A and refrigerating the mixture in the tray, producing a tray 296A containing a cold and/or frozen SAM plus fluid mixture; and a packing component 298 for receiving and/or manufacturing packs or bags from a pack or bag source 297 and transferring the cold and/or frozen mixture into the packs or bags, producing cold packs 299.

In some embodiments the system 290 also includes a mixer (not shown) for mixing the SAM from the SAM supplying component 292 and the refrigerant fluid from the refrigerant fluid source 294 before filling the mixture into the tray 291.

In some embodiments the tray travels through the system 290 on a conveyor belt.

In some embodiments the tray 291 includes compartments such as a home refrigerator ice tray.

In some embodiments the tray 291 includes depressions in specific shapes, such as, by way of some non-limiting examples: cubic, rectangular, oval, spherical.

In some embodiments the tray 296A containing the cold and/or frozen mixture contains the mixture frozen solid. In some embodiments the tray 296A containing the cold and/or frozen mixture contains the mixture as a cold slush or gel.

In some embodiments the mixture is optionally frozen to the specific shape which, after packing in a bag, produces a bag with accurate dimensions as determined by the tray cell dimensions.

In some embodiments the bag source 297 provides different size bags or packs, optionally based on receiving an electronic request for the different size bags or packs, and the system 290 provides cold packs in a variety of sizes.

In some embodiments the packing component 298 is set up to pack a desired amount of cold and/or frozen mixture into the bags or packs, optionally based on receiving an electronic request for the desired amount and/or a request for different size bags or packs.

In some embodiments the packing component 298 seals the cold packs 299.

In some embodiments the packing component 298 is a Form Fill and Seal component.

In some embodiments a controller 298A controls operation of the packing component 298.

In some embodiments the packing component 298 does not seal the cold packs 299. In some embodiments the system 290 includes an additional optional sealer for sealing the cold packs 299.

In some embodiments the bag source 297 and the packing component 298 are in a separate machine from the other components described above with reference to the system 290.

In some embodiments the bag source 297 and the packing component 298 are optionally as described with reference to FIGS. 2B and 2C.

In some embodiments the packs are provided as a connected series or strip of packs, and the packs are separated prior to filling with the cold and/or frozen mixture.

In some embodiments the packs are provided as a connected series or strip of packs and the packs are separated after filling with the cold and/or frozen mixture.

In some embodiments the packs are provided as a connected series or strip of packs and not separated after filling with the cold and/or frozen mixture.

In some embodiments the packs are provided as separate packs packaged next to each other similarly to envelopes in a package of envelopes.

Figure 2H:
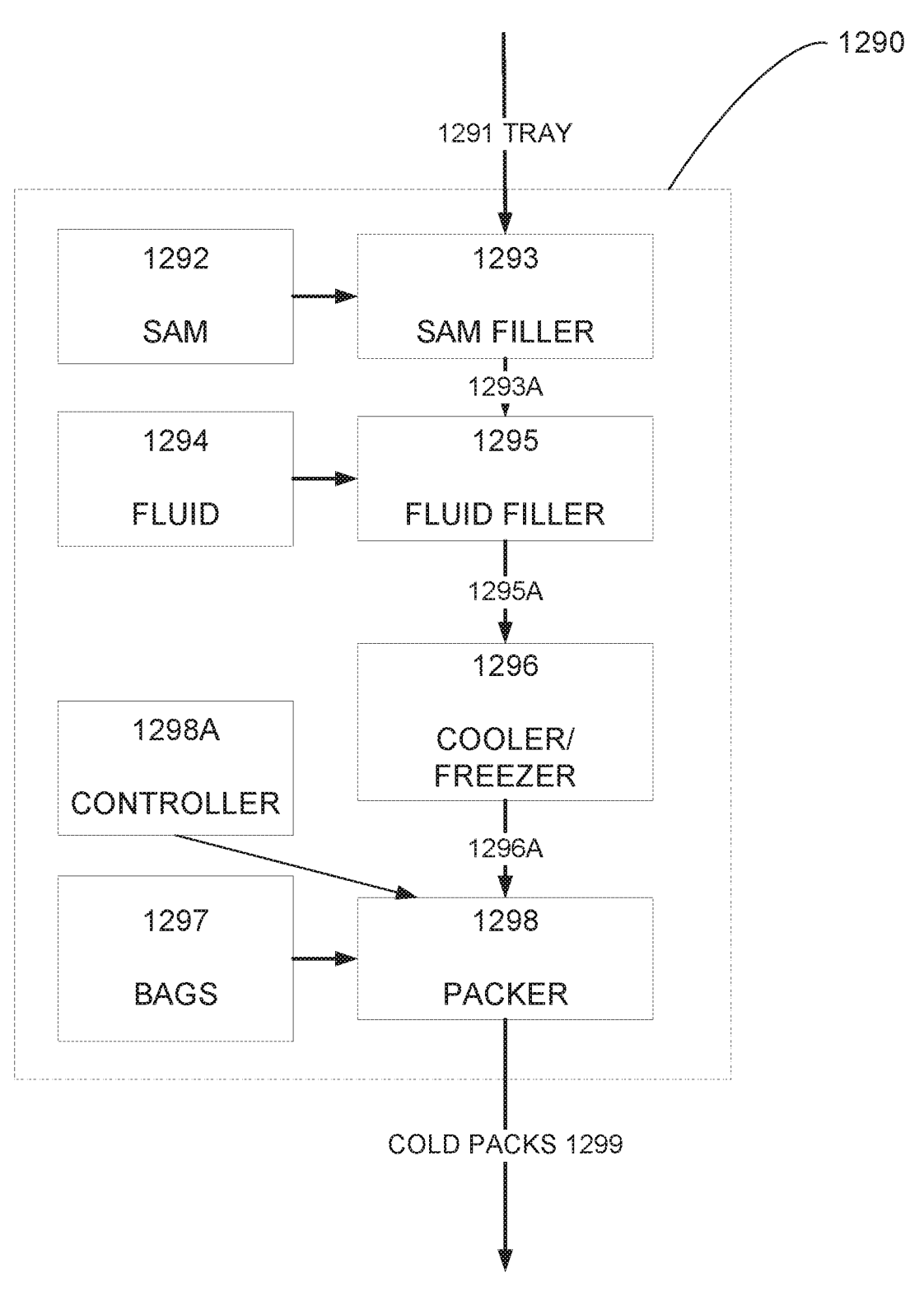
FIG. 2H is a simplified block diagram illustration of a system for producing a cold pack according to an example embodiment of the invention.

Reference is now made to FIG. 2H, which is a simplified block diagram illustration of a system for producing a cold pack according to an example embodiment of the invention.

FIG. 2H shows a system 1290 which includes:

a SAM filler component 1293 for taking in a tray 1291 and filling the tray 1291 with SAM from a SAM supplying component 1292, producing a tray with SAM 1293A. In some embodiments the tray 1291 includes depressions and the depressions are filled with the SAM;

a fluid filling component 1295, for adding refrigerant fluid from a refrigerant fluid source 1294 to a SAM-filled tray 1293A, producing a SAM-plus-refrigerant-fluid filled tray 1295A;

a cooling/freezing component 1296, for taking in the tray 1295A and refrigerating the SAM and refrigerant fluid in the tray, producing a tray 1296A containing cold and/or frozen SAM plus fluid material; and a packing component 1298 for receiving and/or manufacturing packs or bags from a pack or bag source 1297 and transferring the cold and/or frozen SAM plus fluid material into the packs or bags, producing cold packs 1299.

In some embodiments the tray travels through the system 1290 on a conveyor belt.

In some embodiments the tray 1291 includes compartments such as a home refrigerator ice tray.

In some embodiments the tray 1291 includes depressions in specific shapes, such as, by way of some non-limiting examples: cubic, rectangular, oval, spherical.

In some embodiments the material in the SAM-plus-refrigerant-fluid filled tray 1295A is mixed by a mixing component (not shown) before refrigerating.

In some embodiments the tray 1296A containing cold and/or frozen SAM plus fluid material contains material frozen solid. In some embodiments the tray 1296A containing cold and/or frozen SAM plus fluid material contains material as a cold slush.

In some embodiments the bag source 1297 provides different size bags or packs, optionally based on receiving an electronic request for the different size bags or packs, and the system 1291 provides cold packs in a variety of sizes.

In some embodiments the packing component 1298 is set up to pack a desired amount of cold and/or frozen SAM plus fluid material into the bags or packs, optionally based on receiving an electronic request for the desired amount and/or a request for different size bags or packs.

In some embodiments the packing component 1298 seals the cold packs 1299.

In some embodiments the packing component 1298 is a Form Fill and Seal component.

In some embodiments a controller 1298A controls operation of the packing component 1298.

In some embodiments the packing component 1298 does not seal the cold packs 1299. In some embodiments the system 1290 includes an additional optional sealer for sealing the cold packs 1299.

In some embodiments the bag source 1297 and the packing component 1298 are in a separate machine from the other components described above with reference to the system 1290.

In some embodiments the bag source 1297 and the packing component 1298 are optionally as described with reference to FIGS. 2B and 2C.

In some embodiments the packs are provided as a connected series or strip of packs, and the packs are separated prior to filling with the cold and/or frozen SAM plus fluid material. In some embodiments the packs are provided as a connected series or strip of packs and the packs are separated after filling with the cold and/or frozen SAM plus fluid material.

In some embodiments the packs are provided as a connected series or strip of packs and not separated after filling with the cold and/or frozen SAM plus fluid material.

Referring again to FIGS. 2G and 2I—in some embodiments the machines 290 1290 optionally receive a refrigerant pack, that is a SAM pack which also contains a refrigerant fluid, or a water-filled pack, and places the incoming pack(s) in a tray 291 1291. In some embodiments a manipulator picks up an incoming pack and places the pack in a cell in the tray 291 1291. In some embodiments the refrigerant pack is optionally shaped by the cell to any of the shapes listed above. a potential benefit of some embodiments includes forming cold packs which have a shape of the tray cells, potentially being formed with more accurate geometric dimensions than packs cooled or frozen without tray cell walls shaping them.

In some embodiments the packs are shaped by a shape of the tray cell, optionally as a rectangular or brick shape.

In some embodiments the tray is optionally interchangeable, enabling changing between different tray cell sizes and/or shapes.

Figure 2I:
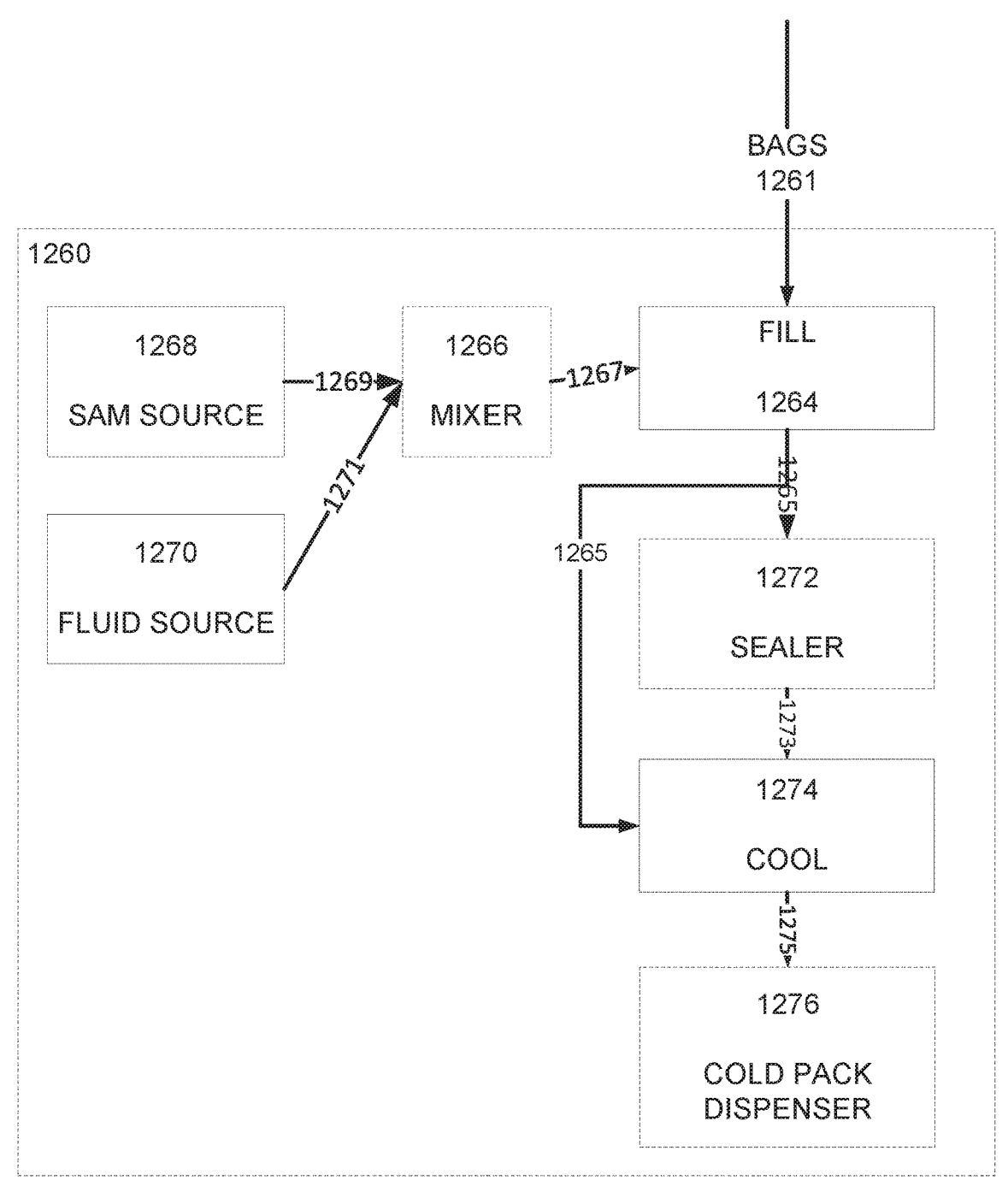
FIG. 2I is a simplified block diagram illustration of a system for taking in an empty bag and producing a cold pack according to an example embodiment of the invention.

Reference is now made to FIG. 2I, which is a simplified block diagram illustration of a system for taking in an empty bag and producing a cold pack according to an example embodiment of the invention.

FIG. 2I shows a system 1260 which includes:

a SAM source 1268;

a refrigerant fluid source 1270;

an optional mixer 1266, which takes in SAM 1269 from the SAM source 1268 and refrigerant fluid 1271 from the refrigerant fluid source 1270 and produces a mixture 1267 of SAM and refrigerant fluid, optionally by mixing the SAM and the refrigerant fluid;

a fill component 1264 for taking in an empty bag or strip of bags 1261 and filling the bags 1261 with the mixture 1267, producing a refrigerant pack 1265;

an optional sealer 1272 for sealing the refrigerant pack 1265, producing a sealed refrigerant pack 1273;

a cooler 1274, for accepting a refrigerant pack 1265 or a sealed refrigerant pack 1273, and cooling the packs, and producing a cold pack 1275; and an optional cold pack dispenser 1276.

In some embodiments the fill component 1264 optionally accepts different size bags or packs, optionally based on receiving an electronic request for the different size bags or packs, and the system 1260 provides cold packs in a variety of sizes.

In some embodiments the fill component 1264 is optionally set up to pack a desired amount of cold and/or frozen mixture into the bags or packs, optionally based on receiving an electronic request for the desired amount and/or a request for different size bags or packs.

In some embodiments the fill component 1264 and the packing component 298 are a Form Fill and Seal component.

In some embodiments a controller (not shown) controls operation of the system 1260.

In some embodiments the packs are provided as a connected series or strip of packs, and the packs are separated prior to filling with the cold and/or frozen mixture.

In some embodiments the packs are provided as a connected series or strip of packs and the packs are separated after filling with the cold and/or frozen mixture.

In some embodiments the packs are provided as a connected series or strip of packs and not separated after filling with the cold and/or frozen mixture.

Making Cold Packs at Different Temperatures

In some embodiments, cold pack batches are cooled to different temperatures. In some embodiments a first batch of cold packs is cooled to a first specific temperature, and optionally stored in a first holding unit or temperature controlled or insulated storage unit, and a second batch of cold packs is cooled to a second specific temperature, and optionally stored in a second holding unit or temperature controlled or insulated storage unit, or cold pack machine.

Warehouse Operation

Reference is now made to FIG. 3A, which is a simplified block diagram illustration of warehouse operation according to prior art.

FIG. 3A shows a warehouse 301 for shipping packages 308, at least some of which require addition of cold packs in order to maintain cold in the packages 308.

The warehouse 301 includes an unloading dock 309A, a goods storage area 302, a cold pack freezer 303, and one or more conveyors 305 for packing some mixture of goods and cold packs, for shipping from a loading dock 309B.

Trucks 306 unload goods 311 for storing at the goods storage area 302, and trucks 307 unload pallets 304 of cold packs for storing 312 in the cold pack freezer 303.

It is noted that some of the goods require cold storage, and may be stored in refrigerators or freezers.

Warehouse operators or conveyors (not shown) take goods 313 from the goods storage area 302 to the conveyors 305, and warehouse operators or conveyors (not shown) take 314 cold pack palettes 304 from the cold pack freezer 303 to use for packaging the goods 313 with cold packs. The packaged goods are then shipped by truck 309. Typically, a pallet 304 of 640 cold packs is placed next to the conveyors 305. Providing such a pallet 304 from the cold pack freezer 303 takes approximately 10-15 minutes, and is typically performed manually 12-15 times per day.

An embodiment of the invention potentially improves a layout and process flow of such a warehouse and shipping facility.

The inventors point out some typical issues with reference to the prior art warehouse shown in FIG. 3A.

Unloading a truck at the unloading dock 309A typically takes approximately an hour. Bringing in SAM packs instead of cold packs can reduce the volume and weight and numbers of trucks coming in, for a same amount of goods shipped, saving time and salary for the unloading. A number of empty cold pack boxes is greater than a number of empty SAM pack boxes.

The cold pack freezer 303 takes up a large floor area. In a typical prior art warehouse 55 pallets of cold packs include 2,200 cases of cold packs, which include 35,200 cold packs. A cold pack typically stays 2 weeks on the average in the freezer 303. The cold pack freezer requires power to refrigerate the cold packs, which arrived frozen/cold from a supplier of cold packs, and must be kept cold. Keeping a similar amount of SAM packs takes up less warehouse floor space and does not require refrigeration. By way of a non-limiting example, ½ a pallet of SAM packs has a same number of SAM packs as 55 pallets of prior art cold packs of a similar size and/or cooling capacity. Refrigeration can optionally be used on-demand, to cool or freeze cold packs in the amount needed, without refrigerating a large number of cold packs for a long duration.

Figure 3B:
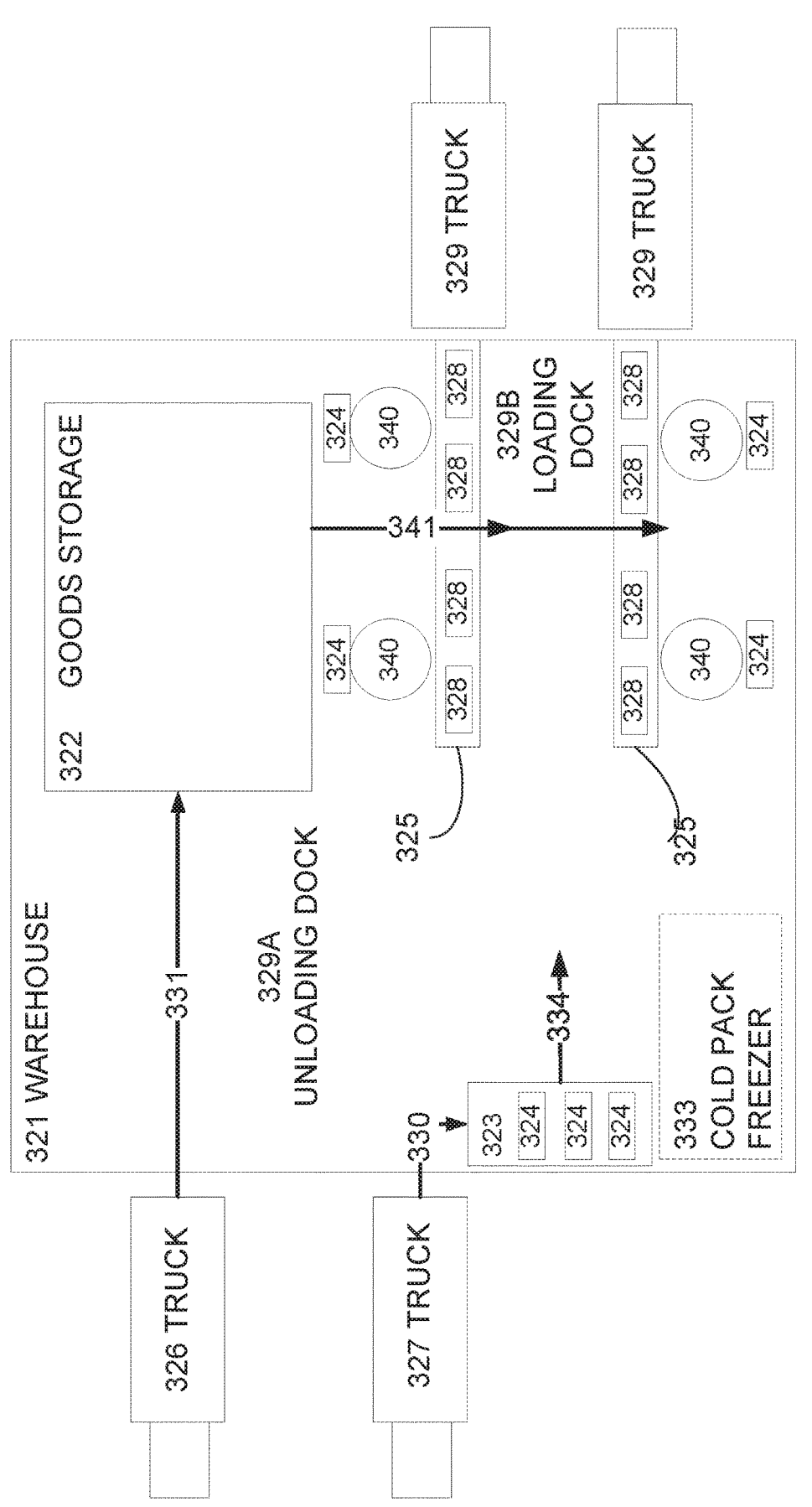
FIG. 3B is a simplified block diagram illustration of warehouse operation according to an example embodiment of the invention.

Reference is now made to FIG. 3B, which is a simplified block diagram illustration of warehouse operation according to an example embodiment of the invention.

FIG. 3B shows a warehouse 321 for shipping packages 328, at least some of which require addition of cold packs in order to maintain cold in the packages 328.

The warehouse 321 includes an unloading dock 329A, a goods storage area 322, a SAM pack storage area 323, and one or more conveyors 325 for packing some mixture of goods and cold packs, for shipping from a loading dock 329B.

Trucks 326 unload goods 331 for storing at the goods storage area 322, and trucks 327 unload pallets 324 of SAM packs for storing 330 in the SAM pack storage area 323.

It is noted that some of the goods require cold storage, and may be stored in refrigerators or freezers.

Warehouse operators or conveyors (not shown) take goods 341 from the goods storage area 322 to the packing lines and/or conveyors 325, and warehouse operators or conveyors (not shown) take 334 SAM pack pallets 324 from the SAM pack storage area 323 and place near one or more cold pack machines 340.

The cold pack machines 340 optionally provide cold packs near the conveyors 325. The cold pack machines 340 optionally provide as many cold packs as are needed, optionally fulfilling computerized requests from a system which controls goods supply and/or from a user interface operated by warehouse operators working at the conveyors 325. At an end of the packing lines or conveyors 325 goods and optionally cold packs have been packaged, optionally for shipping by truck 329.

In some embodiments providing such a pallet 324 from the SAM pack storage area 323 is typically performed less than providing a pallet of cold packs 304 of FIG. 3A, since the same number of SAM packs takes up much less volume and weight than cold packs, so a pallet 324 of SAM packs can contain many more packs than a pallet 304 of cold packs.

As mentioned above with reference to FIG. 3A, a typical prior art pallet 304 contains about 640 cold packs, while a pallet of SAM packs may contain 5,000 to 100,000 SAM packs.

The cold pack machines 340 optionally receive a strip of SAM packs, inject the SAM packs with refrigerant fluid such as water, cool or freeze the packs, and provide cold packs for packing with the goods.

Some benefits of the configuration of FIG. 3B over the configuration of FIG. 3A are listed below.

Smaller trucks 327 may be used for providing the SAM packs, and/or same size trucks may be unloaded less often.

Shipping a truckload of prior art cold packs may cost $1,500 to ship a distance of a day's drive. Such a cost potentially needs to be incurred far less, since a same volume and/or weight of shipping contains many times more SAM packs than prior art refrigerant packs or cold packs.

An area of the SAM pack storage area 323 is significantly smaller than an area of the cold pack freezer 303. The SAM pack storage area may optionally use up an area of a few pallets, each pallet 48 inches by 48 inches, or 4 square feet. The floor space of the cold pack machine 340 is optionally approximately 40 square feet. A typical cold pack freezer 303 of FIG. 3A can be as little as 3,000 cubic feet, taking up a floor space of more than 300 square feet, up to 40,000 cubic feet, taking up more than 4000 square feet.

The SAM pack storage area 323 requires no refrigeration, saving power.

A savings in labor is potentially achieved, with providing a pallet 304 from the cold pack freezer 303 taking approximately 10-15 minutes, typically performed manually 12-15 times per day, while for the same amount of cold packs, a single pallet can be provided once a day or less.

In some embodiments, the warehouse 321 optionally includes a cold pack freezer 333. It is noted that the cold pack freezer 333 is not necessary in all embodiments since cold packs are produced in the cold pack machine(s) 340, and cold packs may be stored in cold pack machines 340 or in optional holding container included in the cold pack machines 340 or detachable from the cold pack machines 340. The cold pack freezer 333 may optionally contain cold packs left over and not used, optionally keeping the cold packs cold. In some embodiments the cold pack freezer 333 optionally serves to store cold packs at a first temperature when cold packs are being cooled by cold pack machines 340 to a second, different temperature.

In some embodiments the cold pack freezer 333 used for serving the warehouse 321 is significantly smaller than the cold pack freezer 303 used for a prior art warehouse 301.

In some embodiments it is sufficient to provide 1 truck per month of SAM packs instead of one truck per day of prior art cold packs.

Figure 3C:
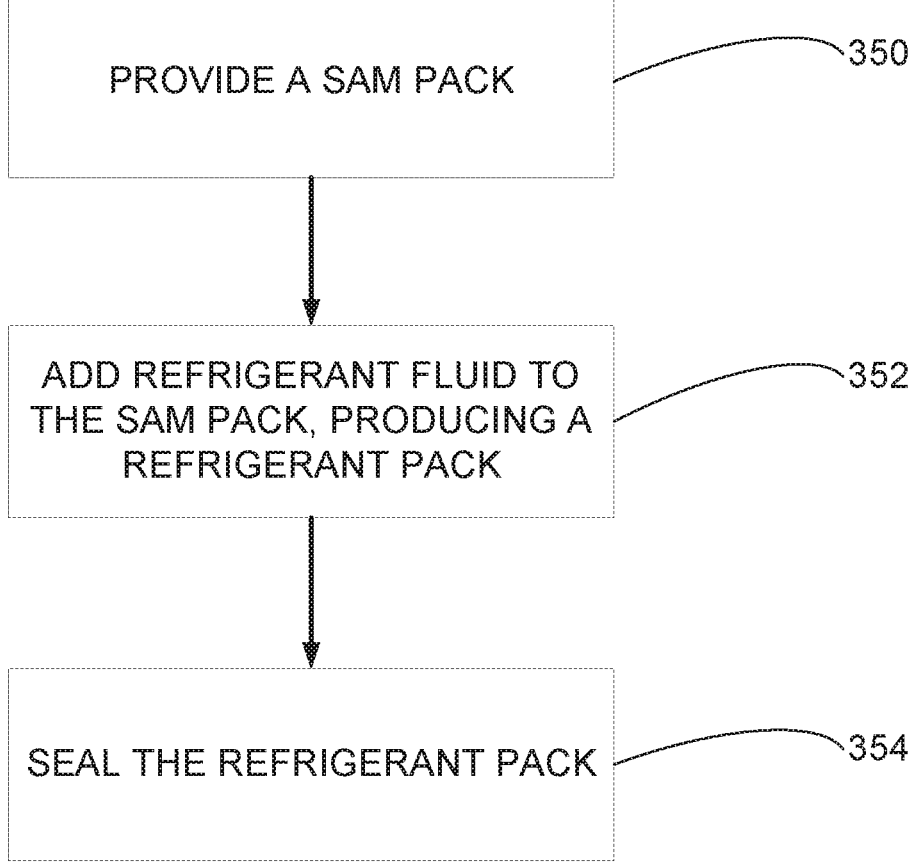
FIG. 3C is a simplified flow chart illustration of a method for providing a cold pack in a packing line according to an example embodiment of the invention.

Reference is now made to FIG. 3C, which is a simplified flow chart illustration of a method for providing a cold pack in a packing line according to an example embodiment of the invention.

FIG. 3C shows a method which includes:

providing a SAM pack with SAM inside and without refrigerant fluid inside (350);

adding refrigerant fluid to an inside of the SAM pack, thereby producing a refrigerant pack (352); and optionally sealing the refrigerant pack (354).

In some embodiments the refrigerant pack is optionally not sealed.

Figure 4A:
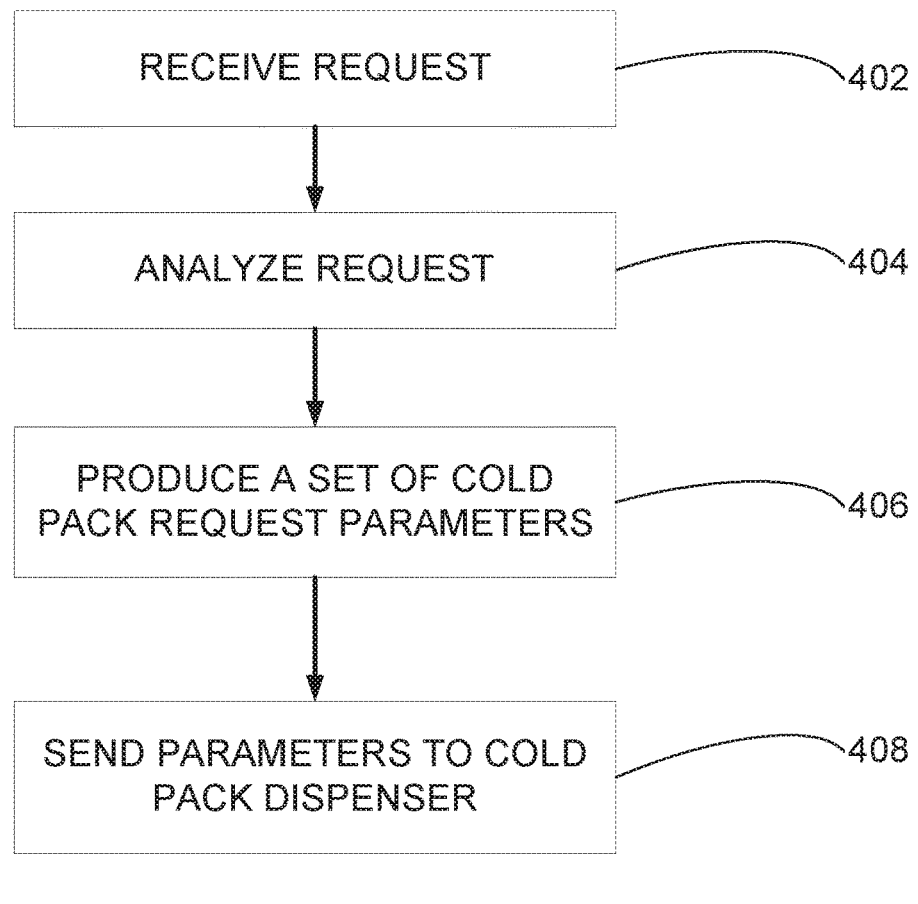
FIG. 4A is a simplified flow chart illustration of a method for handling a request for goods delivery and determining a command for cold pack dispensing associated with the request, according to an example embodiment of the invention.

Reference is now made to FIG. 4A, which is a simplified flow chart illustration of a method for handling a request for goods delivery and determining a command for cold pack dispensing associated with the request, according to an example embodiment of the invention.

FIG. 4A shows a process which includes:

receiving a request for goods delivery (402). In some embodiments a computer or a data center associated with a goods delivery center receives a request from a customer. In some embodiments the request is optionally fed into a data collection center;

analyzing the request (404). The request is analyzed to determine goods request parameters including one or more of the type, size, weight, volume and number of products that require refrigeration, temperature desired for shipping the goods and type, size of the shipping box planned for packing the goods;

producing a set of cold pack request parameters (406), including one or more of a size of a cold pack, a number of cold packs per package, and temperature of the cold pack; and sending the set of cold pack request parameters to a cold pack dispenser (408).

In some embodiments the method optionally includes the cold pack dispenser dispensing cold packs based, at least in part, on the set of cold pack request parameters.

In some embodiments when a box with goods to be shipped reaches the cold pack dispenser, the right amount of packs is dispensed into the box.

In some embodiments a user/packaging worker optionally makes an assessment of what set of cold pack request parameters should be used for a box or package, and feeds the parameters using a keyboard or a user interface to feed this set of parameters to the cold pack dispenser.

Figure 4B:
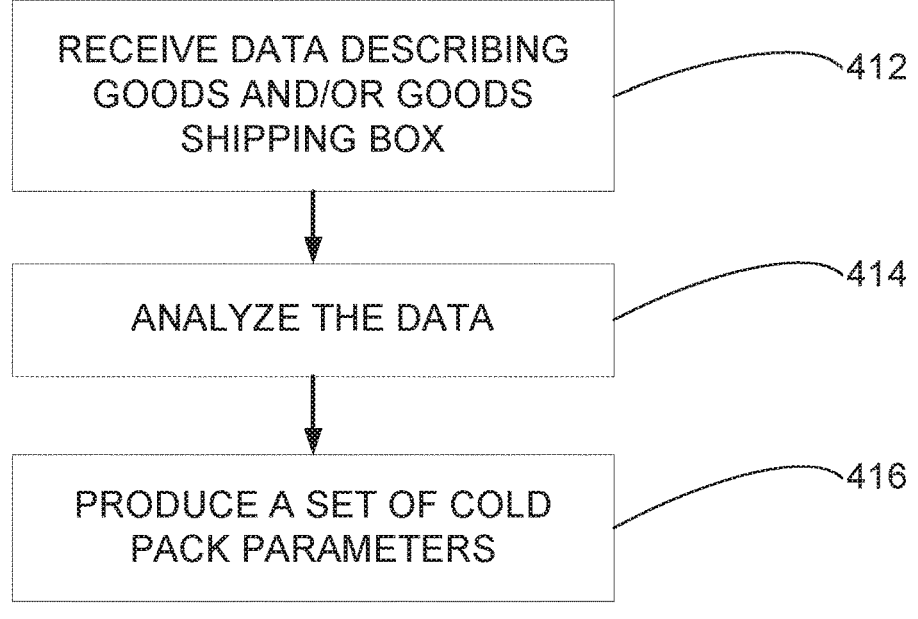
FIG. 4B is a simplified flow chart illustration of a method for analyzing goods contents in a goods shipping box and determining parameters for adding cold packs to the goods shipping box, according to an example embodiment of the invention.

Reference is now made to FIG. 4B, which is a simplified flow chart illustration of a method for analyzing goods contents in a goods shipping box and determining parameters for adding cold packs to the goods shipping box, according to an example embodiment of the invention.

FIG. 4B shows a process which includes:

receiving data describing goods for packing in a goods shipping box (412). In some embodiments a computer or a data center associated with a goods delivery center provides the data. In some embodiments the data may optionally be entered manually into a cold pack analysis module. In some embodiments the data may include weight of goods, volume of goods, temperature of goods and data about the goods shipping box such as insulating properties (carton, plastic, EPS (Expanded Polystyrene), Styrofoam, etc.) and volume of the shipping box;

analyzing the data (414). The data is analyzed to determine cooling capacity desired;

producing a set of cold pack parameters (416), including one or more of a size of a cold pack, a number of cold packs per goods shipping box, and temperature of the cold pack.

In some embodiments the receiving the data describing goods for packing in a goods shipping box comprises reading a barcode on the shipping box and interpreting the barcode to receive the data therefrom.

In some embodiments the receiving the data describing goods for packing in a goods shipping box comprises using a camera to image the shipping box and/or contents of the shipping box, and using image analysis to determine the data, such as a size of the shipping box, number of goods, what portion of the shipping box is full, and additional data determined by the image analysis pertaining to the goods and/or the shipping box.

Figure 4C:
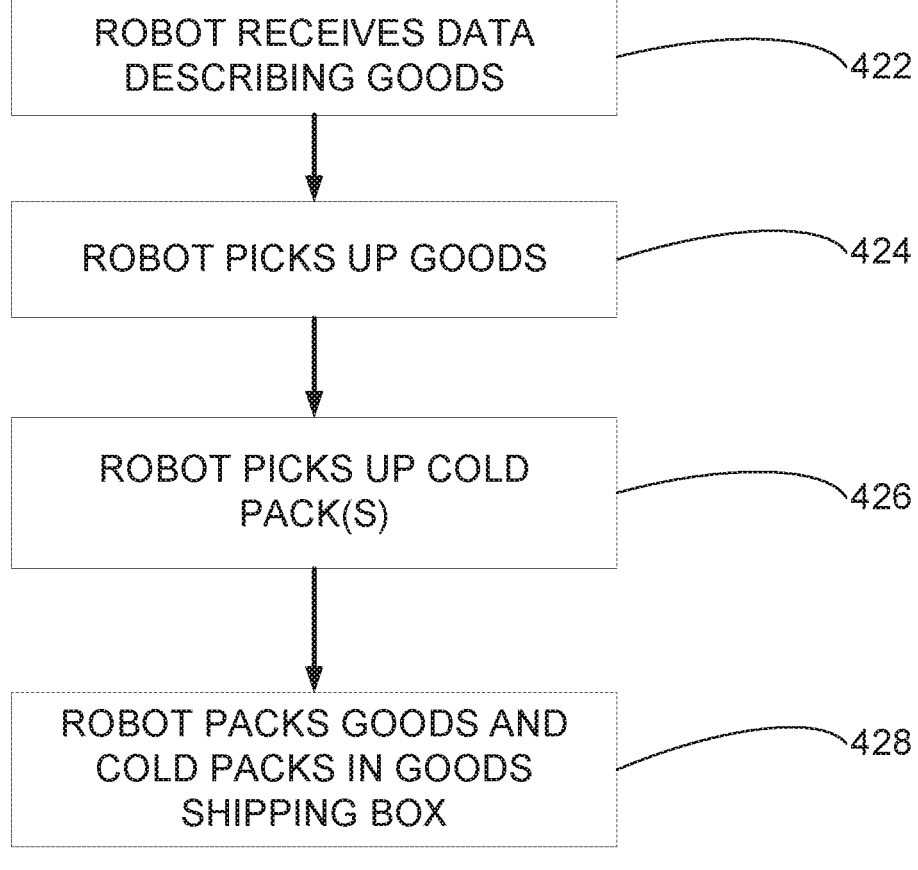
FIG. 4C is a simplified flow chart illustration of a method for using a robot to pack goods and cold packs in a goods shipping box according to an example embodiment of the invention.

Reference is now made to FIG. 4C, which is a simplified flow chart illustration of a method for using a robot to pack goods and cold packs in a goods shipping box according to an example embodiment of the invention.

FIG. 4C shows a process which includes:

a robot receiving data describing goods for packing in a goods shipping box (422);

the robot picking up the goods (424);

the robot picking up cold pack(s) (426); and the robot packing the goods and the cold packs in the goods shipping box (428).

In some embodiments the robot picks up the cold pack(s) from a cold pack machine as described herein.

In some embodiments the robot sends a cold pack request or a goods request to a cold pack machine as described herein.

In some embodiments the robot picks up cold pack(s) before picking up goods. In some embodiments the robot picks up goods before picking up cold pack(s).

In some embodiments the robot places the goods into the goods shipping box before placing the cold packs. In some embodiments the robot places the cold packs into the goods shipping box before placing the goods. In some embodiments the robot intersperses placing the cold packs into the goods shipping box with placing the goods into the goods shipping box.

In some embodiments additional steps of the robot sending a list of goods to a cold pack analysis module and/or the robot receiving data regarding cold pack parameters are optionally included.

In some embodiments a person performs the operations which were described above as performed by the robot.

Methods of Operating a Cold Pack Dispensing System

End of Cold Pack Strip

In some embodiments the SAM packs are provided as a connected chain or strip of SAM packs.

In some embodiments a sensor detects when a last pack in a chain or strip of packs enters a cold pack machine. In some embodiments a check is conducted when the last pack in a chain or strip of packs is detected to enter the cold pack machine.

One or more sensor(s) optionally check an amount if ice accumulated on specific parts inside the machine. The checking is optionally done prior to feeding a new chain into the machine. In some embodiments, if ice is detected to have accumulated above an allowed quantity, the machine optionally blows warm or hot air to thaw the ice. In some embodiments melt water from the thawing is optionally accumulated in a container at a bottom of the machine, or fed to a drain pipe. In some embodiments the machine thaws the ice once every specific period of time. In some embodiments parts of the machine are checked for ice accumulation by shining light such as laser light off the parts.

Various Monitors

In some embodiments a refrigerant fluid injection needle is optionally monitored for correct operation, by way of a non-limiting example by measuring a pressure of fluid during injection, to verify that the needle is not blocked, or partially blocked.

In some embodiments a pack is optionally monitored by a thermometer for pack temperature at one or more locations along a cooling and/or freezing path of a conveyor.

In some embodiments a temperature inside a cooling/freezing machine is optionally monitored by a thermometer, at one or more locations along a cooling/freezing path of a conveyor.

In some embodiments a speed of advance of a conveyor is optionally monitored, by way of a non-limiting example by measuring speed of servo motors advancing the conveyor, optionally using a PLC (Programmable Logic Controller).

Various Controls

In some embodiments a number of packs which are injected with refrigerant fluid is optionally controlled. In some embodiments, the number of packs is optionally monitored by one or more of: a servo motor controller, measuring time, a manual count, a proximity sensor, and an optic sensor.

In some embodiments a number of packs which are cooled/frozen is controlled.

In some embodiments a speed of advance of a conveyor is optionally controlled, to optionally control a temperature of a cold pack, by way of a non-limiting example by measuring speed of servo motors advancing the conveyor, optionally using a PLC.

In some embodiments a quantity of refrigerant fluid injected into a pack is optionally controlled. In some embodiments the control is according to bag size, as manually set up for an injector, as manually entered to a controller by an operator, or as read by a barcode reader reading a barcode on the pack.

In some embodiments a time for cooling and/or freezing a cold pack is optionally controlled. In some embodiments the time is set according to bag size, as manually set up for a cooler/freezer, as manually entered to a cooler/freezer controller by an operator, as read by a barcode reader reading a barcode on the pack, or as calculated based on information about the pack size.

Considerations Regarding Amount Parameters

In some embodiments a cold pack dispensing system and/or a warehouse which dispenses merchandise packed with cold packs optionally controls various amount parameters based on potential merchandise shipping and/or merchandise storage considerations.

In some embodiments, the amounts which are optionally controlled include one or more of:

number of cold pack(s) to be used;

size of cold pack(s) to be used;

weight of cold pack(s) to be used;

total weight of cold packs to be used;

weight of SAM in cold pack(s) to be used;

weight of refrigerant fluid in cold pack(s) to be used; and temperature of cold packs.

Considerations for controlling the above-mentioned amounts optionally include one or more of the following:

intended duration of storage of the cold packs before packaging with merchandise;

intended duration of storage of the merchandise;

intended duration of shipping of the merchandise;

to what temperature the merchandise may be cooled or frozen without damage;

insulating parameters relating to an intended package;

maximum weight of cold pack(s) plus merchandise in a package (for example when packaging cold pack(s) and merchandise for delivery by a drone with limited lifting capacity.

In some embodiments the considerations are performed automatically by a cold pack dispensing system or by a software program.

In some embodiments the considerations are performed by modeling heat flow of an intended package.

In some embodiments the considerations are performed by using a Look-Up-Table which includes one or more parameters listed in the amounts list and/or one or more parameters listed in the considerations list.

End of Shift Mode

In some embodiments, at an end of a work shift, the machine goes into a cold saving mode. The temperature inside the machine is optionally kept constant by blowing cold air into the machine. In some embodiments the cold air flows into the machine at specific time intervals. In some embodiments the cold air flows into the machine in response to one or more temperature sensor(s) sensing a temperature above a specific temperature.

In some embodiments moving parts of the machine perform a back-and-forth movement to avoid seizure by ice.

Start of Shift Mode

In some embodiments, at a start of a work shift, the machine may be empty of cold packs. When SAM packs are fed into the machine, optionally in response to a computerized request, optionally automatically, a cooler and/or blower in the machine is optionally operated at full cooling power, until the cold packs reach a requested temperature. In some embodiments, once the requested temperature has been reached, the refrigerator may optionally operate at a lower intensity.

Maintaining Temperature Mode

In some embodiments the machine may be at a desired temperature, and enter into an energy saving mode.

Replacing a Water Injection Needle

In some embodiments a water injection needle is optionally monitored by one or more sensor(s). In some embodiments the water injection needle is optionally monitored to detect accumulation of scale in the water injection needle. In some embodiments the water injection needle is optionally monitored to detect accumulation of SAM blocking the water injection needle.

In some embodiments scale on the injection needle is optionally monitored by laser sensors.

In some embodiments scale on the injection needle is optionally monitored by monitoring a pressure required to push a syringe and/or by monitoring a speed of movement of a plunger of a syringe.

In some embodiments, when the water injection needle is detected as requiring maintenance, the cold pack dispensing machine, or the fluid injection component, optionally sends a message to a machine control unit to replace the needle.

In some embodiments, in addition to or instead of reacting to a maintenance message, a periodic replacement of the needle is performed.

Water Filter Cleaning and/or Replacement

In some embodiments, water filters are optionally checked for cleanliness at the beginning of each shift. In some embodiments, filters are replaced periodically.

Maintenance Schedule

In some embodiments moving parts such as bearings, electric motors, blowers and the like are checked periodically and replaced when necessary.

An Injector-Sealer Machine

Figure 5A:
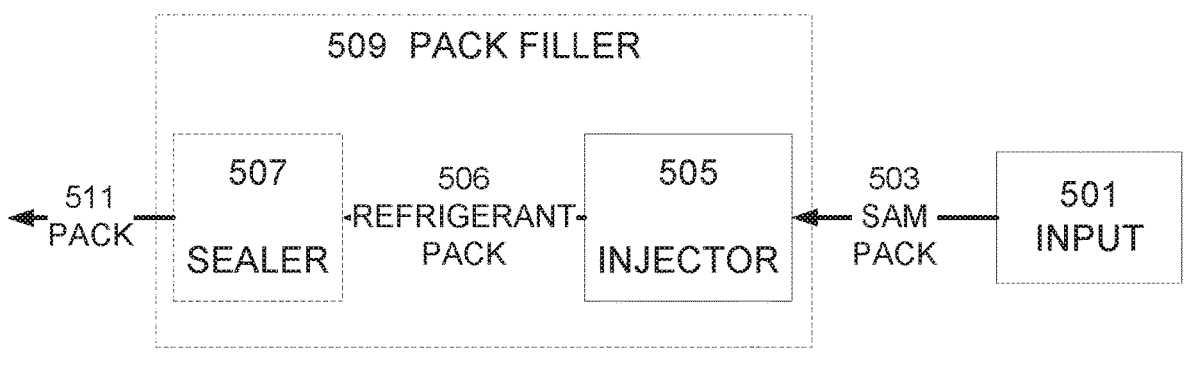
FIG. 5A is a simplified block diagram illustration of a device which receives SAM packs and dispenses packs with refrigerant fluid or gel according to an example embodiment of the invention.

Reference is now made to FIG. 5A, which is a simplified block diagram illustration of a device which receives SAM packs and dispenses packs with refrigerant fluid or gel according to an example embodiment of the invention.

FIG. 5A shows some device components along a refrigerant filling path, from a SAM pack input 501 to dispensing a pack.

In some embodiments, a pack filler device 509 receives a SAM pack 503 from the SAM pack input 501. The SAM pack 503 enters the pack filler device 509. The pack filler device 509 optionally includes an injector 505, which injects refrigerant fluid into the SAM pack 503, producing a refrigerant pack 506.

In some embodiments the pack filler device 509 also includes an optional pack sealer component 507, which optionally seals the injected pack, producing a sealed pack 511 with refrigerant fluid.

In some embodiments the pack filler device 509 does not seal the injected pack, producing a not-sealed pack 511 with refrigerant fluid.

Figure 5B:
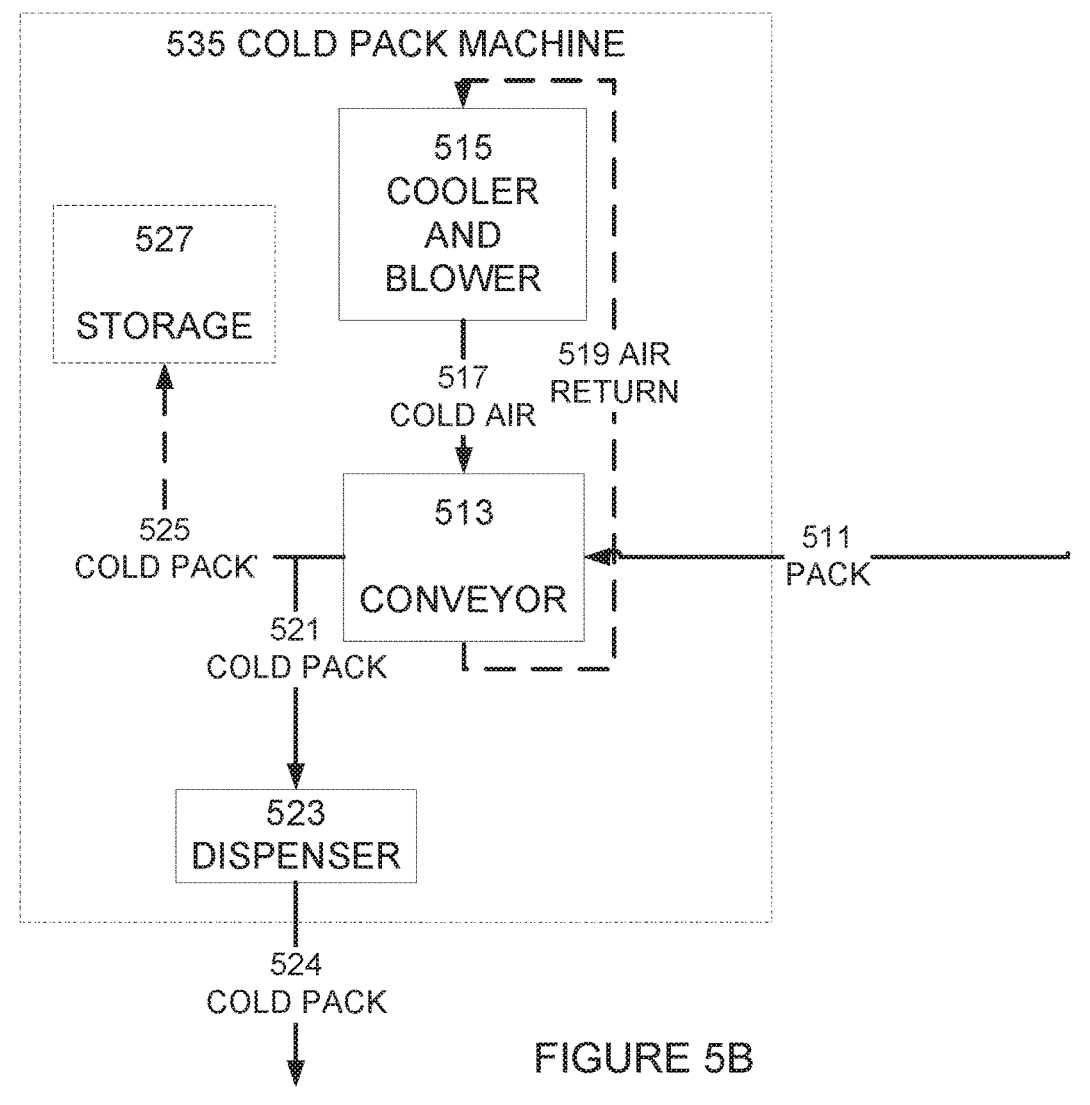
FIG. 5B is a simplified block diagram illustration of a cold pack machine which takes in sealed packs and dispenses cold packs according to an example embodiment of the invention.

Reference is now made to FIG. 5B, which is a simplified block diagram illustration of a cold pack machine which takes in sealed packs and dispenses cold packs according to an example embodiment of the invention.

FIG. 5B shows a cold pack machine 535, which includes a conveyor 513 and a cooler and blower component 515.

A sealed pack 511 with refrigerant fluid optionally enters onto, or optionally a user places onto, a conveyor 513 through the cold pack machine 535. The conveyor 513 carries the pack 511 through a cooler which cools the pack 511 to a desired temperature, producing a cold pack 521 525. In some embodiments the conveyor 513 dispenses the cold pack 521 optionally via an optional dispenser 523 as a cold pack 524.

In some embodiments, the cold pack 525 is stored in an optional storage unit 527, for optional dispensing later, for example by user taking the cold pack 525 from the storage unit 527, or by the storage unit 527 dispensing a cold pack in response to a computer command, optionally through the optional dispenser 523, or through another optional dispenser.

In some embodiments the cold pack machine 535 of FIG. 5B optionally includes the pack filler 509 as a component of the cold pack machine 535.

In some embodiments the cold pack machine 535 optionally includes a computer control unit (not shown), for controlling parameters of the cold pack machine 535 for producing, by way of some non-limiting example, a desired number of cold packs, at a desired temperature, at a desired point in time.

FIG. 5B also shows a cooler and blower 515 optionally blowing cold air 517 for cooling the packs 511 on the conveyor 513. In some embodiments the cold air 517 is collected and returned as air return 519 to the cooler and blower 515.

In some embodiments the cold pack machine 535 optionally includes one or more of a user interface (not shown), the storage 527 and an optional second dispenser (not shown).

Figure 5C:
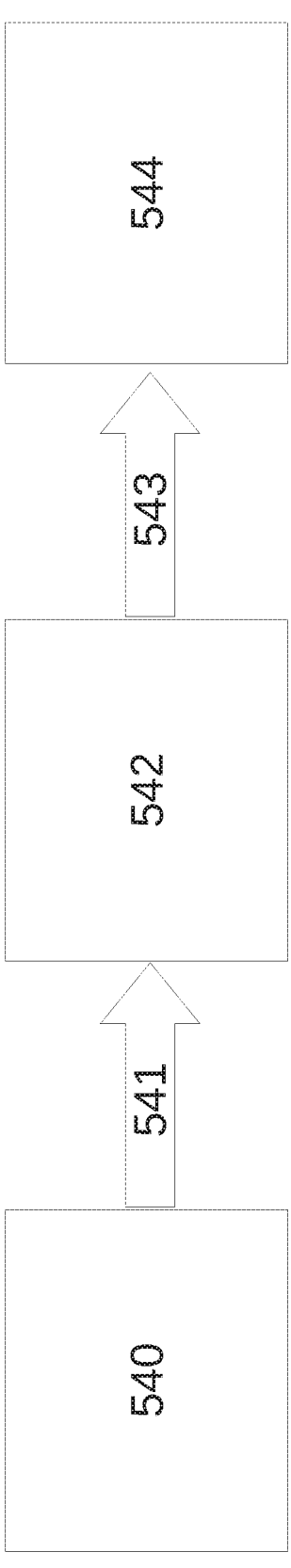
FIG. 5C is a simplified block diagram illustration of a method for producing filling and cooling a cold pack according to an example embodiment of the invention.

Reference is now made to FIG. 5C, which is a simplified block diagram illustration of a method for producing filling and cooling a cold pack according to an example embodiment of the invention.

FIG. 5C shows a first machine 540 for producing SAM packs, a second machine 542 for filling the SAM packs with refrigerant fluid, producing refrigerant packs, and a third machine 544 for cooling and/or freezing the refrigerant packs.

In some embodiments, the first machine 540 is optionally located at a first location, optionally producing the SAM packs at a SAM pack production facility, and optionally ships 541 the SAM packs to a second location, optionally at a client's warehouse.

In some embodiments, the second machine 542 optionally fills the SAM packs with refrigerant fluid, optionally at the client's warehouse, optionally producing refrigerant packs. In some embodiments the refrigerant packs are optionally fed 543 into the third machine 544 for cooling and/or freezing the refrigerant packs.

In some embodiments the feeding 543 is optionally a feeding onto a conveyor belt which carries the refrigerant packs through a cooling tower in the third machine 544, optionally at the client's warehouse.

In some embodiments the third machine 544 is optionally a machine designed for freezing pizzas and/or hamburgers, and/or a standard freezing machine as is known in the art.

Figure 6A:
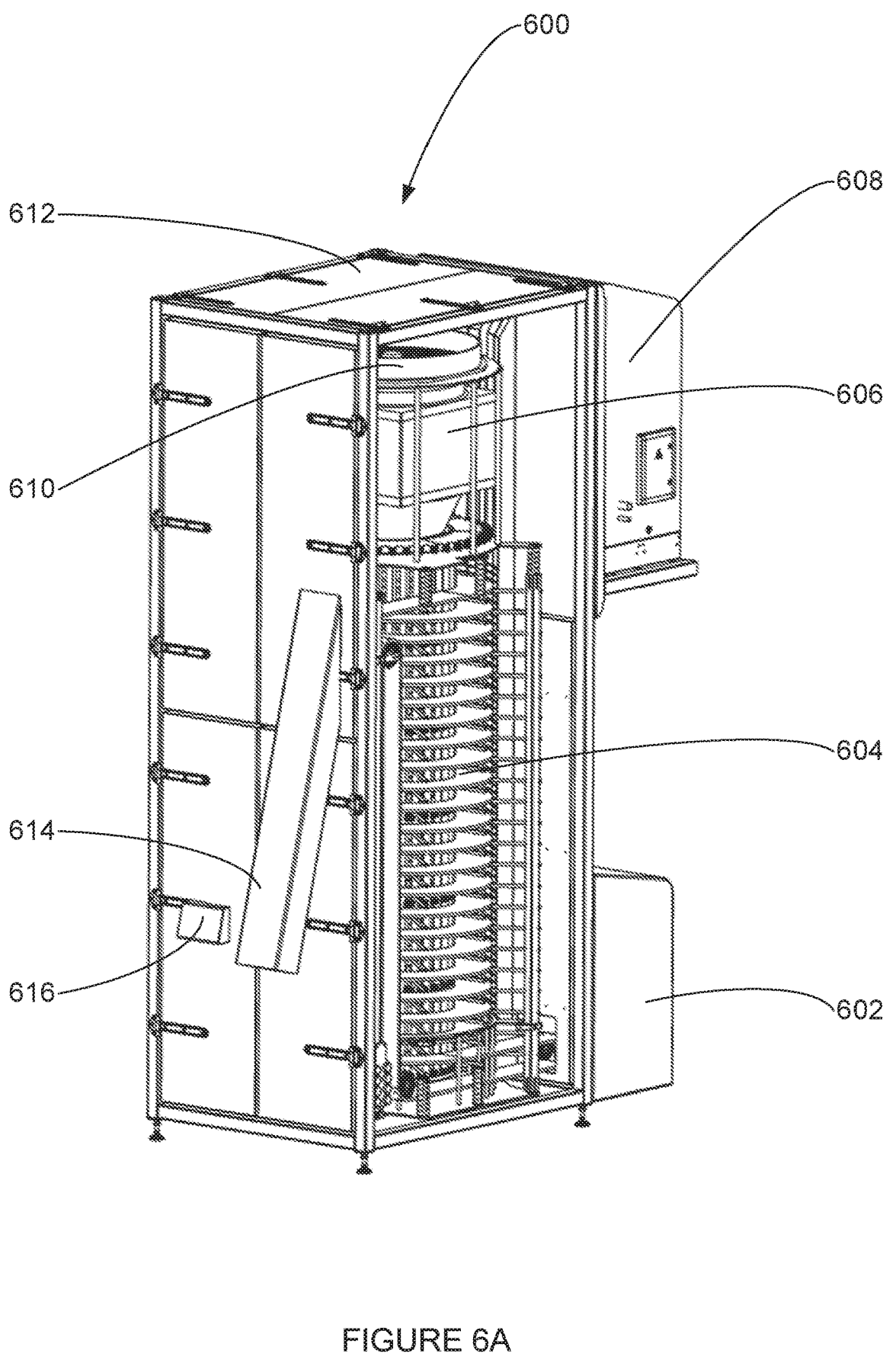

Reference is now made to FIG. 6A, which is a simplified illustration of a cold pack machine according to an example embodiment of the invention.

FIG. 6A shows a cold pack machine 600 with an optional insulated cabinet 612 with some panels open so as to provide a view inside the cold pack machine 600.

The example embodiment cold pack machine 600 shown in FIG. 6A includes:

a fluid refrigerant filling component 602, for example a water injection component, optionally including a pack sealing component;

a conveyor 604, optionally a helical conveyor for most or all of its length;

a blower 610, blowing air through a cooling evaporator 606; and a cooling system condenser 608.

In some embodiments the cold pack machine 600 shown in FIG. 6A optionally includes a dispensing chute 614.

In some embodiments the cold pack machine 600 shown in FIG. 6A optionally includes a control panel 616.

Figure 6B:
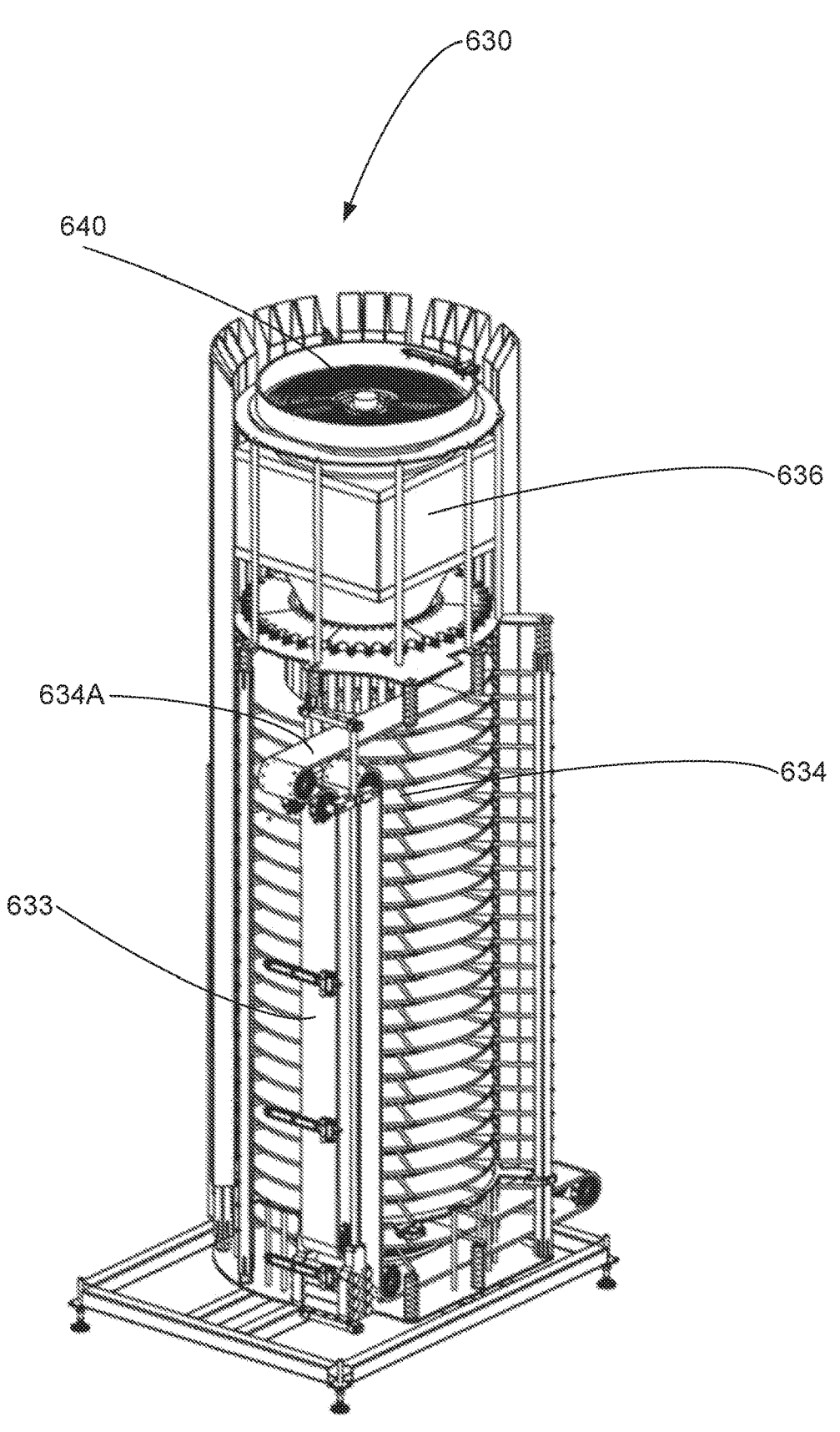
FIG. 6B is a simplified illustration of a cold pack machine according to an example embodiment of the invention.

Reference is now made to FIG. 6B, which is a simplified illustration of a cold pack machine according to an example embodiment of the invention.

FIG. 6B shows a cold pack machine 630 without optional cabinet panels, so as to provide a view inside the cold pack machine 630.

The example embodiment cold pack machine 630 shown in FIG. 6B includes:

a conveyor 634, optionally a helical conveyor for most or all of its length; and a blower 640, blowing air through a cooling evaporator 636.

In some embodiments the cold pack machine 600 shown in FIG. 6B optionally includes a conveyor portion 634A, which conveys cold packs to a dispensing chute (not shown) such as, by way of a non-limiting example, the dispensing chute 614 of FIG. 6A.

In some embodiments the cold pack machine 600 shown in FIG. 6B optionally includes a conveyor portion 633, which makes the conveyor 634, the conveyor portion 633 and optionally the conveyor 634A a closed loop conveyor or belt.

In some embodiments the cold pack machine 600 optionally includes a refrigerant filler (not shown) such as the refrigerant filling component 602 of FIG. 6A. In some embodiments the refrigerant filler optionally includes a device or conveyor which takes in a strip of SAM packs, which optionally conveys the strip of SAM packs past the refrigerant filler, optionally, by way of some non-limiting examples, such as the refrigerant filling devices shown in FIGS. 8A, 8B and 9.

Figure 7:
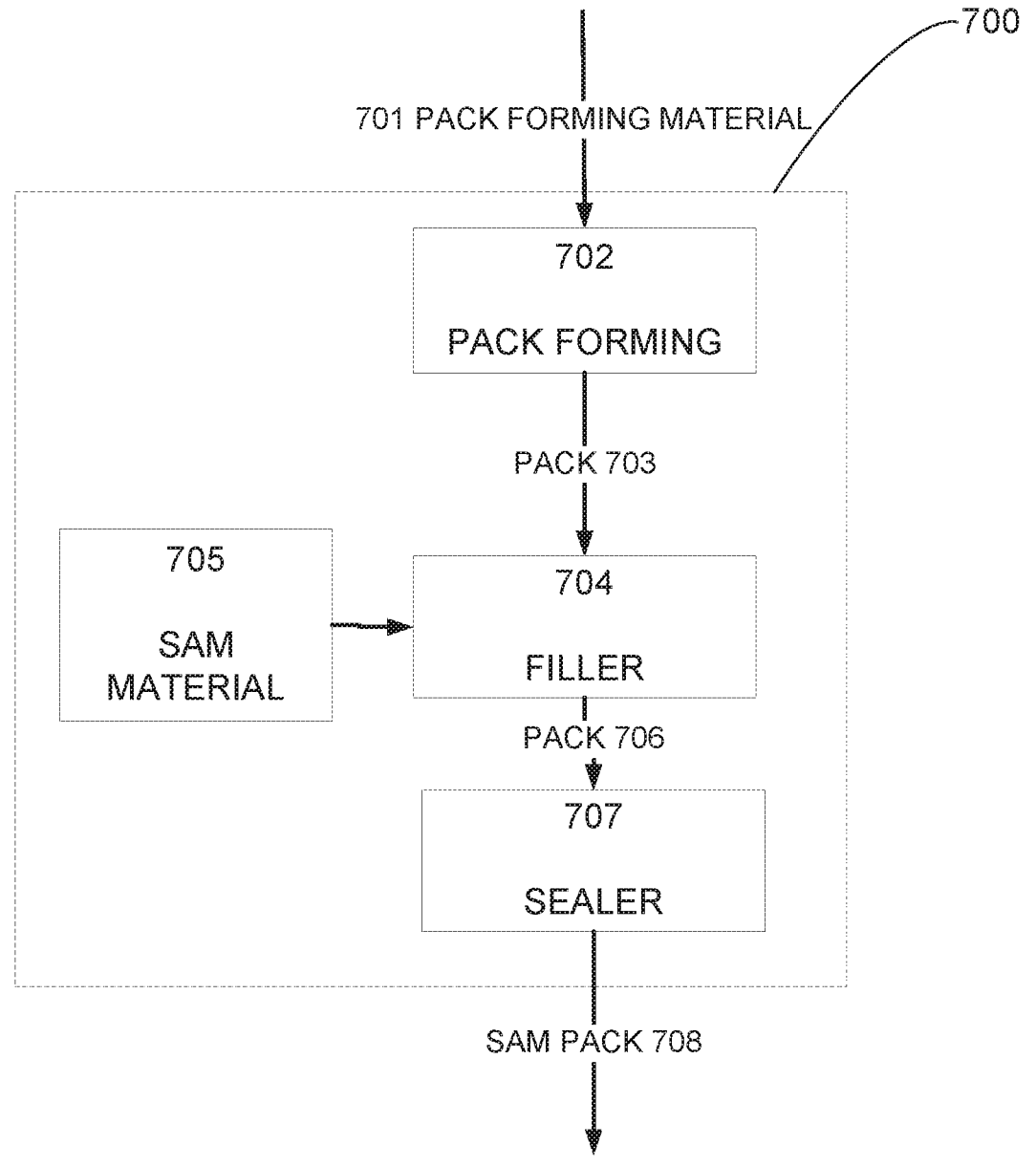
FIG. 7 is a simplified block diagram illustration of a device for producing a SAM pack according to an example embodiment of the invention.

Reference is now made to FIG. 7, which is a simplified block diagram illustration of a device for producing a SAM pack according to an example embodiment of the invention.

FIG. 7 shows a device 700 which includes:

a pack forming component 702 for taking in pack forming material 701, forming the material 701 into a pack 703;

a filler component 704 for filling the pack 703 with SAM from a SAM storage component 705, producing a pack 706 with SAM inside; and an optional sealer component 707 for sealing the pack 706 and producing a sealed SAM pack 708.

In some embodiments the pack forming component 702 and the filler component 704 are formed as one unit.

In some embodiments the pack forming component 702 and the filler component 704 are a bag form and fill machine.

In some embodiments the pack forming component 702, the filler component 704 and the sealer component 707 are a Form Fill and Seal machine.

In some embodiments the device 700 does not include an optional sealer component 707.

In some embodiments the sealer 707 optionally does not seal all or some of the packs 706.

Figure 8A:
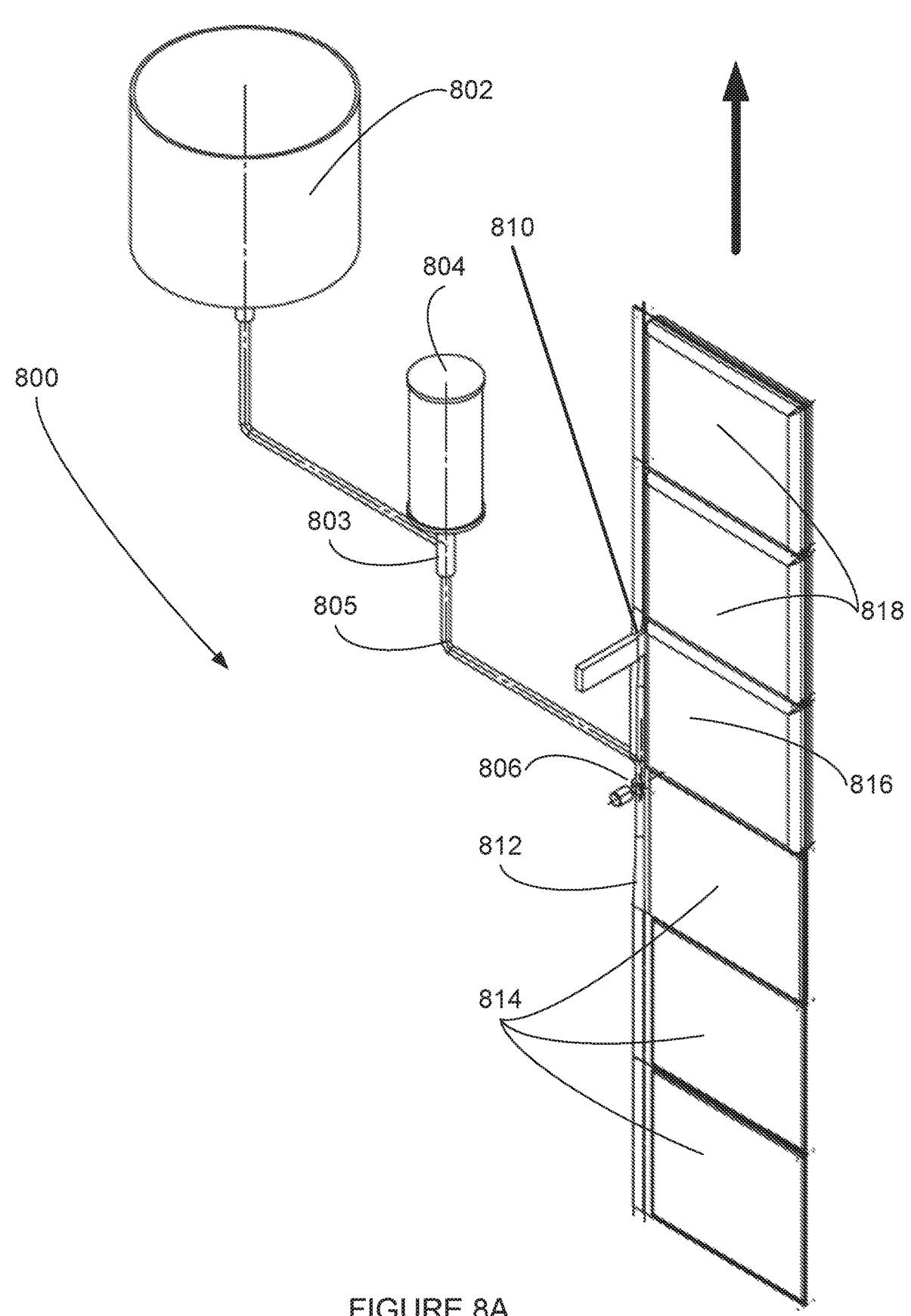
FIG. 8A is a simplified illustration of a refrigerant filling and sealing machine according to an example embodiment of the invention.

Reference is now made to FIG. 8A, which is a simplified illustration of a refrigerant filling and sealing machine according to an example embodiment of the invention.

FIG. 8A shows a refrigerant filling and sealing machine 800, including:

a tank 802 for refrigerant fluid such as, by way of a non-limiting example, water;

an optional piston 804 for optionally pushing a dispensing plunger to dispense the refrigerant fluid for injection into SAM packs 814;

an optional non-return valve 803;

a pipe 805 for feeding the optionally pressurized refrigerant fluid through an orifice in the pipe 805; and an optional sealer 810 for optionally sealing a SAM pack 816 which has been injected with refrigerant fluid, producing a sealed SAM pack 818.

In some embodiments the refrigerant filling and sealing machine 800 includes an optional pressurization component for optionally pressurizing the refrigerant fluid for injection into SAM packs 814.

In some embodiments the refrigerant filling and sealing machine 800 uses tap water as a refrigerant fluid, the tap water typically provided at a pressure of 1-4 bars.

I some embodiments the pipe 805 enters a sleeve 812 of the SAM pack 814.

In some embodiments the machine 800 includes a clamp 806 for clamping the sleeve 812 to the pipe 805 during an injecting of the refrigerant fluid.

In some embodiments the machine 800 does not include a sealer 810.

In some embodiments the machine 800 optionally does not seal all or some of the SAM packs 816 which have been injected with refrigerant fluid.

Figure 8B:
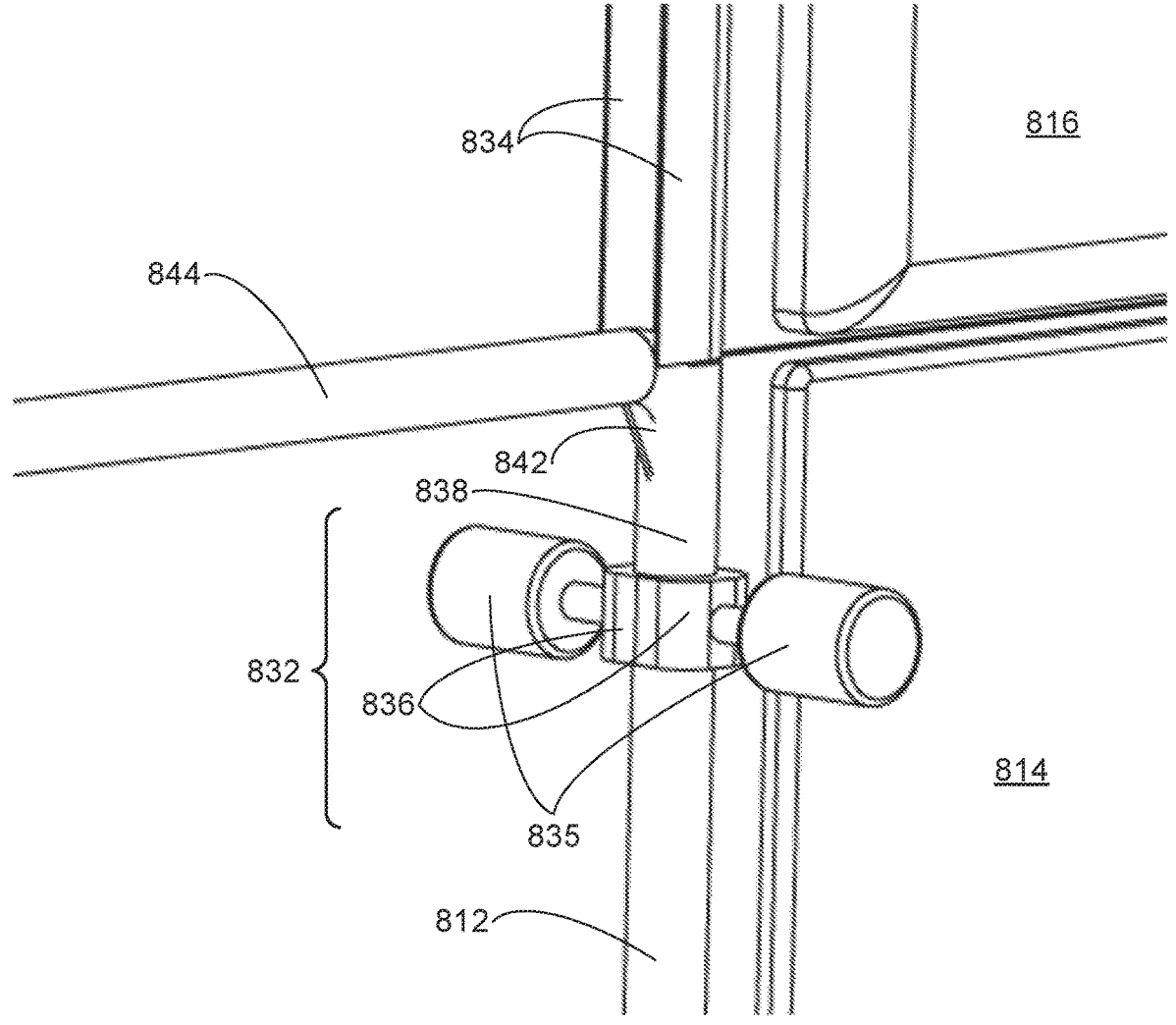
FIG. 8B is a simplified illustration of components of the refrigerant filling and sealing machine of FIG. 8A.

Reference is now additionally made to FIG. 8B, which is a simplified illustration of components of the refrigerant filling and sealing machine of FIG. 8A.

FIG. 8B shows components of a refrigerant filling and sealing machine, including:

the pipe 844 of FIG. 8A;

an optional SAM pack injection device 832, including optional clamps 836 and optional solenoid(s) or piston(s) 835, for optionally clamping the sleeve 812 of a first SAM pack 814 around the pipe 844 during injection; and an optional knife 842 for optionally cutting open a slit in the sleeve 812.

In some embodiments cutting the edge open optionally slits open the sleeve 812 of the first SAM pack 814, opening the first SAM pack 814 to filling of refrigerant fluid through a side orifice in the refrigerant providing pipe 844.

FIG. 8B shows two open edges 834 of a second pack 816.

FIG. 8B shows the second pack 816 as a thicker pack than the SAM pack 814, to indicate that the second pack 816 has been filled with refrigerant fluid.

In some embodiments there is no optional knife 842 in the refrigerant filling and sealing machine, and the filling of refrigerant fluid is optionally performed by injecting without cutting open an edge of the SAM pack 814.

In some embodiments a portion of an edge, or a whole edge, or a portion of more than one edge of the SAM pack 814 are sealed by adhesive, and the optional SAM pack edge separation device 832 does not necessarily include a knife 842 for cutting the edge 838 open.

Figure 8C:
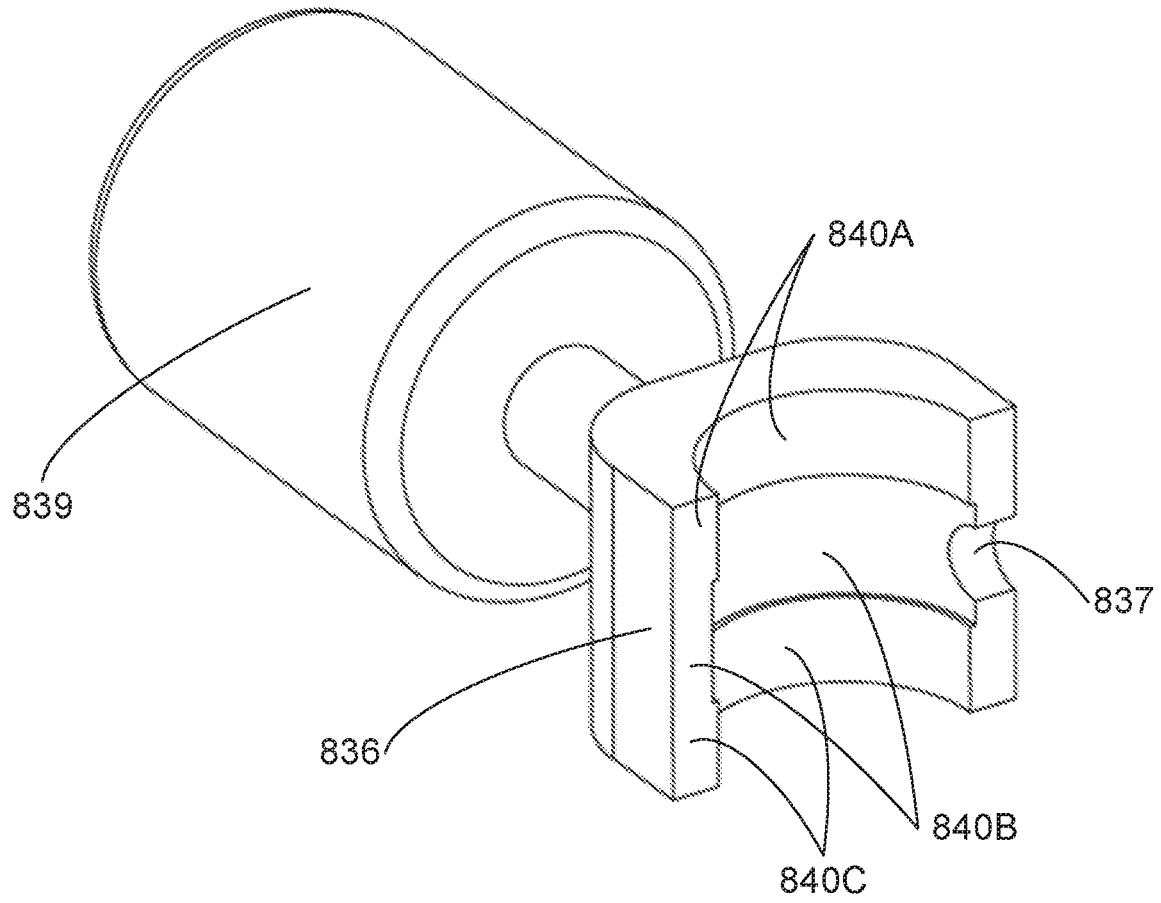
FIG. 8C is a simplified illustration of an optional clamp and an optional piston or solenoid of the refrigerant filling and sealing machine of FIG. 8A.

Reference is now additionally made to FIG. 8C, which is a simplified illustration of an optional clamp and an optional piston or solenoid of the refrigerant filling and sealing machine of FIG. 8A.

FIG. 8C shows one clamp 836 and one optional solenoid or piston 839.

In some embodiments the clamp 836 optionally includes a half-hole 837 in the clamp 836 for allowing a water jet to pass through and optionally fill a SAM pack with water. The half-hole 837 potentially works together with another half-hole (not shown) in a mating clamp (not shown) to form a hole for allowing the water jet to pass through.

In some embodiments the clamp 836 optionally seals the sleeve 812 of FIGS. 8A and 8B around the pipe 844 of FIGS. 8A and 8B during injection.

In some embodiments the clamp 836 is optionally shaped with a recess 840B between two protuberances 840A 840C, so the protuberances 840A 840C clamp the sleeve 812 around the pipe 844, clamping the sleeve 812 so that refrigerant fluid does not leak and pressure is not lost between the sleeve 812 and the pipe 844.

Figure 8D:
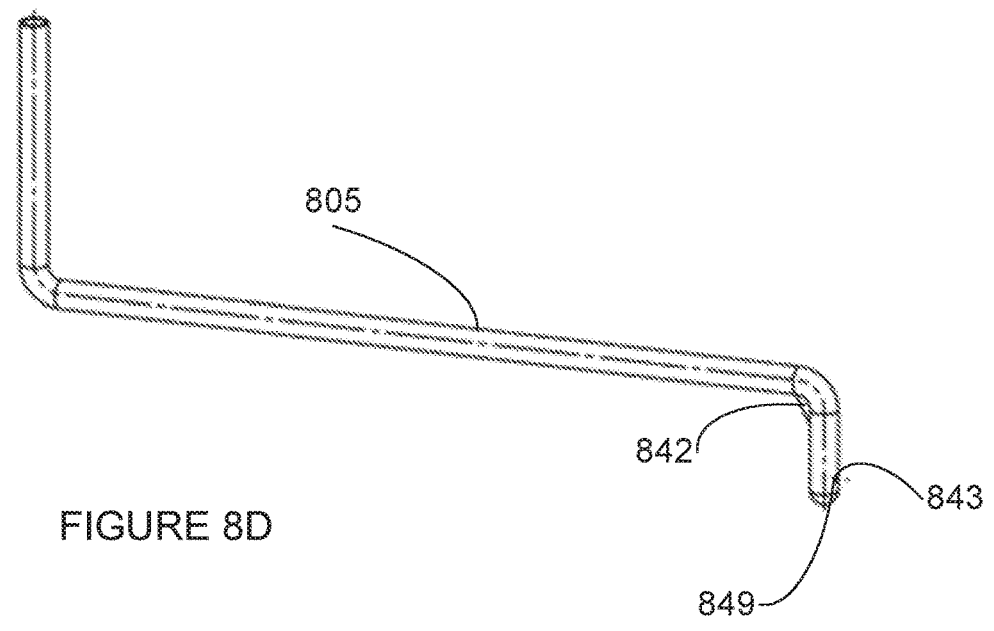
FIG. 8D is a simplified illustration of a pipe for side fluid injection of the refrigerant filling and sealing machine of FIG. 8A.

Reference is now additionally made to FIG. 8D, which is a simplified illustration of a pipe for side fluid injection of the refrigerant filling and sealing machine of FIG. 8A.

FIG. 8D shows the pipe 805 and the knife 842 of FIG. 8B, and a side orifice 843 for injecting water into a SAM pack, such as the SAM pack 814 of FIG. 8B.

In some embodiments an end 849 of the pipe 805 is closed and rounded and/or shaped to work its way into the sleeve 812 of FIGS. 8A and 8B.

Figure 8E:
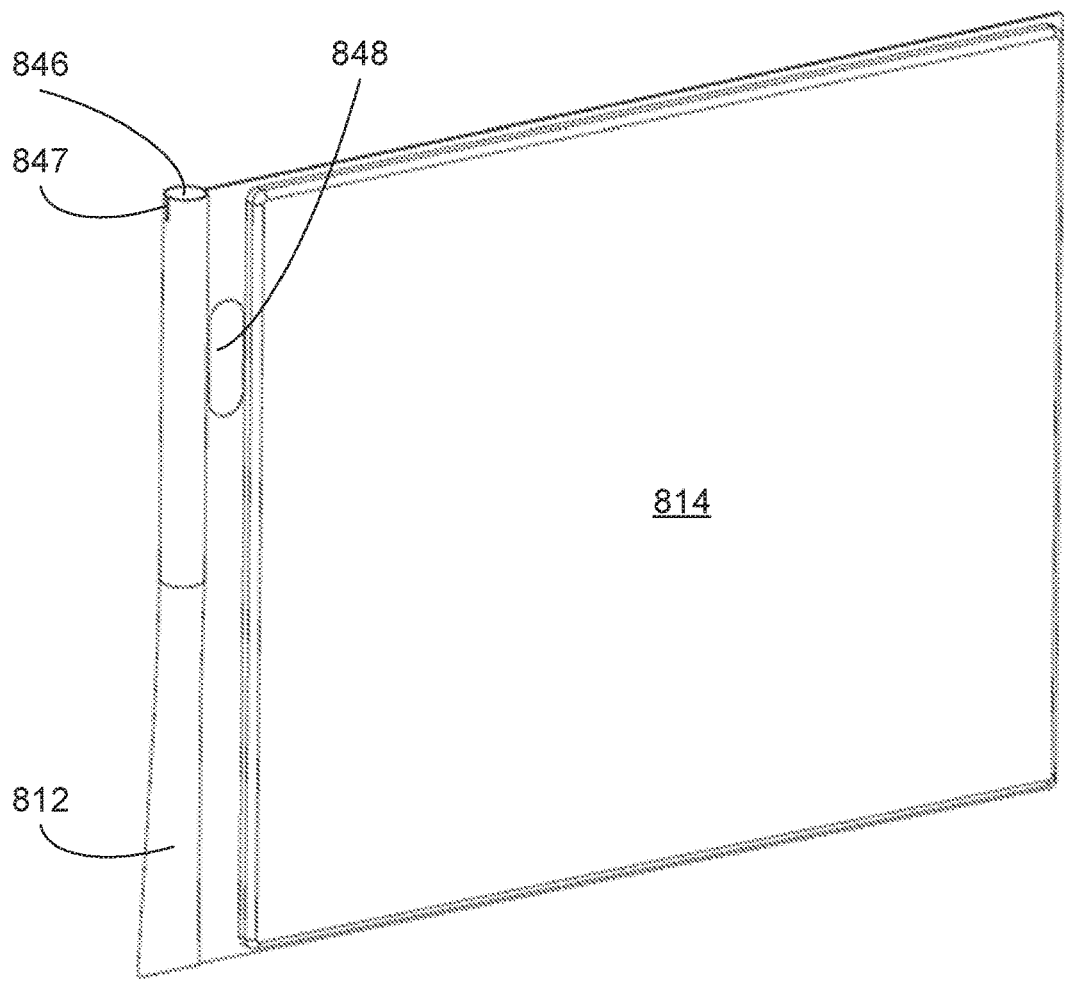
FIG. 8E is a simplified illustration of a SAM pack arranged for side fluid injection of the refrigerant filling and sealing machine of FIG. 8A.

Reference is now additionally made to FIG. 8E, which is a simplified illustration of a SAM pack arranged for side fluid injection of the refrigerant filling and sealing machine of FIG. 8A.

FIG. 8E shows a SAM pack 814, having a sleeve 812 along at least one side of the SAM pack 814. When the SAM pack 814 reaches a point in which the pipe 805 of the refrigerant filling and sealing machine 800 of FIG. 8A enters the sleeve 812 of the SAM pack 814, the pipe 805 enters an opening 846 in the sleeve 812, and optionally the optional knife 842 of FIG. 8D optionally cuts a slit 847 in the sleeve 812, for the pipe 805 of FIG. 8D to pass along the slit 847.

FIG. 8E shows an example embodiment of a SAM pack 814 which optionally includes a portion 848 of a seam of the SAM pack 814 designed for opening under fluid pressure and allowing refrigerant fluid into the SAM pack 814.

In some embodiments the portion 848 is glued, while a rest of the SAM pack 814 periphery is heat sealed.

In some embodiments the portion 848 is lightly glued, to be waterproof but also openable under pressure as supplied by the pipe 805 of FIG. 8A, while the rest of the periphery of the SAM pack 814 is optionally glued to remain sealed, and/or the rest of the periphery of the SAM pack 814 is optionally heat sealed.

In some embodiments the pipe 805 provides tap water as a refrigerant fluid, the tap water typically provided at a pressure of 1-4 bars.

In some embodiments the portion 848 is lightly heat sealed, by a thin seam, while a rest of the periphery of the SAM pack 814 is optionally better heat sealed, with a stronger and/or thicker seam.

In some embodiments the portion 848 of the seam is sealed, whether glued or heat-sealed, so that a force of 50-500 grams pulling sides of the SAM pack 814 apart opens the portion of the seam.

In some embodiments the portion 848 of the seam is sealed, whether glued or heat-sealed, so that a fluid refrigerant pressure in a range of 0.25-5 bars opens the portion 848 of the seam.

In some embodiments using tap water at normal tap water pressure is sufficient to open the portion 848 of the seam.

Figure 8F:
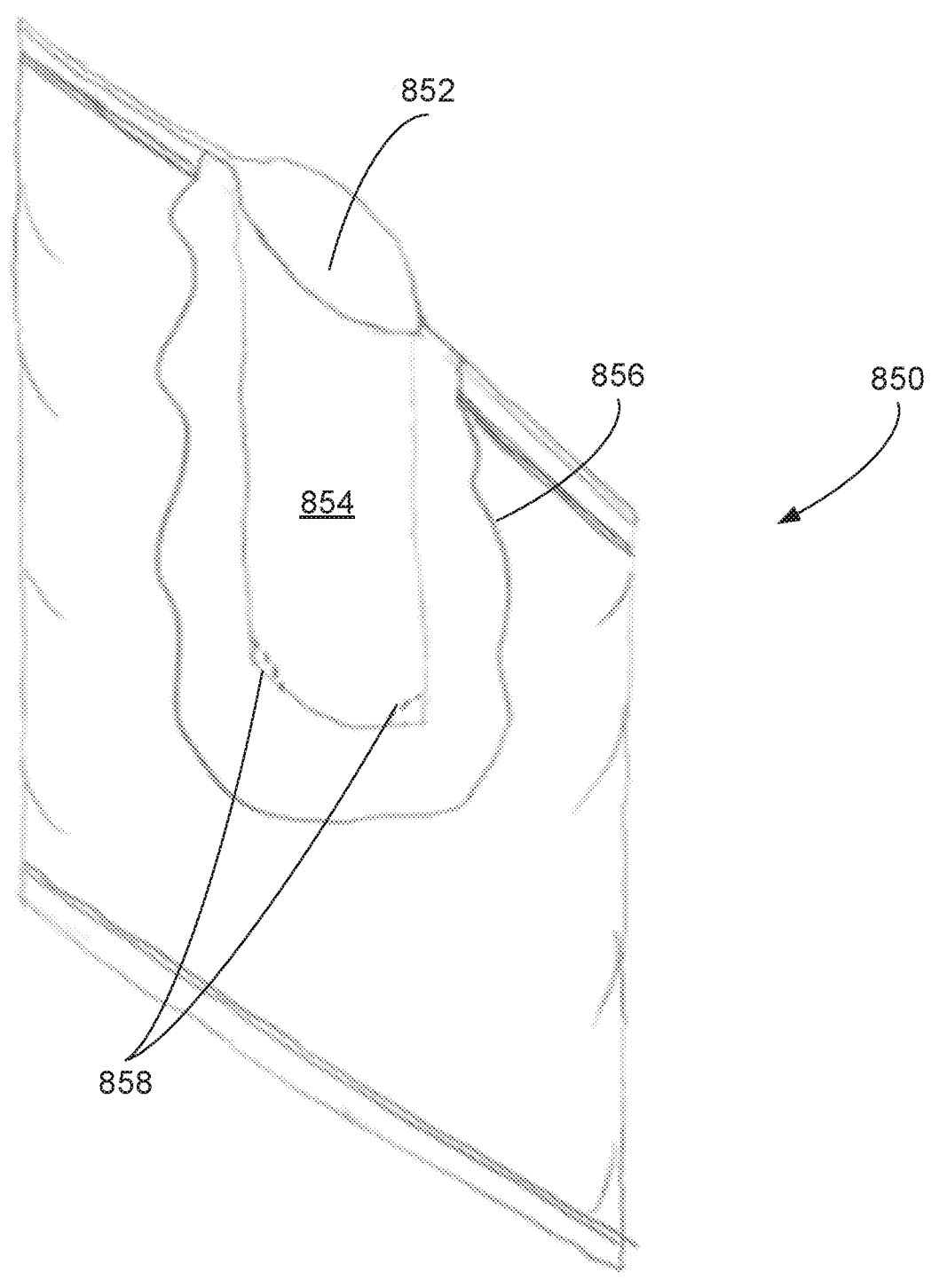
FIG. 8F is a simplified illustration of a SAM pack arranged for fluid injection of refrigerant fluid according to an example embodiment of the invention.

Reference is now made to FIG. 8F, which is a simplified illustration of a SAM pack arranged for fluid injection of refrigerant fluid according to an example embodiment of the invention.

FIG. 8F shows a SAM pack 850, having a tubular opening 852 along one side of the SAM pack 850, and a tube 854 extending from the tubular opening 853 into the SAM pack 850.

FIG. 8F is a view of the SAM pack 850 with a partial cutout 856, in order to show the tube 854 even inside the SAM pack 850.

The tube 854 is optionally mostly closed at an end distant from the opening 852, and optionally has one or more openings 858 at a portion of the tube 854 which is inside the SAM pack 850. In some embodiments the tube 854 optionally has a flat shape.

FIG. 8F shows a non-limiting example embodiment where the openings 858 are at corners of an internal end of the tube 854. In some embodiments the tube 854 optionally has a flat shape.

In some embodiments when the SAM pack is filled with refrigerant fluid, the refrigerant fluid plus SAM mixture expands, exerting pressure on the tube 854 and mechanically sealing the tube 854, preventing leakage of the mixture.

In some embodiments a refrigerant filling and sealing machine injects refrigerant fluid into the tube 854. Pressure of the refrigerant fluid is optionally sufficient to enable the refrigerant fluid to penetrate into the SAM pack 850, mix with the SAM inside, making a SAM and refrigerant fluid mixture. When enough refrigerant fluid has been injected, the SAM pack 850 is mechanically sealed by pressure of the mixture in the SAM pack 850, now a refrigerant pack.

In some embodiments the refrigerant filling and sealing machine 800 of FIG. 8A injects refrigerant fluid into the tube 854.

In some embodiments a refrigerant fluid pressure in a range of 0.25-5 bars is sufficient to fill the SAM pack 850 with refrigerant fluid.

In some embodiments using tap water at normal tap water pressure is sufficient to fill the SAM pack 850 with refrigerant fluid.

Reference is now made to FIGS. 8G-L, which are simplified block diagram illustrations of a SAM pack fluid injection of refrigerant fluid according to an example embodiment of the invention.

Figure 8G:
FIGS. 8G-L are simplified block diagram illustrations of a SAM pack fluid injection of refrigerant fluid according to an example embodiment of the invention.

FIG. 8G shows an example embodiment of a SAM pack 860.

Figure 8H:
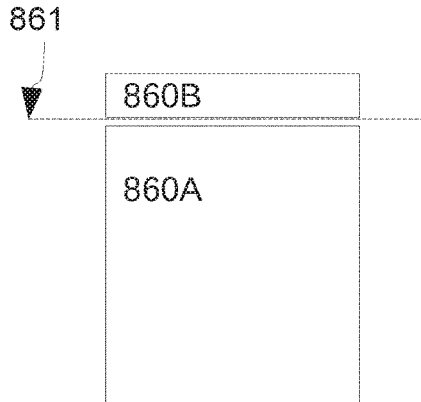

FIG. 8H shows the SAM pack 860 cut along one edge, separated along a line 861 to form an open-edged SAM pack 860A, and a cutoff 860B.

Figure 8I:
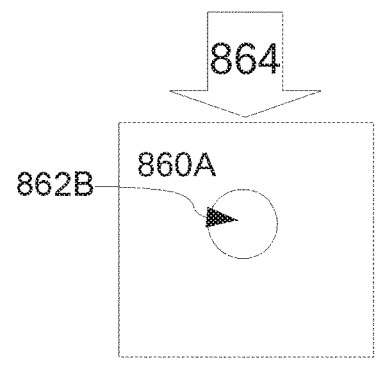
Figure 8J:
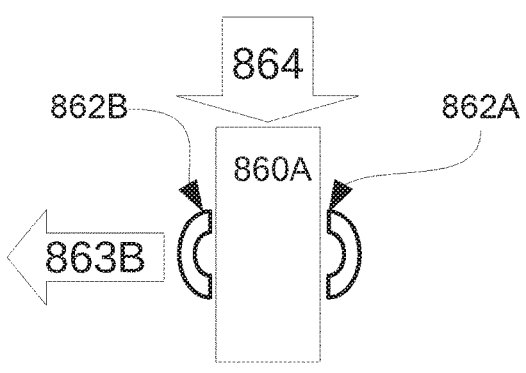
Figure 8K:
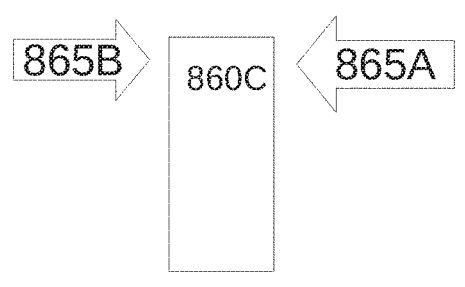

FIGS. 8I and 8J show two views from two perpendicular directions, of the sides of the open-edged SAM pack 860A being pulled open, optionally by vacuum arms or hoses 862A 862B. FIGS. 8I and 8J also show the open-edged SAM pack 860A being filled 864 with refrigerant fluid, FIG. 8K shows the open-edged SAM pack 860A optionally being sealed 865A 865B along its open edge, producing a sealed refrigerant pack 860C. In some embodiments the sealing may be heat sealing or gluing, or other methods of sealing as described herein and/or as are known in the art.

Figure 8L:
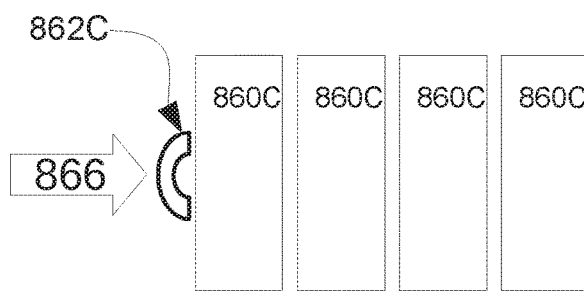

FIG. 8L shows the sealed refrigerant pack 860C optionally placed or packaged side by side with additional sealed refrigerant packs 860C.

In some embodiments the sealed refrigerant packs 860C are optionally placed 866 side by side by a vacuum arm or hose 862C. In some embodiments the vacuum arm or hose 862C is optionally one of the vacuum arms or hoses 862A 862B.

In some embodiments the actions of opening, filling with refrigerant and sealing as described above with reference to FIG. 8H-8K or 8H-8L are optionally performed by a specific machine suitable for this purpose.

Figure 9:
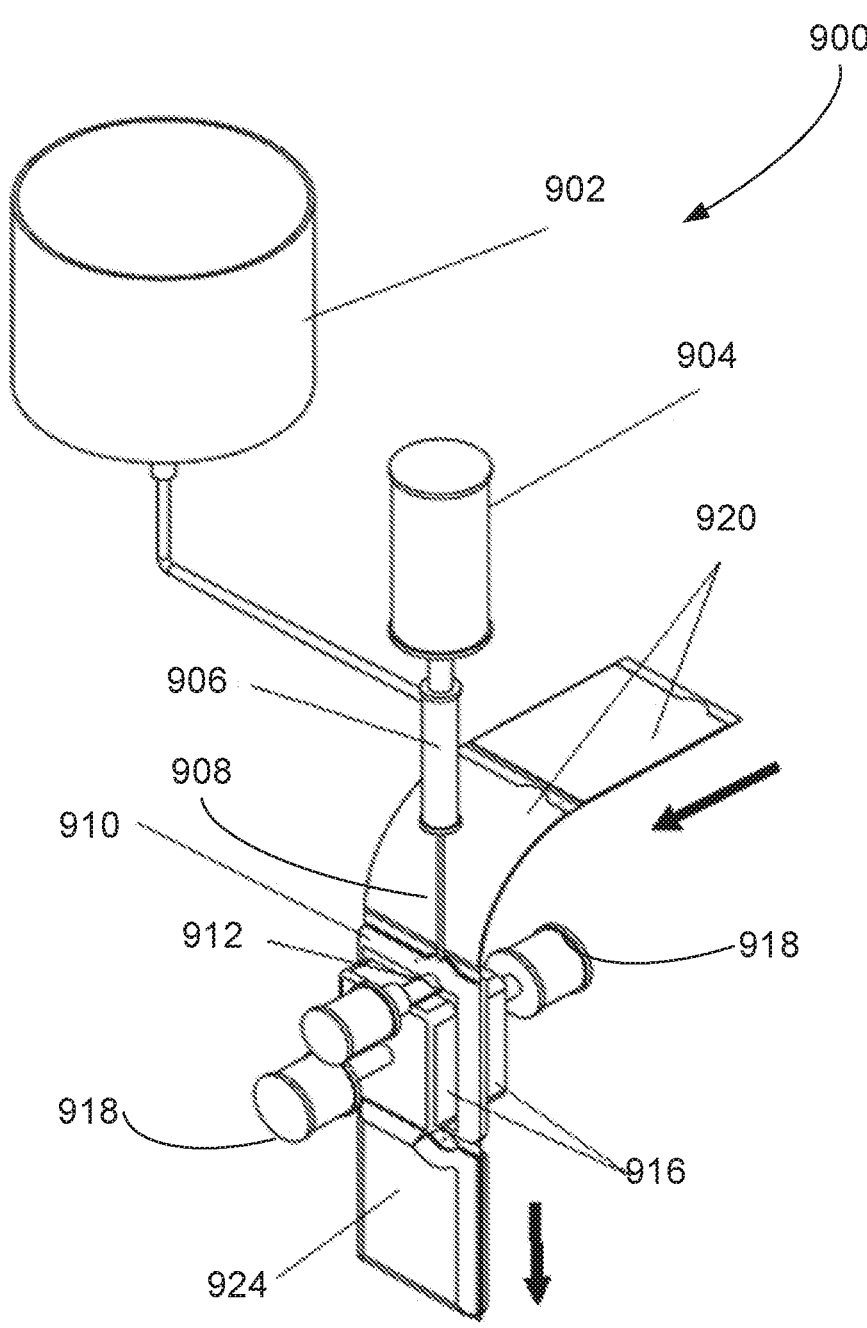
FIG. 9 is a simplified illustration of a refrigerant filling and sealing machine according to an example embodiment of the invention.

Reference is now made to FIG. 9, which is a simplified illustration of a refrigerant filling and sealing machine according to an example embodiment of the invention.

FIG. 9 shows a refrigerant filling and sealing machine 900, including:

a tank 902 for refrigerant fluid such as, by way of a non-limiting example, water;

an optional pressurization component or piston 904 for optionally pressurizing and/or propelling the refrigerant fluid for injection into SAM packs 920;

a plunger 906 for feeding the optionally pressurized refrigerant fluid to a needle 908;

the needle 908 for injecting refrigerant fluid into a SAM pack 910;

an optional sealer 912 for sealing a SAM pack 920 which has been injected with refrigerant fluid;

an optional suction device 916 for pulling sides of the SAM pack 910 away from each other, separating the sides and optionally enabling entrance of the needle 908 without punching through both sides of the SAM pack 910; and an optional solenoid or piston 918 for operating the suction device 916, pushing against the SAM pack 910 and/or pulling away from the SAM pack 910.

FIG. 9 also shows a pack 924 which contains refrigerant fluid, and appears thicker than a SAM pack 920.

In some embodiments the optional pressurization component 904 is a piston for providing pressure to the refrigerant fluid.

In some embodiments the plunger 906 and needle 908 are optionally components of a syringe.

In some embodiments the sealer 912 is a heat sealer, optionally solenoid operated or piston operated.

In some embodiments the machine 900 uses tap water as a refrigerant fluid, the tap water typically provided at a pressure of 1-4 bars. In some embodiments the machine 900 uses tap water as a refrigerant fluid, and does not include a tank 902.

Figure 10A:
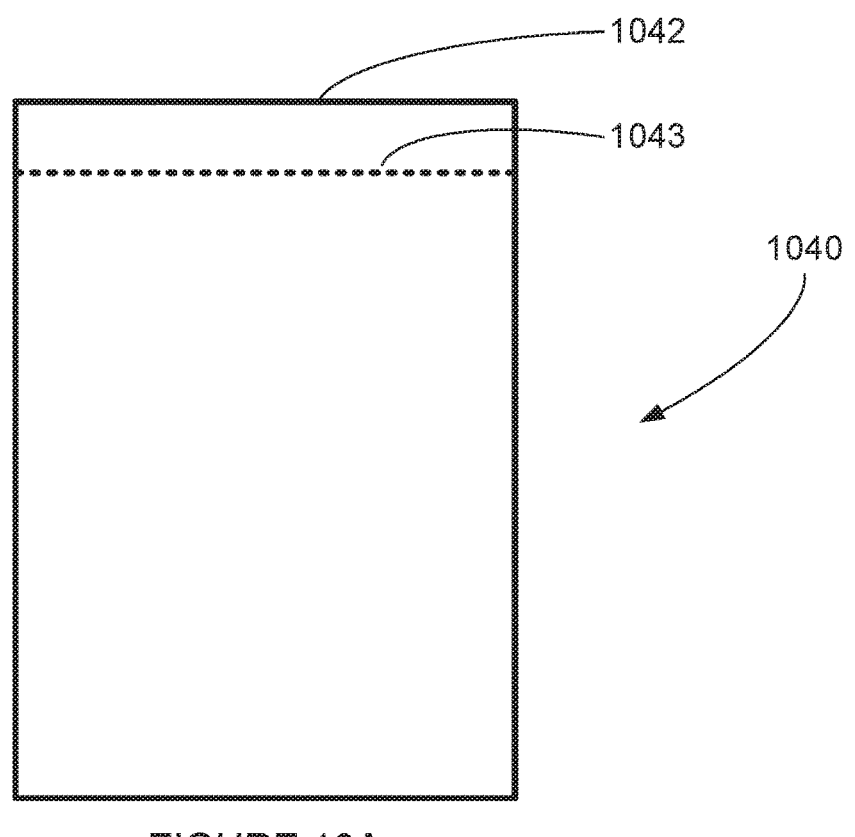
FIG. 10A is a simplified illustration of a SAM pack.
Figure 10B:
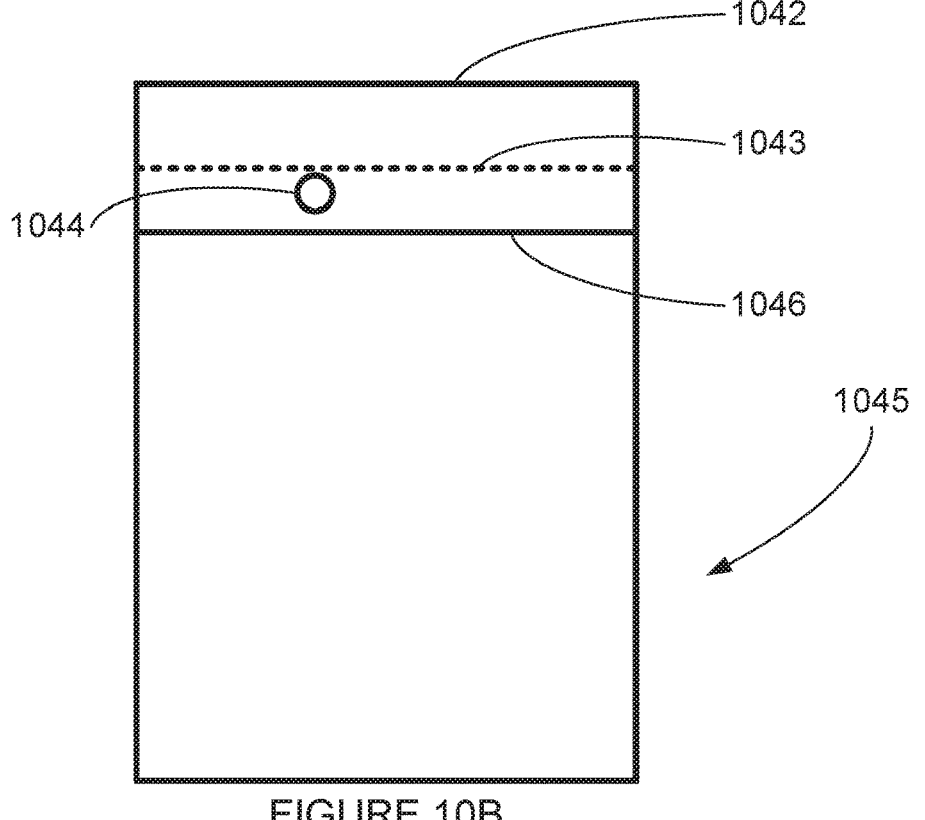
FIG. 10B is a simplified illustration of a pack which has been injected with refrigerant fluid, according to an example embodiment of the invention.

Reference is now made to FIG. 10A, which is a simplified illustration of a SAM pack, and FIG. 10B, which is a simplified illustration of a pack which has been injected with refrigerant fluid, according to an example embodiment of the invention.

FIG. 10A shows a SAM pack 1040. The SAM pack 1040 may include all seams at the edges of the SAM pack 1040, or some seams, such as a top seam 1043, somewhat inward from an edge 1042 of the SAM pack 104.

FIG. 10B shows a refrigerant pack 1045, which is the SAM pack 1040 after a hole 1044 has been made in the SAM pack 1040, refrigerant fluid has been injected into the pack, and the refrigerant fluid filled pack has optionally been sealed by a seam 1046 which seals off a section of the refrigerant pack 1045 which includes the hole 1044.

In some embodiments, the hole 1044 is made in a body of the SAM pack 1040, inward of the seam 1043. In some embodiments, where a seam of the SAM pack 1040 is at an edge of the SAM pack, the hole is inward of the edge 1042.

In some embodiments the refrigerant pack 1045 is optionally sealed by the seam 1046 located between a body of the refrigerant pack 1045, containing all or most of the SAM and refrigerant fluid, and the hole 1044.

Figure 10C:
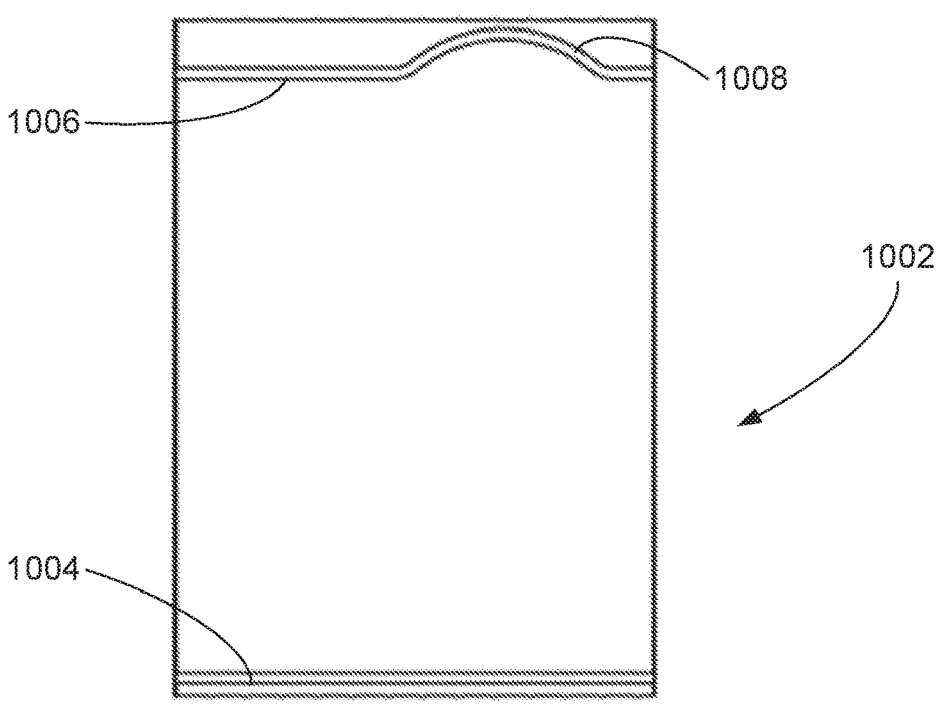
FIG. 10C is a simplified illustration of a SAM pack.
Figure 10D:
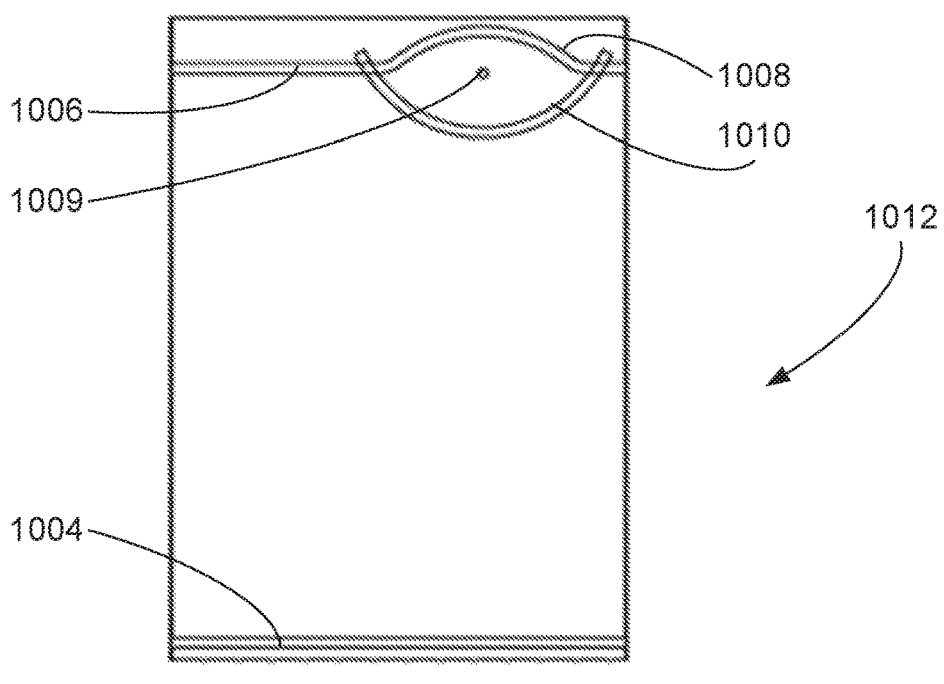
FIG. 10D is a simplified illustration of a pack which has been injected with refrigerant fluid, according to an example embodiment of the invention.

Reference is now made to FIG. 10C, which is a simplified illustration of a SAM pack, and FIG. 10D, which is a simplified illustration of a pack which has been injected with refrigerant fluid, according to an example embodiment of the invention.

FIG. 10C shows a SAM pack 1002, with a first seam 1004 for example at a bottom of the SAM pack 1002, and a second seam 1006, for example at a top of the SAM pack 1002.

In some embodiments the second seam 1006 optionally includes at least a portion 1008 of the seam 1006 in a crescent shape, for an injector to inject refrigerant fluid into the SAM pack 1002 in a vicinity of the crescent shaped portion 1008.

FIG. 10D shows a pack 1012 with the first seam 1004 and the second seam 1006, which is the SAM pack 1002 after a hole 1009 has been made in the SAM pack 1002, refrigerant fluid has been injected into the SAM pack 1002, and the refrigerant fluid filled pack has been sealed by a seam 1010 which seals off a section of the pack 1012 which includes the hole 1009.

It is noted that FIGS. 10C and 10D describe a seam shape, regardless of whether that seam is at a top, bottom, or left or right side of a pack.

Figures 10E, 10F, 10G:
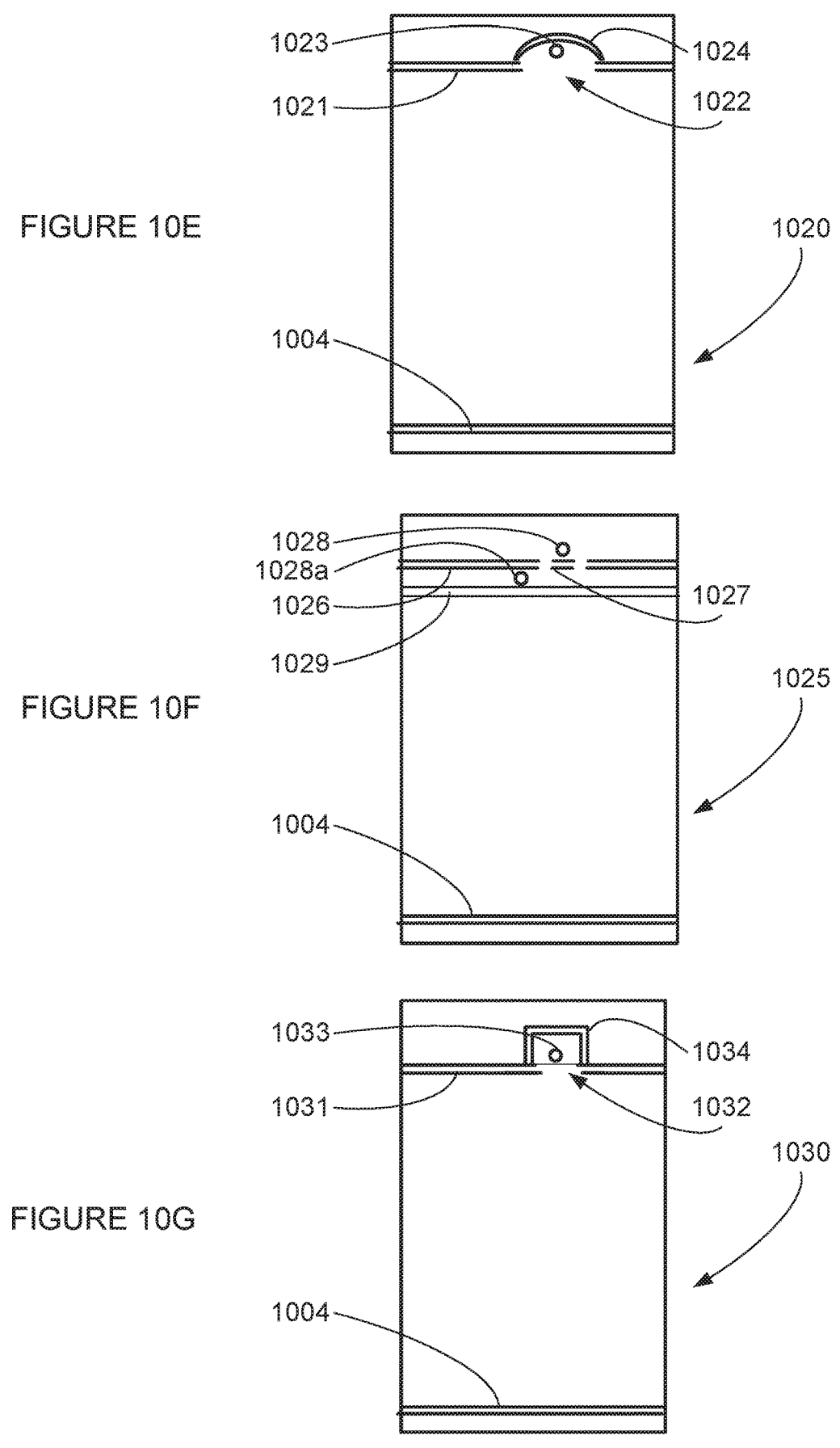

Reference is now made to FIG. 10E, which is a simplified illustration of a pack including a seam design according to an example embodiment of the invention.

FIG. 10E shows a pack 1020, with a bottom seam 1004 and a top seam 1021. When the pack contains SAM the seam 1021 is optionally not sealed along a portion 1022 of the seam 1021, or sealed weakly, as defined elsewhere herein, along the portion 1022 of the seam 1021.

In some embodiments the portion 1022 of the seam is sealed, whether glued or heat-sealed, so that a force of 50-500 grams pulling sides of the SAM pack 1020 apart opens the portion of the seam.

In some embodiments the portion 1022 of the seam is sealed, whether glued or heat-sealed, so that a fluid refrigerant pressure in a range of 0.25-5 bars opens the portion 1020 of the seam.

Refrigerant fluid is optionally injected through a location 1023 which is located above a line of the seam 1021, next to the not-sealed portion 1022 of the seam 1021. Following the injection, the pack 1020 is optionally sealed.

In some embodiments the optional sealing is optionally performed along a line 1024. In some embodiments the line 1024 is crescent shaped, sealing the not-sealed portion 1022 of the seam 1021.

In some embodiments the sealing is optionally performed at the not-sealed portion 1022 of the seam 1021, and/or along a straight line of the seam 1021, sealing the not-sealed portion 1022 of the seam 1021.

In some embodiments the sealing is optionally performed both at the not-sealed portion 1022 of the seam 1021, and along the line 1024.

Reference is now made to FIG. 10F, which is a simplified illustration of a pack including a seam design according to an example embodiment of the invention.

FIG. 10F shows a pack 1025, with a bottom seam 1004 and a top seam 1026. In some embodiments, when the pack contains SAM the seam 1026 is optionally not sealed, or weakly sealed, along a portion 1027, or even all, of the top seam 1026.

Refrigerant fluid is optionally injected through a location 1028 which is located above a line of the seam 1026, next to the not-sealed or weakly sealed portion 1027 of the seam 1026. Following the injection, the pack 1025 is optionally sealed.

In some embodiments the portion 1027 of the seam is sealed, whether glued or heat-sealed, so that a force of 50-500 grams pulling sides of the SAM pack 1025 apart opens the portion of the seam.

In some embodiments the portion 1027 of the seam is sealed, whether glued or heat-sealed, so that a fluid refrigerant pressure in a range of 0.25-5 bars opens the portion 1027 of the seam.

In some embodiments the sealing is optionally performed along a line of the seam 1026.

In some embodiments the sealing is optionally performed only along the not-sealed portion 1027. In some embodiments the sealing is optionally performed along the entire seam 1026. In some embodiments the sealing is optionally along a line 1029 parallel to the seam 1026.

In some embodiments, when the pack contains SAM the seam 1026 is sealed along all its length, Refrigerant fluid is optionally injected through a location 1028a which is located below a line of the seam 1026, and optionally sealed along a line 1029 parallel to the seam 1026.

Reference is now made to FIG. 10G, which is a simplified illustration of a pack including a seam design according to an example embodiment of the invention.

FIG. 10G shows a pack 1030, with a bottom seam 1004 and a top seam 1031. When the pack contains SAM the seam 1031 is optionally not sealed along a portion 1032 of the seam 1031.

Refrigerant fluid is optionally injected through a location 1033 which is located above a line of the seam 1031, next to the not-sealed portion 1032 of the seam 1031. Following the injection, the pack 1030 is optionally sealed.

In some embodiments the sealing is optionally performed along a line 1034. In some embodiments the line 1034 is shaped to seal off the not-sealed portion 1032, by way of a non-limiting example by a rectangular-shaped seam 1034.

In some embodiments the sealing is optionally performed at the not-sealed portion 1032 of the seam 1031, or along a straight line of the seam 1031, sealing the not-sealed portion 1032 of the seam 1031.

Additional Notes about Example Embodiments

Wherever sealing a pack is described in the present application and claims, the sealing may be performed by heat sealing and/or by gluing.

In some embodiments refrigerant fluid is added via a non-return valve.

Wherever SAM is described in the present application and claims, the absorbent material may be a Super Absorbent Material, SAP; or gelatin, or some other absorbent material. In some embodiments a preservative material, such as, by way of some non-limiting examples a micro-organism growth retardant material and/or potassium sorbate is added to the SAM.

Wherever a refrigerant fluid is described in the present application and claims, the refrigerant fluid may be water, de-salinated water, treated water, diethylene glycol, ethylene glycol, and/or a mixture thereof.

Cold Pack Parameters

Parameters for cold pack dispensing include, by way of some non-limiting examples:

Size of pack;

Weight of cold pack including refrigerant fluid;

Amount of refrigerant fluid in pack;

Amount of SAM in pack;

Temperature of pack;

Location of injection point relative to pack shape;

SAM in pack; and

Type of refrigerant fluid for adding to pack.

Determining Cold Pack Temperature, Number and Size

In some embodiments, pack temperature is kept above a specific temperature, so as not to harm products with which the pack is placed.

In some embodiments, pack temperature is kept above freezing. In some embodiments, pack temperature is cooled to freezing, and the pack is not frozen. In some embodiments, pack temperature is cooled to freezing, and the pack is also frozen, potentially enabling more cooling using the latent heat of melting. In some embodiments, pack temperature is cooled to below freezing.

In some embodiments, pack temperature is made as low as possible, to maintain cold for a longer time than higher temperatures.

In some embodiments, a pack size is selected to be large, to maintain cold for a longer time than a smaller pack. In some embodiments, a number of packs to be used in packaging product(s) is selected to be more than one, optionally many more than one, to maintain cold for a longer time than one pack or a smaller number of packs.

In some embodiments the packs optionally provide cooling action over a period of hours, and even days, for example 1 day, 2 days, 3 days, up to 7 days or even 14 days.

Determining a Temperature for Cold Packs.

In some embodiments, a cold pack temperature of 4 degrees Celsius is selected, for use in packaging with some products, such as, by way of some non-limiting examples, pharmaceuticals and/or groceries which are to be kept cold but not frozen.

In some embodiments, a cold pack temperature of 0 degrees Celsius, and not frozen, is selected, for use in packaging with some products. Such a cold pack will provide a cooling effect for a shorter period of time than a 0 degrees Celsius and yet frozen cold pack. Such a cold pack potentially does not freeze a product with which it is packaged.

In some embodiments, a cold pack temperature of 0 degrees and frozen is selected, for use in packaging with some products. Such a cold pack will provide a cooling effect for a longer period of time than a cold pack at 0 degrees Celsius and not frozen.

In some embodiments, a cold pack temperature of −5 degrees Celsius is selected, for use in packaging with some products, such as, by way of a non-limiting example, some pharmaceuticals.

In some embodiments, a cold pack temperature of −18 degrees Celsius is selected, for use in packaging with some groceries. Such a temperature potentially reproduces temperature of some household freezers.

In some embodiments, a cold pack temperature of −30 degrees Celsius is selected, for use in packaging with some frozen products, by way of a non-limiting example such as meat.

In some embodiments, a cold pack temperature of −40 degrees Celsius is selected, for use in packaging with frozen products which may spend a long time in transit.

In some embodiments, pack temperature is kept above a specific temperature, so as not to harm products with which the pack is placed.

In some embodiments, pack temperature is made as low as possible, to maintain cold for a longer time than higher temperatures.

Determining Cold Pack Quantity Per Package/Box and Cold Pack Size

In some embodiments, a cold pack size is selected to be large, to maintain cold for a longer time than a smaller pack. In some embodiments, a number or quantity of packs to be used in packaging product(s) is selected to be more than one, optionally many more than one, to maintain cold for a longer time than one pack or a smaller number of packs.

Translating Goods Packing Parameters to Cold Pack Machine Operating Parameters

In some embodiments goods packing parameters defining an optional cold pack request are translated to machine operation parameters or instructions.

In some embodiments the cold pack request is translated, via a look-up table, to a number and/or temperature and/or size of cold packs and/or other cold pack parameters as described herein.

The look-up table optionally includes one or more input parameters such as, by way of some non-limiting examples, weight, volume, type of goods, insulation properties of a packing box and/or type of box, expected time of goods staying in the box during shipment to destination.

The look-up table optionally includes one or more output parameters such as, by way of some non-limiting examples, temperature, size of cold pack, number of cold packs, cooling blower operating intensity or setting.

In some embodiments the cold pack request is translated, via a look-up table, to a number and/or temperature and/or size of cold packs and/or other cold pack parameters as described herein.

In some embodiments the cold pack request is translated, by calculation, to a number and/or temperature and/or size of cold packs and/or other cold pack parameters as described herein. The calculation may be based on estimated heat retention and/or dissipation properties of the goods in a box and of the box.

Providing Cold Packs at a Specific Temperature.

In some embodiments, a cold pack machine is optionally empty of cold packs when a request for cold packs at a specific temperature arrives. In some embodiments, the cold pack machine manufactures a number of cold packs per the request, at the temperature requested.

In some embodiments, a cold pack machine optionally already contains cold packs at a first temperature when a request for additional cold packs at the first specific temperature arrives, and the cold pack machine dispenses a requested number of cold packs at the first requested temperature.

In some embodiments, a cold pack machine optionally already contains cold packs at a first temperature when a request for additional cold packs at a second, warmer temperature arrives. The cold pack machine optionally warms the requested number of cold packs to the requested second temperature and optionally dispenses the requested number of cold packs at the second requested temperature. In some embodiments the warming is by blowing warm air instead of cold air through a cold pack refrigerating section of the cold pack machine, optionally controlling the desired temperature and halting the warming when the second temperature is reached.

In some embodiments, a cold pack machine optionally already contains cold packs at a first temperature when a request for additional cold packs at a second, colder temperature arrives.

The cold pack machine optionally refrigerates the requested number of cold packs to the requested second temperature and optionally dispenses the requested number of cold packs at the second requested temperature. In some embodiments the refrigeration is by blowing more cold air, and/or colder air, through a cold pack refrigerating section of the cold pack machine, optionally controlling the desired temperature and halting the refrigeration when the second temperature is reached.

It is expected that during the life of a patent maturing from this application many relevant absorbent materials will be developed and the scope of the terms "absorbent material" and SAM are intended to include all such new technologies a priori.

It is expected that during the life of a patent maturing from this application many relevant refrigerant fluids will be developed and the scope of the term refrigerant fluid is intended to include all such new technologies a priori.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for dispensing a cold pack comprising:
a filling unit for taking in a bag and adding refrigerant fluid to an inside of the bag, producing a refrigerant pack; and
a cooling unit for cooling the refrigerant pack, producing a cold pack,
wherein the bag comprises a completely sealed and waterproof SAM bag with SAM sealed and waterproofed inside and without refrigerant fluid inside, and wherein said bag is configured to be re-sealed by heat sealing after puncturing said bag; wherein said puncturing allows the SAM pack to be injected with refrigerant fluid via the puncture; and
wherein said SAM pack has a cavity for containing said SAM, and said cavity is waterproof.

2. The system of claim 1, and further comprising a sealing unit for sealing the refrigerant pack.

3. The system of claim 1, and further comprising a conveyor belt, for taking in refrigerant packs and passing the refrigerant packs through the cooling unit to emerge as cold packs cooled to a desired temperature.

4. The system of claim 1, in which the filling unit comprises an injection needle for injecting the refrigerant fluid to the inside of the bag.

5. The system of claim 1, in which the filling unit is arranged to perform the adding refrigerant fluid to the inside of the bag through a side of the bag.

6. A method of providing a cold pack comprising:
providing a bag;
adding refrigerant fluid to an inside of the bag, thereby producing a refrigerant pack;
sealing the refrigerant pack;
cooling the refrigerant pack, thereby producing a cold pack; and
providing the cold pack,
wherein the bag comprises a completely sealed and waterproof SAM bag with SAM sealed and waterproofed inside and without refrigerant fluid inside, wherein said bag is configured to be re-sealed by heat sealing after puncturing said bag; wherein said puncturing allows the SAM pack to be injected with refrigerant fluid via the puncture;
wherein said SAM pack has a cavity for containing said SAM, and said cavity is waterproof.

7. The method of claim 6, and further comprising using a conveyor belt for taking in refrigerant packs and passing the refrigerant packs through a cooling unit to emerge as cold packs cooled to a desired temperature.

8. The method of claim 6, in which adding refrigerant fluid to an inside of the bag comprises injecting the refrigerant fluid to the inside of the bag.

9. The method of claim 6, in which adding refrigerant fluid to an inside of the bag is performed through a side of the SAM pack.

10. The method of claim 6, and further comprising receiving an electronic request for dispensing cold packs, and providing a specific number of cold packs at a specific designated temperature, based on the electronic request.

11. A system for dispensing a refrigerant pack comprising:
providing a sealed bag;
puncturing said sealed bag and injecting refrigerant fluid to an inside of the bag, thereby producing a refrigerant pack; and
re-sealing the refrigerant pack by heat sealing,
wherein the filling unit comprises an injector for injecting the refrigerant fluid to the inside of the bag,
wherein the sealed bag comprises a completely sealed and waterproof SAM bag with SAM sealed and waterproofed inside and without refrigerant fluid inside;
wherein said SAM pack has a cavity for containing said SAM, and said cavity is waterproof.

12. A completely sealed, closed, and waterproof SAM pack with SAM sealed and waterproofed inside and without refrigerant fluid inside, wherein said SAM pack is configured to be re-sealed by heat sealing after puncturing said SAM pack; wherein said puncturing allows the SAM pack to be injected with refrigerant fluid via the puncture;
wherein said SAM pack has a cavity for containing said SAM, and said cavity is waterproof.

13. A method of providing a refrigerant pack comprising:
providing a sealed bag;
adding refrigerant fluid to an inside of the sealed bag, thereby producing a refrigerant pack; and
re-sealing the refrigerant pack by heat sealing;
wherein the adding refrigerant fluid comprises puncturing said sealed bag and injecting the refrigerant fluid to the inside of the bag,
wherein the sealed bag comprises a completely sealed, closed, and waterproof SAM pack with SAM sealed and waterproofed inside and without refrigerant fluid inside according to claim 12.

14. The method of claim 13, wherein the refrigerant fluid comprises water.

15. The SAM pack of claim 12, wherein a portion of a seam is sealed weakly enough and arranged to open in response to a force of 50-500 grams pulling sides of the SAM pack apart when the sides are pulled apart while being held by vacuum.

16. The SAM pack of claim 12, in which the SAM pack comprises a seam shaped to enable puncturing the SAM pack, adding a refrigerant fluid, and re-sealing, producing a refrigerant pack.

17. The SAM pack of claim 12, wherein the SAM pack comprises a plurality of chain-linked SAM packs.

18. The SAM pack of claim 17, wherein the strip of SAM packs comprises a strip of fan-folded SAM packs.

19. The SAM pack of claim 17, wherein the strip of SAM packs comprises a strip of SAM packs packaged as a roll.

20. The SAM pack of claim 17, wherein a thickness of the SAM pack is less than 20 millimeters.

21. The SAM pack of claim 12, wherein the pack contains less than 10 grams SAM per 500 cc internal volume.

22. The SAM pack of claim 12, wherein the pack contains SAM in a weight of less than 2% of a weight of said same pack when filled with water.

23. The SAM pack of claim 12 configured as a refrigerant pack.

24. The SAM pack of claim 12, wherein a thickness of the SAM pack is less than 20 millimeters.

25. The SAM pack of claim 12 having a top sealing seam and a bottom sealing seam, wherein said top sealing seam and said bottom sealing seam have a linear shape.

26. The SAM pack of claim 12 having a rectangular shape.

27. The SAM pack of claim 12, wherein said SAM pack has a volume suited to accommodate said SAM and said refrigerant fluid upon said injection.

28. The SAM pack of claim 12, wherein said SAM pack has a cavity for containing said refrigerant fluid, and said cavity consists of a single chamber.

29. A method of producing a waterproof SAM pack comprising:

forming a pack of waterproof material;

adding SAM to the pack without adding refrigerant fluid, producing a SAM pack; and sealing the SAM pack closed so the SAM pack is completely sealed and waterproof;

wherein the SAM pack comprises a completely sealed and waterproof SAM bag with SAM sealed and waterproofed inside and without refrigerant fluid inside, wherein said SAM pack is configured to be re-sealed by heat sealing after puncturing said SAM pack; wherein said puncturing allows the SAM pack to be injected with refrigerant fluid via the puncture;

wherein said SAM pack has a cavity for containing said SAM, and said cavity is waterproof.

30. The method of claim 29, in which the sealing the SAM pack comprises sealing in a seam shape which enables puncturing the SAM pack, adding a refrigerant fluid, and re-sealing.

\* \* \* \* \*